(12) United States Patent
Cheng et al.

(10) Patent No.: US 7,025,993 B2
(45) Date of Patent: Apr. 11, 2006

(54) HERBAL COMPOSITION PHY906 AND ITS USE IN CHEMOTHERAPY

(75) Inventors: Yung-Chi Cheng, Woodbridge, CT (US); Shwu-Huey Liu, Madison, CT (US)

(73) Assignee: Yale University, New Haven, CT (US)

( * ) Notice: Subject to any disclaimer, the term of this patent is extended or adjusted under 35 U.S.C. 154(b) by 153 days.

(21) Appl. No.: 10/220,876

(22) PCT Filed: Mar. 8, 2001

(86) PCT No.: PCT/US01/07353

§ 371 (c)(1),
(2), (4) Date: Dec. 30, 2002

(87) PCT Pub. No.: WO01/66123

PCT Pub. Date: Sep. 13, 2001

(65) Prior Publication Data

US 2003/0211180 A1 Nov. 13, 2003

Related U.S. Application Data

(63) Continuation-in-part of application No. 09/522,055, filed on Mar. 9, 2000, now abandoned.

(51) Int. Cl.
*A01K 35/78* (2006.01)

(52) U.S. Cl. .................................................... 424/725
(58) Field of Classification Search ............... 424/725, 424/195.1, 766
See application file for complete search history.

(56) References Cited

U.S. PATENT DOCUMENTS

| | | | |
|---|---|---|---|
| 4,613,591 A | 9/1986 | Aburada et al. | 514/34 |
| 4,618,495 A | 10/1986 | Okuda et al. | 424/195.1 |
| 5,437,866 A | 8/1995 | Sun | 424/195.1 |
| 5,665,393 A | 9/1997 | Chen et al. | 424/489 |
| 6,048,847 A | 4/2000 | Ramadoss et al. | 514/169 |

OTHER PUBLICATIONS

Huey Liu Shwu et al., "Prevention of CPT–11 Induced Toxicity by a Chinese Medicinal Formulation, PHY–906". Proceedings of the American Association for Cancer Research Annual, No. 41, Mar. 2000, p. 410, XP001018859.

Shwu–Huey Liu et al., "A Chinese Medicine Formulation, PHY–906, Can Enchance The Therapeutic Index of CPT–11 and other Anticancer Drugs Against Cancer in Mice". Proceedings of the American Association for Cancer Research Annual, vol. 42, Mar. 2001, p. 85, XP001018879.

M. Narita et al., "Inhibition of Beta–Glucuronidase by Natural Glucurondes of Kampo Medicines Using Glucuronide of SN–38(7–ETHYL–10–Hydroxycamptothecin) as a Substrate", Xenobiotia, vol. 23, No. 1, 1993, p. 5–10, XP001022293.

(Continued)

*Primary Examiner*—Patricia Leith
(74) *Attorney, Agent, or Firm*—Morgan, Lewis & Bockius LLP

(57) ABSTRACT

This invention provides herbal compositions useful for increasing the therapeutic index of drugs, including those used in the treatment of disease, especially viral infections and neoplasms of cancer. This invention provides methods useful for improving the quality of life of an individual undergoing chemotherapy. Furthermore, this invention improves the treatment of disease by increasing the therapeutic index of chemotherapy drugs by administering the herbal composition PHY906 to a person undergoing such chemotherapy.

13 Claims, 20 Drawing Sheets

OTHER PUBLICATIONS

Kiyoshi Takasuna et al., "Protective Effects of Kampo Medicines and Baicalin Against Intestinal Toxicity of a New Anticancer Camptothecin Derivative, Irinotecan Hydrochloride (CPT–11), in Rats", Japanese Journal of Cancer Research, vol. 86, No. 10, 1995, p. 978–984, XP001022186.

K. Mori et al., "Kampo Medicines for the Prevention of Irinotecan —Induced Diarrhea in Advanced Non–Small cell Lung Cancer", Gan T Kagaku Ryoho Japanese Journal of Cancer and Chemotherapy, (Jul. 1998) 25 (8) 1159–63, XP001022284.

R. M. Goldberg et al., "Irinotecan Plus 5–Fu and Leucovorin in Advanced Colorectal Cancer: North American Trials" Oncology, S. Karger Ag, Basel, CH, vol. Suppl. 6, No. 6, Aug. 1998, p. 59–63.

Bleiberg H., European J. of Cancer, 35(3), 371–379, 1999.

Govindarajan et al., Lancet, 356:566, 2000 (Aug. 12).

Stucky–Marshall L., Cancer Nursing, 22(3), 212, 1999.

| t-tst (*PVALUE) AT DAY 14 | CONTROL (VEHICLE) | CPT-11 | PHY 906 |
|---|---|---|---|
| CPT011 | 0.02 | — | 0.02 |
| PHY 906 | 0.6 | 0.02 | — |
| CPT-11 + PHY 906 | 0.002 | 0.01 | 0.003 |

FIG. 18
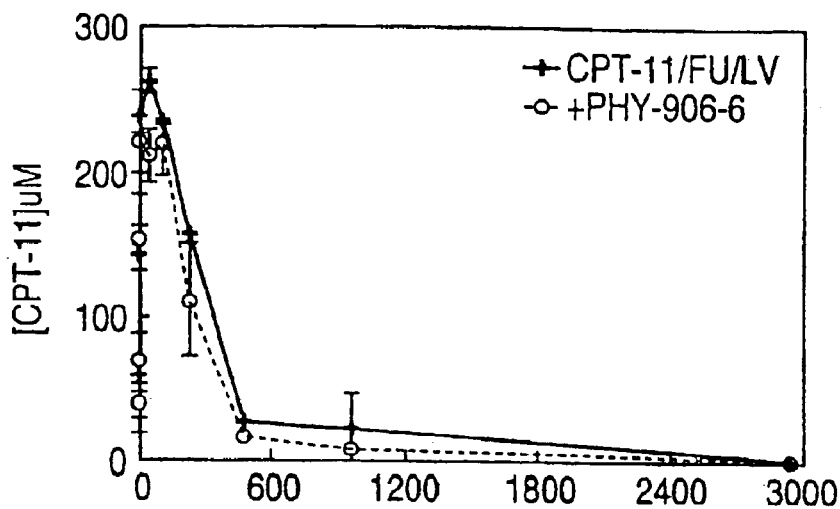
FIG. 18A
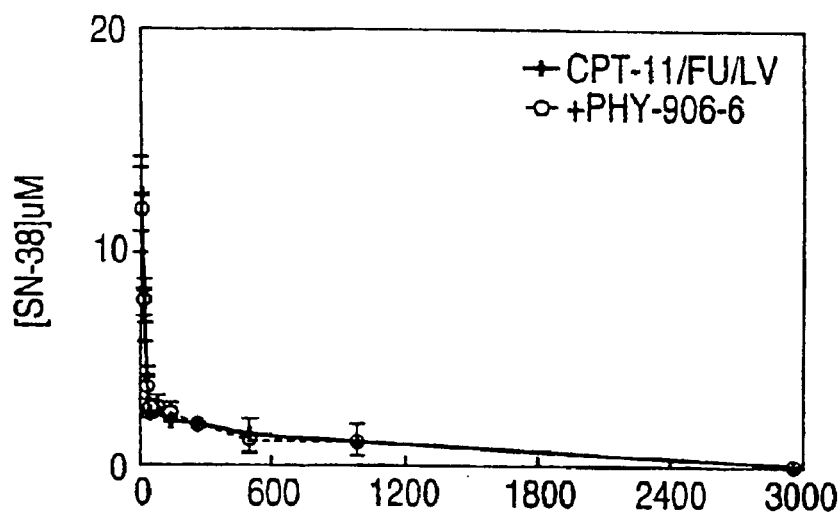
FIG. 18B
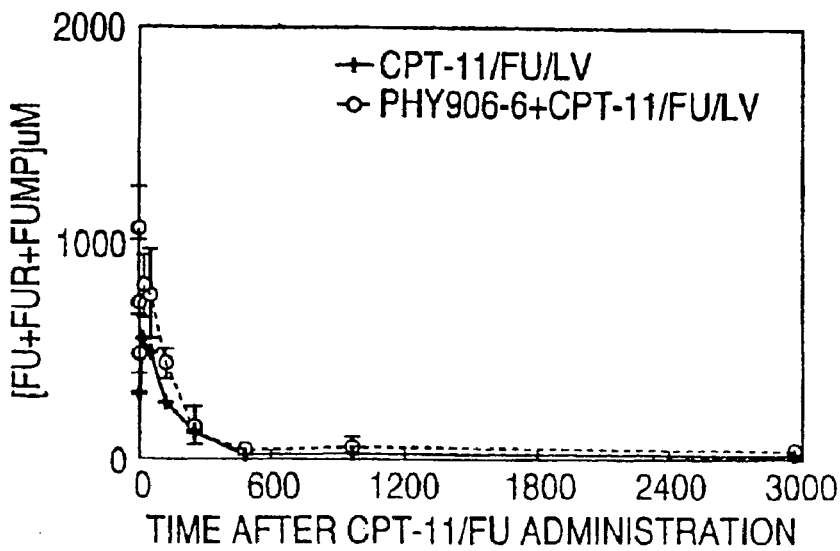
FIG. 18C

FIG. 19
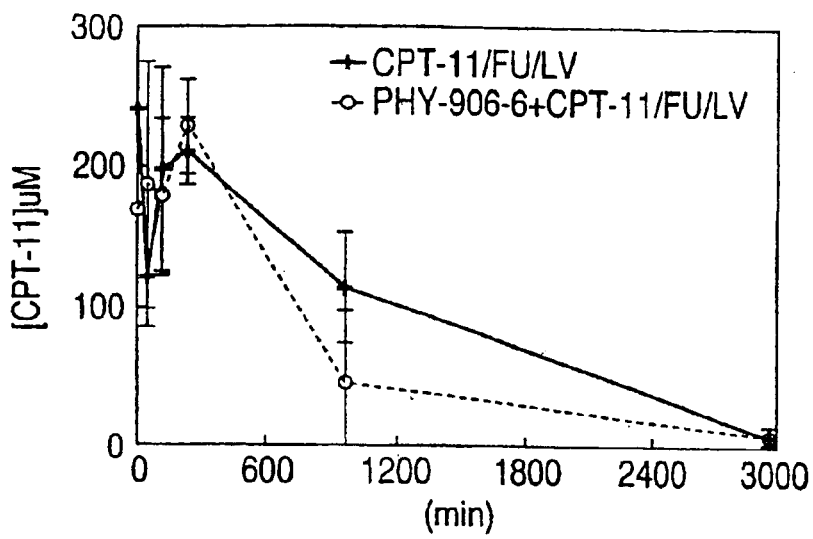
FIG. 19A
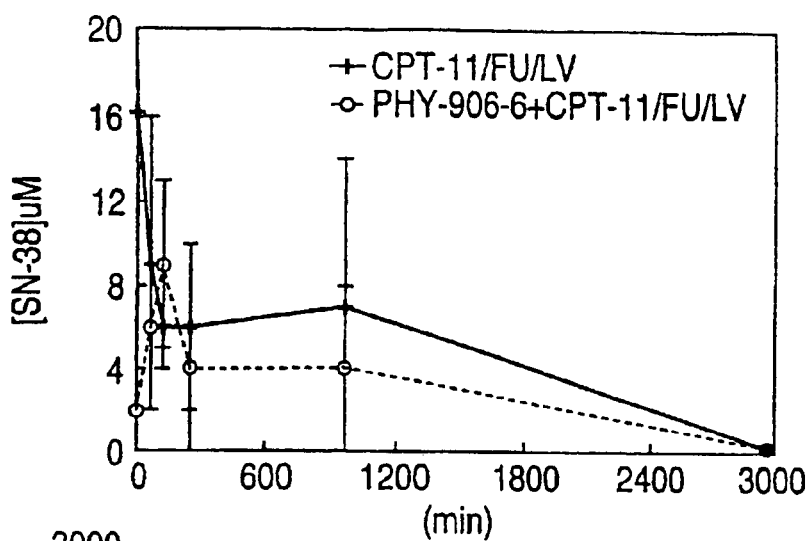
FIG. 19B
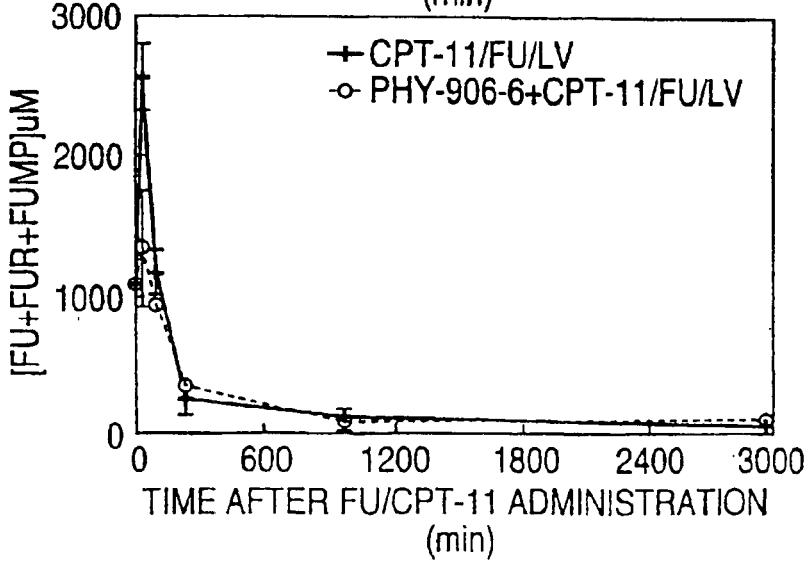
FIG. 19C

FIG. 20
FIG. 20A
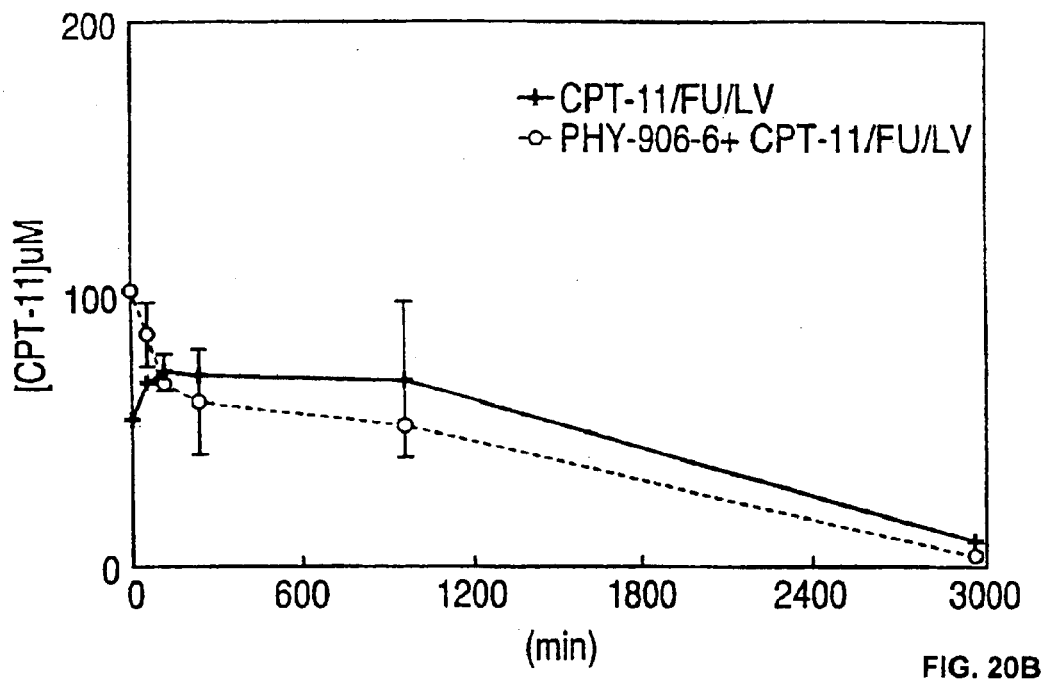
FIG. 20B
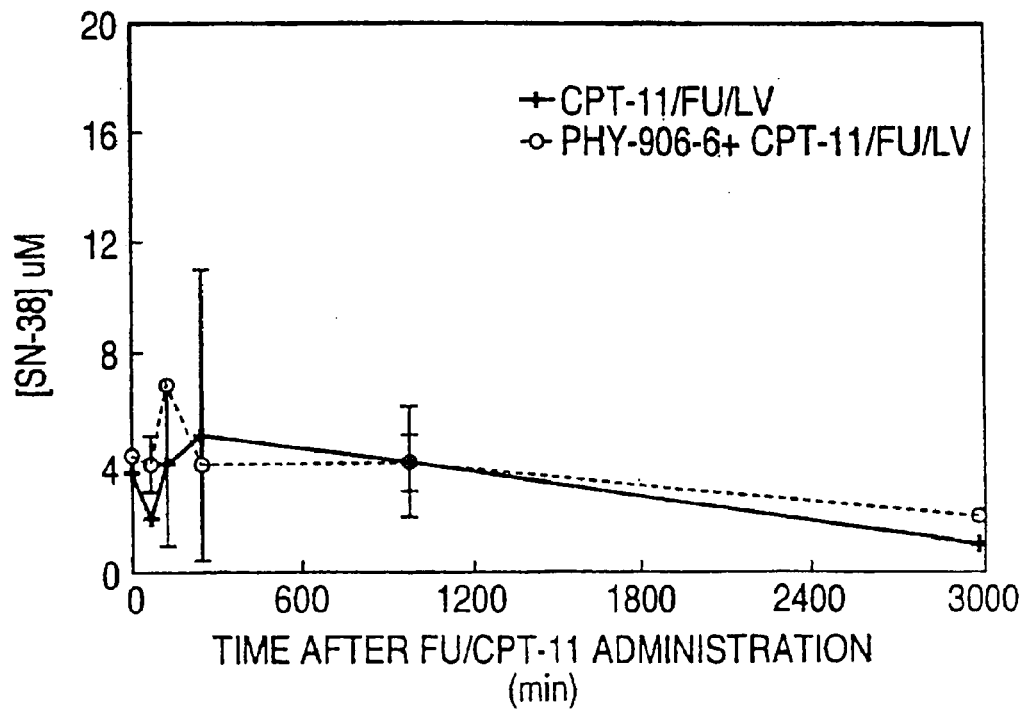

HERBAL COMPOSITION PHY906 AND ITS USE IN CHEMOTHERAPY

This application is a national stage (35 U.S.C. § 371) application of PCT/US01/07353, filed on Mar. 8, 2001, which claims the priority as a continuation in part of U.S. application Ser. No. 09/522,055, filed on Mar. 9, 2000, now abandoned.

FIELD OF THE INVENTION

The present invention relates to herbal compositions and herbal extracts useful for increasing the therapeutic index of drugs, including those used in the treatment of disease, especially viral infections and neoplasms of cancer. The methods of the present invention can be used to improve the quality of life of an individual undergoing chemotherapy. Specifically, the invention relates to the treatment of disease by increasing the therapeutic index of chemotherapy drugs by the herbal composition PHY906. More specifically, the invention relates to the treatment of cancer by increasing the therapeutic index of cancer chemotherapy drugs by the herbal composition PHY906.

BACKGROUND OF THE INVENTION

All publications and patent applications herein are incorporated by reference to the same extent as if each individual publication or patent application was specifically and individually indicated to be incorporated by reference.

I. Herbal Medicine

Herbal medicine has been in use for centuries by people of Asia and Europe. In the United States (US), herbs have become commercially valuable in the dietary supplement industry as well as in holistic medicine. Approximately one third of the US population has tried some form of alternative medicine at least once (Eisenberg et al., N. Engl. J. Med., 328:246–252 (1993)). Botanicals have also become a focal point for the identification of new active agents to treat diseases. Active compounds, derived from plant extracts, are of continuing interest to the pharmaceutical industry. For example, taxol an antineoplastic drug obtained from the bark of the western yew tree, has been found to be useful in the treatment of breast cancer (Gomez-Espuch et al., Bone Marrow Transplant, 25(3):231–235 (2000)).

There are many branches of herbal medicine around the world, such as Ayurveda, Unani, Sida and Traditional Chinese Medicine (TCM). While modem Western medicine typically consists of administering a single chemical entity capable of intervening a specific biochemical pathway, each formula of TCM contains hundreds of chemical entities from several herbs which are designed to interact with multiple targets in the body in a coordinated manner. Although empirical practice contributed in a significant way to the herbal composition and prescription of these ancient herbal medicines, they are also supported, to a varying degree, by a set of theories which all are distinct from-that of modem Western medicine in terms of anatomy, pharmacology, pathology, diagnosis treatment, etc. Among the different herbal medicine fields, TCM has developed a more complete set of theories over several centuries which have been well documented and practiced by local physicians caring for a huge population (>1.3 billion people) in greater China and in East Asia including Korea and Japan.

II. Traditional Chinese Medicine

Western medicine generally uses purified compounds, either natural or synthetic, mostly directed towards a single physiological target. However, the compositions used in TCM are usually composed of multiple herbs and compounds which are aimed at multiple targets in the body based on unique and holistic concepts. TCM mainly use processed crude natural products, with various combinations and formulations, to treat different conformations resulting in fewer side effects. The great potential of TCM has yet to be realized for the majority of the world's people.

Mixtures of botanical extracts, rather than a single compound are widely used throughout the world for the management of disease and are slowly gaining increased acceptance in Western countries (Okada, F., Lancet 348: 5–6 (1996); Xiao P G, Xing S T and Wang L W, Journal of Ethnopharmacol 38: 167–175 (1993)). The use of traditional Chinese medicine is based on the interaction of many chemical components in an herbal preparation that act simultaneously and synergistically on multiple molecular targets and cellular mechanisms. These components serve various functions; some may be responsible for efficacy while others may decrease toxicity or increase bioavailability. Chinese herbal formulations are perhaps the best known botanical drugs and have been derived from empiric observations in humans over the millennia. The claimed indication of a given Chinese medicinal preparation, in many cases, is multiple rather than single. This is not surprising, due to the many phyto-chemical ingredients in a formulation that could exert actions at multiple targets. It is possible that one Chinese medicinal formulation may relieve more than one side effect associated with the use of cancer chemotherapeutic agents.

The herbs in a typical TCM prescription are assigned roles as the principal herb and the secondary herbs, including assistant, adjuvant and guiding herbs. The principal herb produces the leading effects in treating the cause or the main symptom of a disease. An assistant herb helps to strengthen the effect of the principal herb and produces leading effects in the treatment of the accompanying symptoms. There are three types of adjuvant herbs: 1) those that enhance the therapeutic effects of the principal and assistant herbs or treat tertiary symptoms, 2) those that reduce or eliminate the toxicity and other side effects of the principal and the assistant herbs and 3) those that act on complementary target tissues not specifically affected by the principal herb. A guiding herb directs the effect of other herbs to the affected site and/or coordinates and mediates the effects of the other herbs in the prescription or formulation. In contrast to most of the herbal medicines or supplements that consist of one or more parts of a single plant, the intended effects of TCM are directed at multiple tissues.

For example, a well-known TCM recipe, "Ephedra Decoction" used for treating asthma is composed of ephedra, cinnamon twig, bitter apricot kernel and licorice. Ephedra, as the principal herb, which expels cold, induces diaphoresis and facilitates the flow of the Lung Qi to relieve asthma, the main symptom. Cinnamon twig, as the assistant herb, enhances ephedra's induction of diaphoresis and warms the Channels to ensure the flow of Yang Qi for reducing headache and pantalgia. Bitter apricot kernel, as the adjuvant herb, facilitates the adverse flow of the Lung Qi and strengthens the asthma relief by ephedra. Licorice as the guiding herb moderates the effects of both ephedra and cinnamon to ensure a homeostasis of the vital Qi. While each of the four herbs clearly exhibits its respective activity, they complement as well as supplement each other when they are combined. In practice, the principal herb can be prescribed with one or more secondary herbs, depending on the symptoms at a patient's presentation (*Prescriptions of Traditional Chinese Medicine*, Chapter One, pp10–16, E. Zhang, editor in Chief, Publishing House, Shanghai University of Traditional Chinese Medicine, 1998).

Qi refers to the total energy of the body. Herbs are used to achieve the optimum balance of Qi; that balance is believed to manifest itself in the overall health and vigor of the patient (K. C. Huang, The Pharmacology of Chinese Herbs, Second Edition, Page 2, 1999, CRC Press).

The main theories of TCM that guide the treatment of sickness with herbal medicine and other means, such as acupuncture, are 1) the theory of Yin and Yang; 2) the theory of Five Elements; 3) the theory of Viscera and Bowels; 4) the theory of Qi, Blood and Body Fluid; and 5) the theory of Channels and Collaterals.

In TCM, the first important aspect of making the proper diagnosis is to ascertain whether the disease is Yin or Yang, the two forces which the Chinese believe control the workings of the universe. Yin represents the feminine side of nature, encompassing darkness, tranquility, depth, cold, and wetness, while Yang represents a masculine principle, encompassing light, activity, height, heat, and dryness (K. C. Huang, The Pharmacology of Chinese Herbs, Second Edition, Page 2, 1999, CRC Press). Yin is commonly interpreted to be a negative force, while yang represents a positive force. The two forces are complementary, and neither can exist without the other. Thus, TCM attempts to achieve a balance between Yin and Yang.

In diagnosing a patient based on the philosophy of Yin and Yang, those patients who have a fever, are thirsty, constipated or have a rapid pulse condition are of Yang character. Those individuals who have an aversion to cold, are not thirsty, and diarrhea and a slow pulse condition are of Yin character. The property, flavor and function of herbs can also be classified according to Yin and Yang theory. For example, herbs of cold and cool nature belong to Yin, while herbs which are warm and hot in nature belong to Yang. Herbs with sour, bitter and salty flavor belong to Yin, while herbs with pungent, sweet and bland flavor belong to Yang. Herbs with astringent and subsiding function belong to Yin, while herbs with dispersing, ascending and floating function belong to Yang. In TCM, the principles of treatment are based on the predominance or weakness of Yin and Yang. Herbs are prescribed according to their property of Yin and Yang and their function for restoring the imbalance of the Yin and Yang. In so doing, the benefit of treatment is achieved.

According to the theory of Five Elements there are five basic substances that constitute the material world (i.e., wood, fire, earth, metal and water). In TCM this theory has been used to explain the physiology and pathology of the human body and to guide clinical diagnosis and treatment. Herbal physicians have applied the laws of generation, restriction, subjugation, and reverse restriction of the five elements to work out many effective and specific treatment regimens, such as reinforcing earth to generate metal (strengthening the function of the spleen to benefit the lung), replenishing water to nourish wood (nourishing the essence of the kidney to benefit the liver), supporting earth to restrict the wood (supplementing the function of the spleen to treat the hyperactivity of the liver), and strengthening water to control fire (replenishing the essence of the kidney to treat hyperactivity of the heart). Specifically, the property of some herbs is assigned to each of the five Elements for the purposes of guiding the prescription of a TCM recipe.

In TCM, the internal organs of the human body are divided into three groups: five Viscera (the Heart, the Liver, the Spleen, the Lung and the Kidney), Six Bowels (the Gall Bladder, the Stomach, the Large Intestine, the Small Intestine, the Urinary Bladder, and the Triple Warmer), the Extraordinary Organs (the Brain, the Medulla, the Bone, the Blood Vessel, the Gall Bladder, and the Uterus). In TCM, the Viscera or the Bowel are not only anatomic units, but also concepts of physiology and pathology concerning interactions among different organs. For example, the heart also refers to some of the mental functions and influence functions of blood, hair, tongue, and skin. Yin and Yang and the Five Elements influence the interactions among these internal organs, Viscera, Bowels, and Extraordinary Organs. The complexity of interplay of the theories is used to explain the pathology of diseases to which herbs are prescribed, as discussed below.

The prescription of herbal medicine in TCM starts with the diagnosis, which consists of four main items: interrogation, inspection, auscultation and olfaction, pulse taking and palpation. During the interrogation phase, much information is gathered, including the characteristics of the main symptoms. For instance, if the main symptom is characterized by the dull pain of the epigastric region, which may be relieved by warming and pressing, this suggests the insufficiency of the Spleen-Yang. Soreness and weakness of the loins and knees, intolerance of coldness with cold extremities manifests a weakness of the Kidney-Yang. During inspection, observations are made for vitality, skin color, and the general appearance and the condition of the tongue. For example, a pale complexion corresponds internally to the Lung of autumn, whose Qi is dry. This may occur when Yang Qi is lacking and the circulation of Qi and blood is impeded, or when the coldness in the channels and collaterals causes them to contract.

In TCM, it is from Qi, blood, and body fluid that come energy needed by the Viscera and Bowels, Channels and Collaterals, tissues, and other organs for carrying-out their physiological functions; and on which the formation and metabolism of Qi, blood and body fluid depend. Prescriptions of TCM consider the herbal effects on Qi and blood for treatments.

TCM holds that Channels, Collaterals, and their subsidiary parts are distributed over the entire body It is through them that herbs exert influence on pathological targets and achieve the improvement of sickness. For example, ephedra acts on the Channels of the Lung and Urinary Bladder so as to induce sweat for relieving asthma and promoting diuresis. As noted above, clinical applications of acupuncture are also guided by the theory of Channels and Collaterals.

In summary, while the nature or property of each herb in TCM may be assigned as Yin or Yang, and to one of the Five Elements, they act through Channels and Collaterals and are mediated via Qi, Blood and Fluid to yield therapeutic effects on targets, such as Viscera and Bowels. Pathogenic factors may be disguised as decoys through the very same systems of Channels and Collaterals to adversely affect the functions of Viscera and Bowels and thus cause sickness.

III. The Patenting of Herbal Compositions in the United States

U.S. Patents have been issued for herbal compositions used for the treatment of various diseases and other health-related problems afflicting mammals, including humans. For example, herbal compositions which include *Paeonia suffuticosa* have been found useful for treating viral infections, including infection from herpes and polio virus (U.S. Pat. No. 5,411,733).

Ocular inflammation can be treated with a pharmaceutical composition containing the plant alkaloid tetrandrine (U.S. Pat. No. 5,627,195). U.S. Pat. No. 5,683,697 discloses a pharmaceutical composition having anti-inflammatory, anti-fever, expectorant or anti-tussive action, wherein the composition includes plant parts from the species *Melia, Angepica, Dendrobium, Impatiens, Citrus, Loranthus, Celosia, Cynanchum* and *Glehnia*. An herbal formulation comprising extracts of the roots, rhizomes, and/or vegetation of *Alphinia, Smilax, Tinospora, Tribulus, Withania* and *Zingiber* has been found to reduce or alleviate the symptoms associated with rheumatoid arthritis, osteoarthritis, and reactive arthritis and to reduce the production of proinflammatory cytokines (U.S. Pat. No. 5,683,698). Compositions containing talc, silkworm excrement, and the ingredients of twelve different herbs have been shown to be effective in reducing inflammation, pain, and fever in mammals (U.S. Pat. No. 5,908,628).

Patents have also been issued for herbal compositions which find use in the treatment of cancer and cancer-related health problems. For example, U.S. Pat. No. 5,437,866 discloses a composition comprising a mixture of herbs, including species of *Scutellaria barbata*, as well as their extracts, which is used to ameliorate the effects of malignancy in humans. U.S. Pat. No. 5,665,393 discloses various herbal compositions which include *Glycyrrhiza glabra* L. and *Scutellaria baicalensis* Georgi, *Rabdosia rubescens*, and *Serenoa repens* for the treatment of prostate carcinoma. Further, antitumor herbal compositions include *Astragali radix, Paeonia radix, Cinnamomi cortex, Rhemannia radi* and *Glycyrrhizae radix* for use in increasing antitumor activity of mitomycin D and doxorubicin (U.S. Pat. No. 4,613,591 and U.S. Pat. No. 4,618,495).

IV. Adverse Effects of Cancer Chemotherapy

Medical oncology has had a great impact in changing the practice of medicine in the past several decades, as curative treatments for a variety of previously fatal malignancies have been identified. However, few categories of drugs in common use have a narrower therapeutic index and a greater potential for causing harmful side effects than do the antineoplastic drugs (Calabresi and Chabner, 1996).

Anticancer agents, like many other potent drugs with only moderate selectivity, may cause severe toxicity. Common adverse effects associated with cancer chemotherapy include, but are not limited to, gastrointestinal complications (e.g., diarrhea, nausea, vomiting, anorexia and mucositis), pain, appetite loss, bone marrow/hematological complications (e.g., leukopenia, neutropenia, anemia, hemorrhage, and thrombocytopenia), fatigue and sleep disturbance.

The inventors of the present invention performed a literature search for Chinese medicinal formulations that have been used for the treatment of symptoms associated with cancer chemotherapy. TJ-14, a botanic formulation with seven herbs, was reported to potently prevent diarrhea caused by CPT-11 in cancer patients (Kase, Y, Hayakawa T, and Aburada M. et al., Jpn. J. Pharmacol. 75, 407–413 (1997); Marita M., Nagai E and Hagiwara H. et al., Xenobiotica. 23, 5–10 (1993)). The diarrhea was proposed to occur from the accumulation of SN-38, an active metabolite of CPT-11, created by intestinal microorganisms. The inventors believe that baicalin, an inhibitor of $\beta$-glucuronidase, is the active ingredient in TJ-14 that alleviates diarrhea caused by CPT-11 (Kase, Y, Hayakawa T, and Aburada M. et al., Jpn. J. Pharmacol. 75, 407–413 (1997); Marita M., Nagai E and Hagiwara H. et al., Xenobiotica. 23, 5–10 (1993); Takasuna K, Takehiro H, Hirohashi M, et al., Cancer Chemother Pharmacol. 42:280–286 (1998); Takasuna K, Takehiro H, Hirohashi M, Kato M, et al., Cancer Res. 56:3752–3757 (1996)). Therefore, several Chinese herbal formulations containing the root of *Scuellaria baicalensis* Georgi, which is rich in baicalin, were evaluated. Among several formulations examined in the laboratory, the inventors chose PHY906. This specific formulation was established more than 1500 years ago for the treatment of diarrhea, abdominal spasms, fever, headache, vomiting, nausea, extreme thirst, and subcardial distention (Shang Han Lun of the Han Dynasty; Hong-Yen Hsu and Chau-Shin Hsu, Commonly used Chinese Herb Formulas with Illustrations, Oriental Healing Art Institute, California, (1980)). PHY906 consists of four herbs with proportion of *Scutellariae baicalensis* Georgi (scute), *Paeonia lactiflora* pall (white peony root), *Glycyrrhizae uralensis* Fisch (licorice) and the fruit of *Fructus ziziphi* (date) mixed in the proprotions 1.5:1.0:1.0:1.0 by dry weight, respectively. It should be noted that each herb possesses a distinct pharmacological profile that includes anticancer and antiviral activity, hematological and immunological stimulation, analgesic activity, vasodilation, liver protection, antioxidation, and appetite improvement, as shown in Table 1.

TABLE 1

Putative Biological Activities of Individual Herbs in the PHY906 Formulation.

| | Anti-Cancer | Immuno-Modulation | Anti-Bacteria | Anti-Inflammatory | Nervous System | Others |
|---|---|---|---|---|---|---|
| *Scuellaria baicalensis* Georgi | + | + <br> ↑↓ lymphocyte & macrophage activity bifunctional | + | + | − | antiviral, antibacterial antidiarrhea, diuretic, vasodilation, ↓ lipid, anticoagulation, antioxidant, antiemetic, liver protection |
| *Paeonia lactiflora* pall | + | + <br> ↑↓ macrophage activity bifunctional modulator | + | + | + <br> analgesic | vasodilation, liver protection, diuretic anticoagulation, ↓ intestine movement |
| *Fructus ziziphi* | + | + <br> anti IgE action | − | − | + <br> ↑ sleep | liver protection, muscle endurance, improve appetite |
| *Glycyrrhiza uralensis* Fisch | + | + <br> ↑ macrophage activity <br> ↑ interferon & ↑ IL-1 <br> ↑ lymphocyte <br> ↑ interferon & ↑ IL-2 <br> ↑ NK activity <br> ↓ IgE | + | + | + <br> analgesic | Antidiuretic <br> ↓ intestine movement <br> ↓ lipid (LDL, TC) <br> antioxidant <br> antiviral <br> anticoagulation <br> anticomplement |

↑: increase
↓: decrease

TABLE 1-continued

Putative Biological Activities of Individual Herbs in the PHY906 Formulation.

| | Anti-Cancer | Immuno-Modulation | Anti-Bacteria | Anti-Inflammatory | Nervous System | Others |
|---|---|---|---|---|---|---|

↑↓: decrease or increase
+: effect
−: no effect

Until now, PHY906 has been prescribed as a single medicine only, rather than in combination with synthetic drugs. However, it is conceivable that one of the documented uses of PHY906 might actually be useful in alleviating the side effects induced by chemotherapy. Although some of the major chemical components in each of the four herbs of PHY906 have been identified, and their pharmacological activities have been examined (Chinese Botany Shanghai Science and Technology Publishing Company (1999); Huang, H-C, Wang, H-R, and Hsieh, L-M., Eur J of Pharmacol 251:91–93 (1994); Lin, C-C and Shieh, Am J Chinese Med 1:31–36 (1996); Tang, W. and Eisenbrand, G., Chinese Drugs of Plant Origin: Chemistry, Pharmacology and Use in Traditional and Modern Medicine pp. 919–929. Springer-Verlag Press, New York, (1992)), the biological properties of PHY906 may not be fully predicted by the identified ingredients.

SUMMARY OF THE INVENTION

The inventors of the present invention have unexpectedly discovered that the herbal composition PHY906 can be used in various methods for increasing the therapeutic index of one or more chemotherapeutic compounds and for modulating hematopoietic activity. The methods disclosed herein can be used to improve the quality of life for chemotherapy patients and to increase the dosage of chemotherapeutic agents because of the decreased toxicity of the agents when they are administered with PHY906.

This invention provides the herbal composition PHY906 combined with a pharmaceutically acceptable carrier and optionally including one or more chemotherapeutic compounds or antiviral agents. The four plant species which are chosen to make a particular formulation of PHY906 are each selected from one of four different groups of herbs: Scutellaria, Licorice, Peony Alba and Ziziphi Fruit. The herbs are chosen so as to obtain one or more of the desirable attributes of PHY906, wherein such attributes include, but are not limited to, increasing the therapeutic index of one or more chemotherapeutic compounds, enhancing the antitumor activity of one or more chemotherapeutic compounds or enhancing the antiviral activity of one or more antiviral agents, modulating hematopoietic activity, modulating hematological and immunological activity, and improving the quality of life of a mammal undergoing chemotherapy or antiviral therapy.

Chemotherapeutic compounds or agents encompassed by this invention include, but are not limited to, those useful for treating cancer, parasitic infections, and microbial infections.

Antiviral compounds or agents encompassed by this invention include those that are useful for treating viral infections, diseases, or conditions.

The compositions and methods of the present invention are useful for treating any mammal. More specifically, the methods of the present invention are useful for treating humans.

This invention further provides compositions which include a pharmaceutically acceptable carrier; material or chemical from a plant species of each of the following genera of herbs: Scutellaria, Glycyrrhiza, Ziziphus and Paeonia; and one or more chemotherapeutic compounds. Preferably, the composition comprises a pharmaceutically acceptable carrier, an herbal preparation comprising Scutellaria, Glycyrrhiza, Ziziphus and Paeonia, and a chemotherapeutic formulation comprising one or more chemotherapeutic or antiviral agent. More preferably, the herbal preparation comprises material or chemical from Scutellaria, Glycyrrhiza, Ziziphus and Paeonia. Most preferably, this invention provides such compositions which include Scutellaria baicalensis, Glycyrrhiza uralensis, Ziziphus jujuba, and Paeonia lactiflora.

The herbal compositions of the present invention are particularly useful with cancer chemotherapies, such as, but not limited to, treatment with an irinotecan formulation (CPT-11, CAMPTOSAR®), 5-fluorouracil (FU or 5-FU), VP-16, beta-L-Dioxolane-cytidine (L-OddC), leucovorin (LV), and combinations thereof, such as but not limited to FU/LV and CPT-11/FU/LV.

The herbal compositions of the present invention are particularly useful with antiviral therapies. Preferably, the herbal compositions are administered with antiviral agents useful for treating AIDS. More preferably, the herbal compositions are administered with antiviral agents selected from the group consisting of AZT, D4T, and DDI.

The present invention provides methods for increasing the therapeutic index of cancer therapeutic compounds used in the treatment of cancer. The present invention also provides methods for increasing the therapeutic index of antiviral agents used in the treatment of antiviral diseases. More specifically, the present invention provides such methods which include administering one or more anticancer or antiviral agent in combination with a therapeutically effective amount of a composition comprising a pharmaceutically acceptable carrier and material or chemical from, or herbal preparation comprising a plant species of each of the following genera of herbs: Scutellaria, Glycyrrhiza, Ziziphus and Paeonia. The methods of the present invention provide the use of material or chemical from, or herbal preparation comprising such herbs which is in the form of a granulated extract from a concentrated aqueous liquor. Such compositions can be in an ingestible form, such as, but not limited to, powders, capsules, liquids and tablets. Alternatively, the methods of the present invention use such compositions in the form of a suppository.

The present invention also provides methods of treating diseases in mammals in need of such treatment which includes administering a therapeutically effective amount of a composition comprising a pharmaceutically acceptable carrier; material or chemical from, or herbal preparation comprising a plant species of each of the following genera of herbs: Scutellaria, Glycyrrhiza, Ziziphus and Paeonia; and one or more chemotherapeutic compounds.

The present invention further provides methods of treating diseases in a mammal in need of such treatment which includes administering a therapeutically effective amount of one or more chemotherapeutic compounds or antiviral agents and a composition which includes a pharmaceutically acceptable carrier; material or chemical from, or herbal preparation comprising a plant species of each of the following genera of herbs: *Scutellaria, Glycyrrhiza, Ziziphus* and *Paeonia*. The present invention includes such methods wherein the composition is administered before the administration of the one or more chemotherapeutic compounds. The present invention also includes such methods wherein the composition is administered after the administration of the one or more chemotherapeutic compounds.

The present invention provides methods of modulating hematopoietic activity for the treatment of a disease by administering to a mammal in need of such treatment a therapeutically effective amount of a composition consisting essentially of a pharmaceutically acceptable carrier and material or chemical from or herbal preparation comprising a plant species of each of the following genera of herbs: *Scutellaria, Glycyrrhiza, Ziziphus* and *Paeonia*. The present invention provides such methods wherein the material or chemical from the herbs is in the form of a granulated extract from a concentrated aqueous liquor. Specifically, the present invention provides such methods wherein the composition is in an ingestible form, such as, but not limited to, powders, capsules, liquids and tablets. Alternatively, the present invention provides such methods wherein the composition is in the form of a suppository.

The present invention also provides methods of improving the quality of life of a mammal undergoing chemotherapy or antiviral therapy which comprises administering a therapeutically effective amount of one or more chemotherapeutic compounds and a composition comprising:

i) a pharmaceutically acceptable carrier;

ii) material or chemical from a plant species of each of the following genera of herbs: *Scutellaria, Glycyrrhiza, Ziziphus* and *Paeonia*.

The present invention contemplates administering a chemotherapeutic formulation comprising one or more chemotherapeutic agents in combination with a composition comprising a pharmaceutically acceptable carrier and an herbal preparation comprising a plant species of each of the following genera of herbs: *Scutellaria, Glycyrrhiza, Ziziphus* and *Paeonia*.

The present invention also contemplates administering a antiviral formulation comprising one or more antiviral agents in combination with a composition comprising a pharmaceutically acceptable carrier and an herbal preparation comprising a plant species of each of the following genera of herbs: *Scutellaria, Glycyrrhiza, Ziziphus* and *Paeonia*.

The present invention uses the disclosed herbal compositions for increasing the antitumor activity of chemotherapeutic agents, increasing the antiviral activity of antiviral agents, decreasing the toxicity of the chemotherapeutic or antiviral agent, modulating the hematological and immunological activity of a mammal, and improving the quality of life of a mammal undergoing chemotherapy or antiviral therapy In one aspect, the present invention discloses a method of treatment comprising a chemotherapeutic regimen comprising one or more chemotherapeutic compounds and a composition comprising a pharmaceutically acceptable carrier and an herbal preparation comprising *Scutellaria, Glycyrrhiza, Ziziphus* and *Paeonia*. In another aspect, the present invention discloses a method of treatment comprising an antiviral regimen comprising one or more antiviral agents and a composition comprising a pharmaceutically acceptable carrier and an herbal preparation comprising *Scutellaria, Glycyrrhiza, Ziziphus* and *Paeonia*.

Further, the present invention provides a therapeutic regimen comprising one or more chemotherapeutic or antiviral compound and a composition comprising a pharmaceutically acceptable carrier and an herbal preparation comprising *Scutellaria, Glycyrrhiza, Ziziphus* and *Paeonia*.

Additionally, the present invention discloses chemotherapeutic regimens and compositions comprising three chemotherapeutic compounds, preferably, CPT-11, FU, and LV and an herbal preparation comprising *Scutellaria, Glycyrrhiza, Ziziphus* and *Paeonia* or material or chemical from a plant species of each of the following genera of herbs *Scutellaria, Glycyrrhiza, Ziziphus* and *Paeonia*. The present invention contemplates antiviral therapies comprising one or more antiviral agents.

Sequential administration of LV (100 mg/kg), CPT-11 (200 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).

Figure 9:
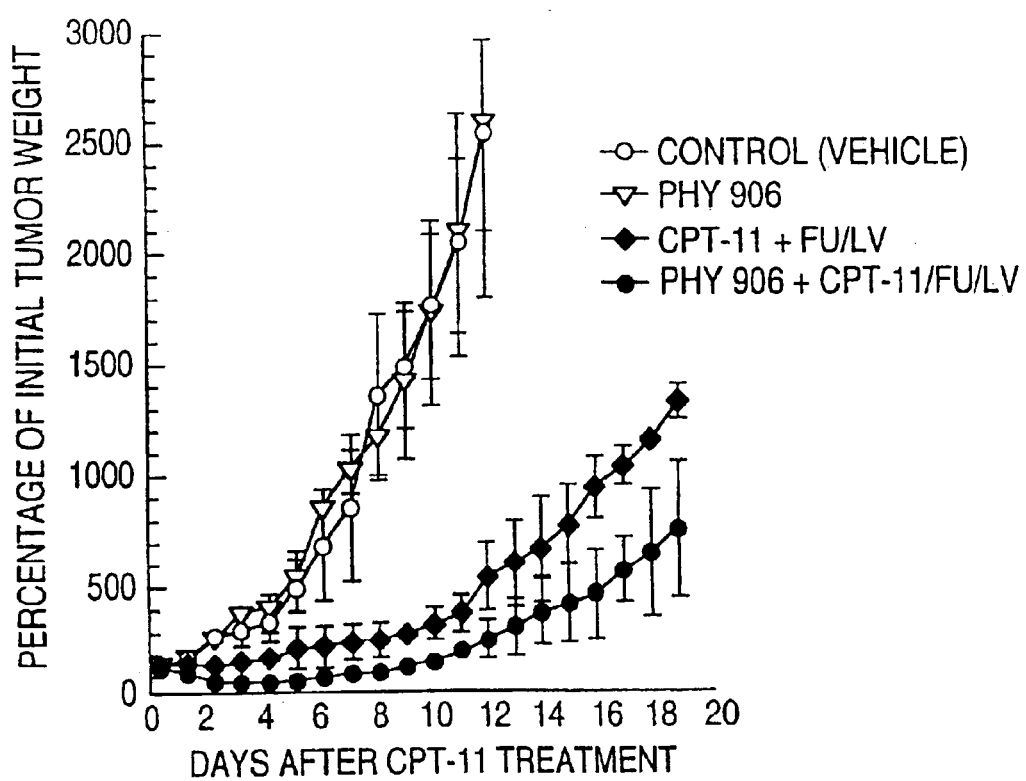

FIG. 9. Effect of PHY906 on Tumor Growth in CPT-11/FU/LV Treated BDF-1 Mice Bearing Colon 38 Tumor. Sequential administration of LV (100 mg/kg), CPT-11 (300 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).

Figure 10:
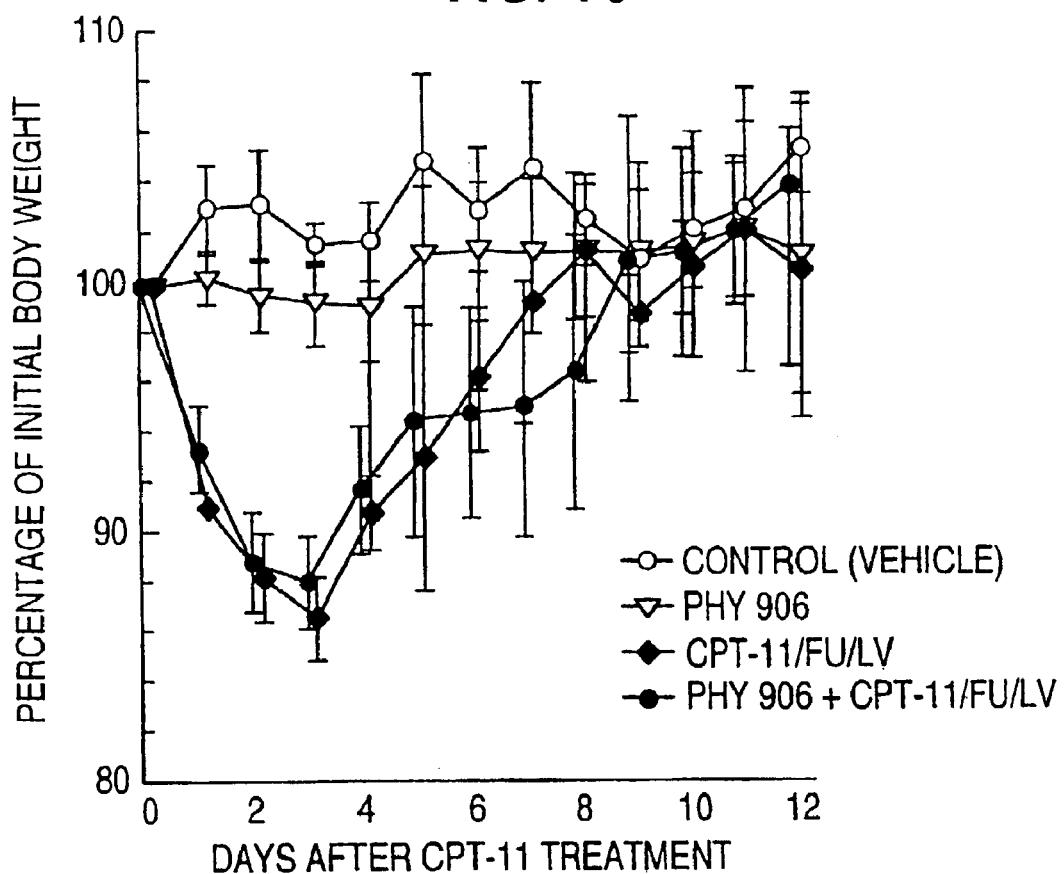

FIG. 10. Effect of PHY906 on Body Weight Change in CPT-11/FU/LV Treated BDF-1 Mice Bearing Colon 38 Tumor. Sequential administration of LV (100 mg/kg), CPT-11 (300 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).

Figure 11:
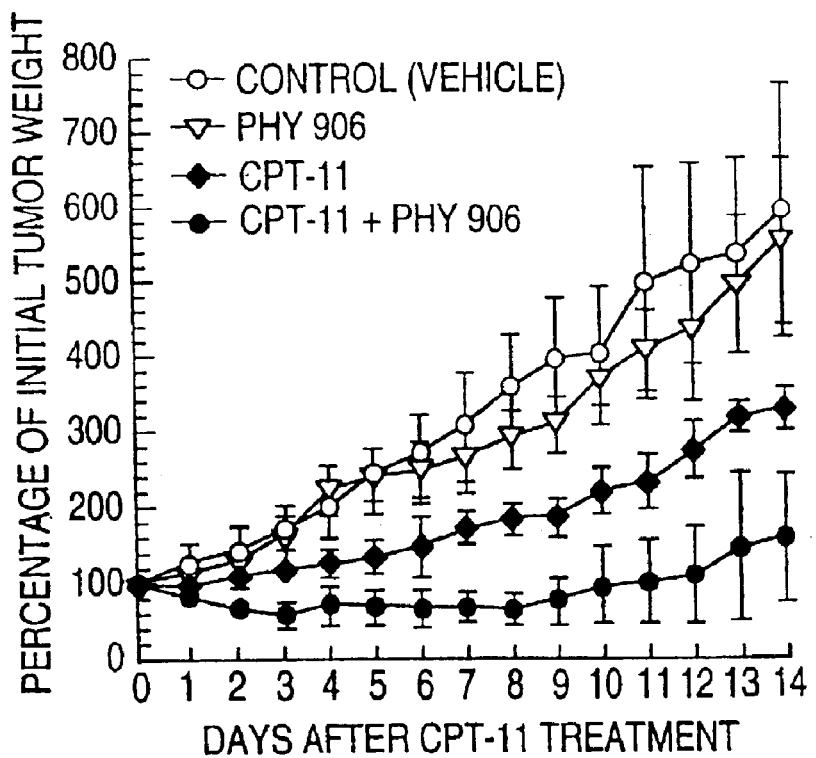

FIG. 11. Effect of PHY906 on the Tumor Growth in CPT-11 Treated NCr-Nude Mice Bearing Human HepG2 Tumor. CPT-11 (200 mg/kg) was given intraperitoneally on day 0 only. PHY906 was given orally 30 min before CPT-11 on day 0 and continued twice a day for 8 days at 500 mg/kg (N=5 in each group).

Figure 12:
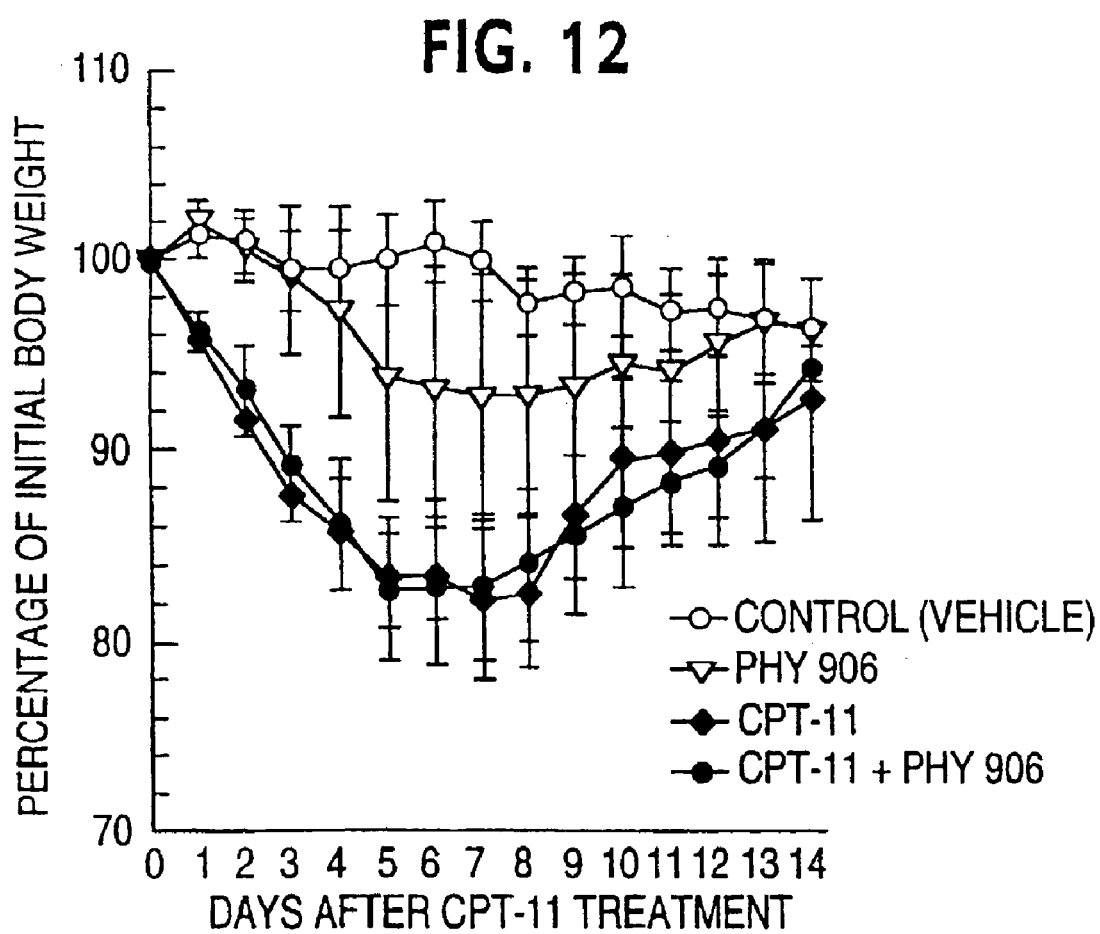

FIG. 12. Effect of PHY906 on the Body Weight in CPT-11 Treated NCr-Nude Mice Bearing Human HepG2 Tumor. CPT-11 (200 mg/kg) was given intraperitoneally on day 0 only. PHY906 was given orally 30 min before CPT-11 on day 0 and continued twice a day for 8 days at 500 mg/kg (N=5 in each group).

Figure 13:
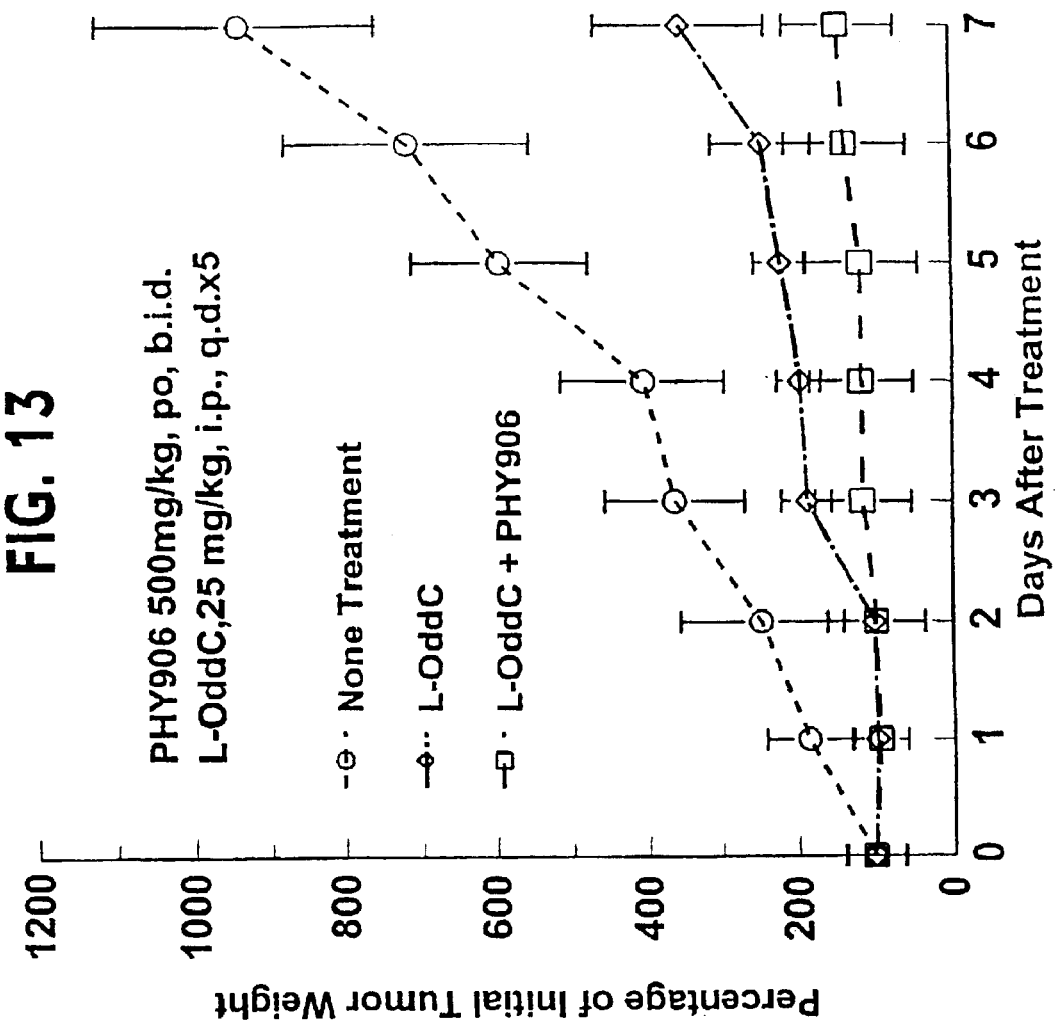

FIG. 13. Antitumor Effect of L-OddC with PHY906 on Colon 38 Bearing BDF-1 Mice. Five female BDF-1 mice (8–10 weeks old, average weight about 20 g) were injected subcutaneously with Colon 38 tumor cells. Only one dose of L-OddC (beta-L-Dioxolane-cytidine 25 mg/kg, q.d.×5) was injected intraperitoneally on day zero. PHY906 was administered orally (1 g/kg, b.i.d.) on day zero and on a daily basis until the completion of the experiment (q.d. is an abreviation for "quaque die" which means once a day, q.d.×5 means each one of five mice received the dose once a day; b.i.d. is an abbreviation for "bis in die", which means twice a day). Tumor weight was calculated as described under Materials and Methods.

Figure 14:
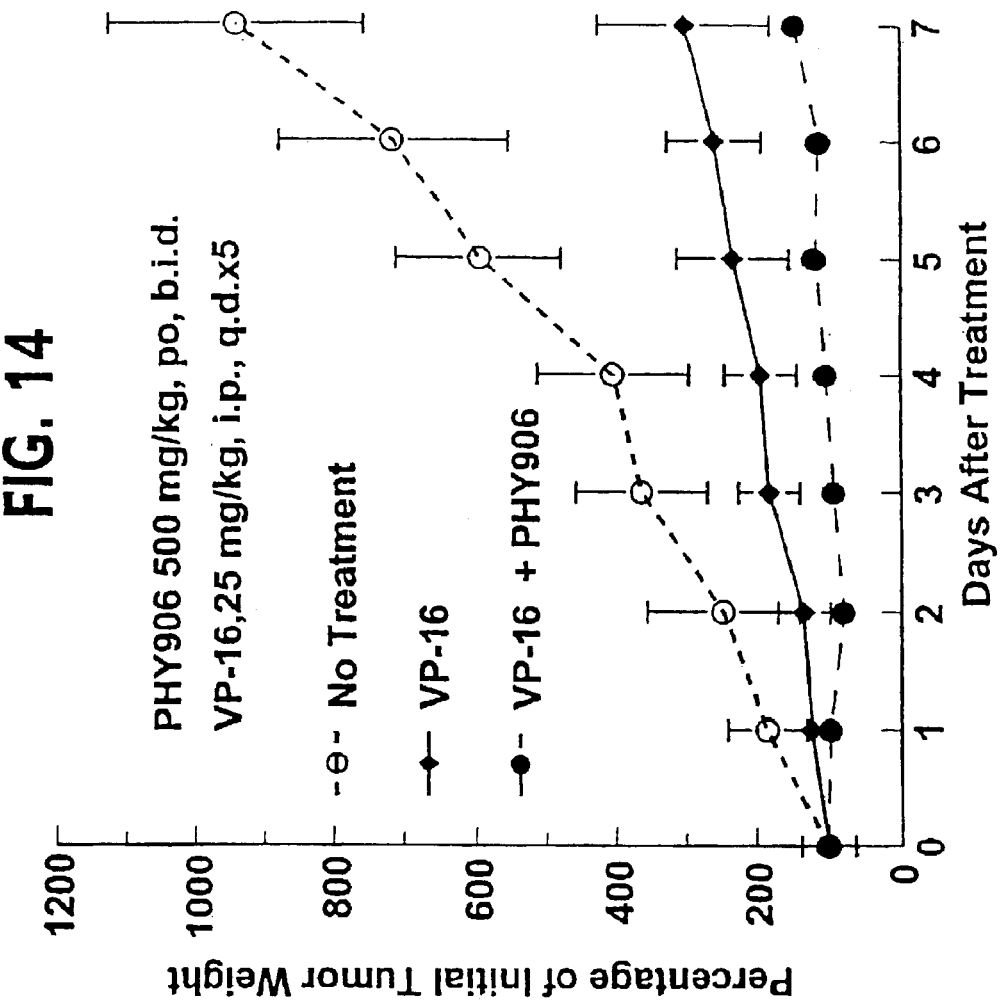

FIG. 14. Antitumor Effect of VP-16 with PHY906 on Colon 38 Bearing BDF-1 Mice. Five female BDF-1 mice (8–10 weeks old, average weight about 20 g) were injected subcutaneously with Colon 38 tumor cells. Only one dose of VP-16 (etoposide 25 mg/kg, q.d.×5) was injected intraperitoneally on day 0. PHY906 was administered orally (1 g/kg, b.i.d.) on day 0 and on a daily basis until the completion of the experiment. Tumor weight was calculated as described under Materials and Methods.

Figure 15:
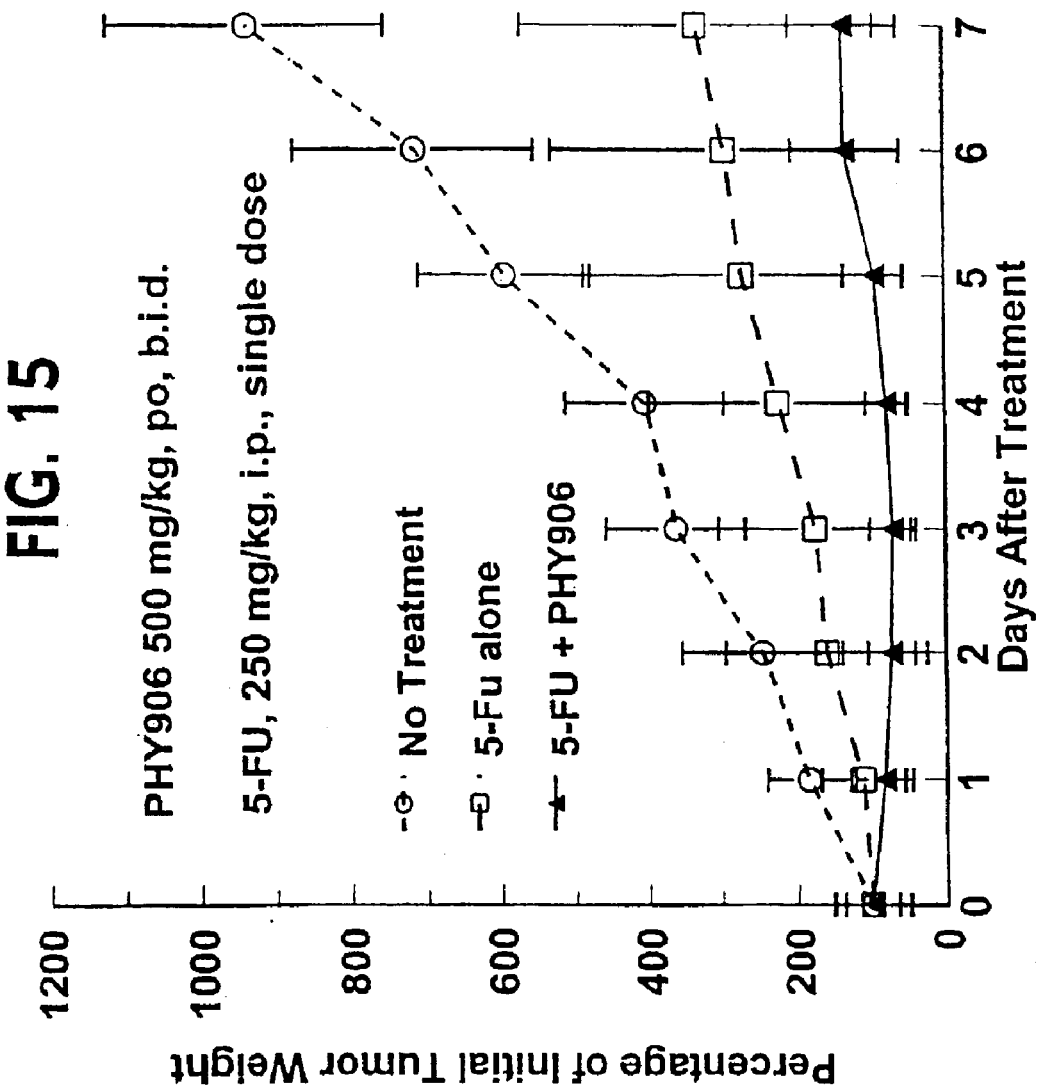

FIG. 15. Antitumor Effect of 5-Fluorouracil (FU) with PHY906. Five female BDF-1 mice (8–10 weeks old, average weight about 20 g) were injected subcutaneously with Colon 38 tumor cells. Only one dose of FU (250 mg/kg) was injected intraperitoneally on day zero. PHY906 was administered orally (1 g/kg, b.i.d.) on day zero and on a daily basis until the completion of the experiment. Tumor weight was calculated as described under Materials and Methods.

Figure 16:
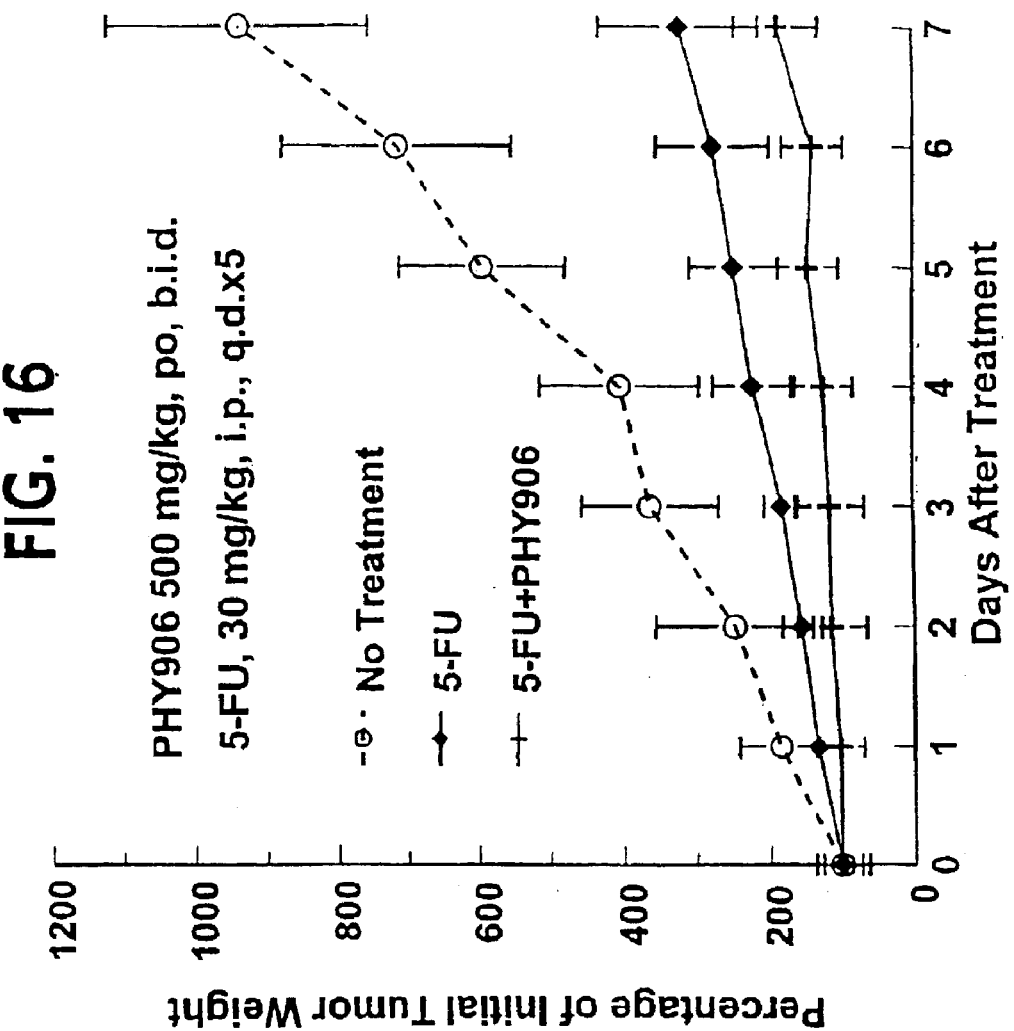

FIG. 16. Antitumor Effect of 5-Fluorouracil (FU) with PHY906. Five female BDF-1 mice (8–10 weeks old, average weight about 20 g) were injected subcutaneously with Colon 38 tumor cells. FU (30 mg/kg, q.d.×5) was injected intraperitoneally daily. PHY906 was administered orally (1 g/kg, b.i.d.) on day 0 and on a daily basis until the completion of the experiment. Tumor weight was calculated as described under Materials and Methods.

Figure 17:
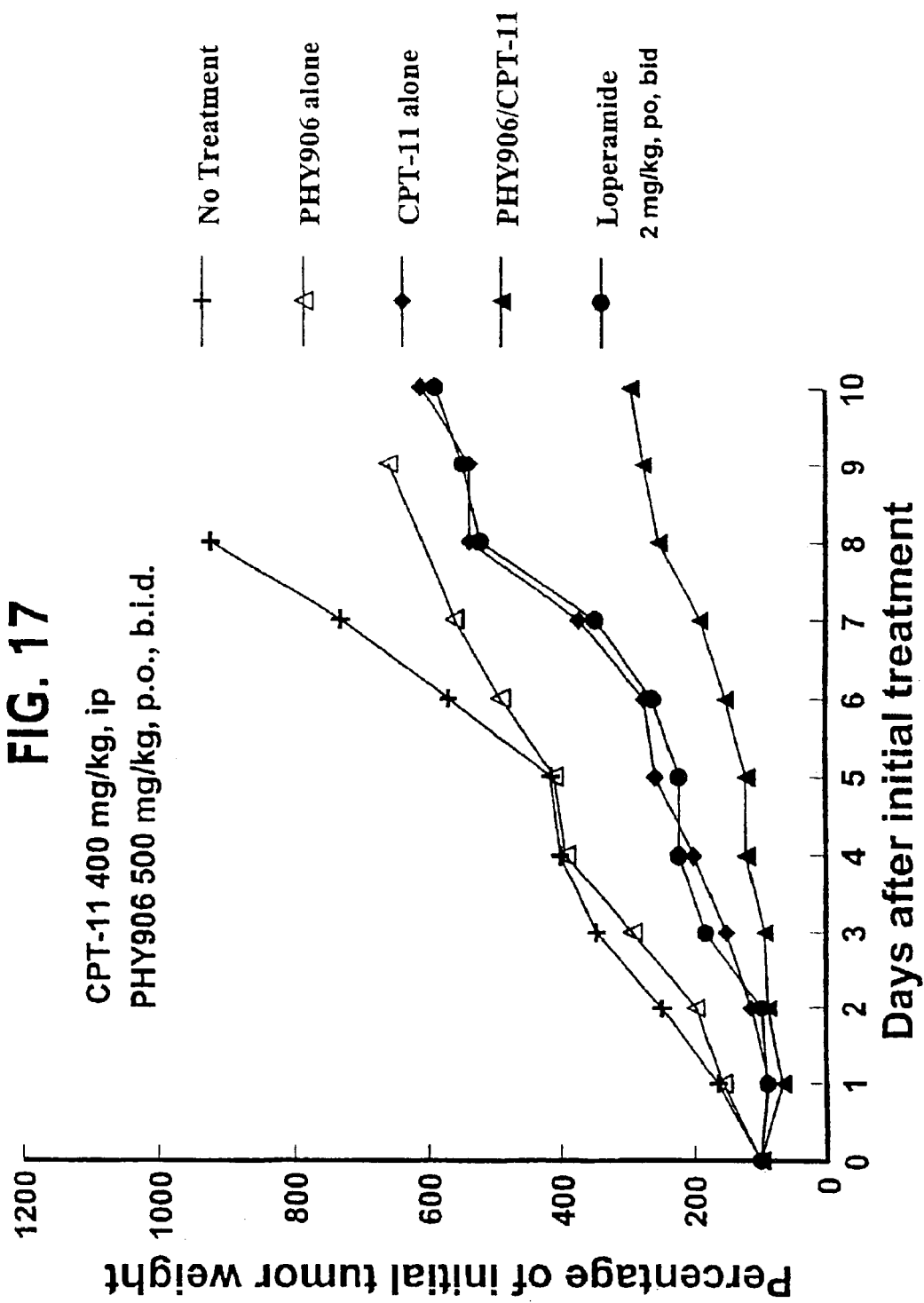

FIG. 17. Antitumor Effect of CPT-11 with PHY906 Versus Loperamide on Colon 38 Bearing BDF-1 Mice. Five female BDF-1 mice (8–10 weeks old, average weight about 20 g) were injected subcutaneously with Colon 38 tumor cells. Mice either received no treatment, PHY906 alone, CPT-11 alone, CPT-11 and PHY906, or Loperamide alone. The PHY906 and CPT-11 were administered as set forth in FIG. 3. Only one dose of Loperamide was injected peritoneally (2 mg/kg, p.o. (oral administration), b.i.d.) on day zero. Tumor weight was calculated as described under Materials and Methods.

FIGS. 18A–C. Pharmacokinetic of CPT-11/FU/LV in Plasma. PHY906-6 is the clinical batch of PHY906. SN-38 is an active metabolite of CPT-11. FUR+FUMP are nucleoside and nucleotide metabolites of FU.

FIGS. 19A–C. Pharmacokinetic of CPT-11/FU/LV in Liver. PHY906-6 is the clinical batch of PHY906. SN-38 is an active metabolite of CPT-11. FUR+FUMP are nucleoside and nucleotide metabolites of FU.

FIGS. 20A–B. Pharmacokinetic of CPT-11/FU/LV in Tumor. PHY906-6 is the clinical batch of PHY906. SN-38 is an active metabolite of CPT-11.

DETAILED DESCRIPTION OF THE PREFERRED EMBODIMENTS

Cancer chemotherapeutic agents often induce severe adverse side effects that can affect patients' quality-of-life, as well as interfere with the therapeutic regimen. The present invention is based in part on the discovery that Chinese herbal medicines in combination with standard anticancer agents is useful for reducing the adverse side effects of cancer chemotherapeutic agents and for improving the quality of life of patients undergoing chemotherapy. PHY906, a botanical formulation composed of four distinct herbs, has been used for centuries for the treatment of various gastrointestinal ailments and other illnesses in China. The present invention is based on the results of experiments performed in animal models evaluating the potential efficacy of PHY906 in relieving side effects induced by cancer chemotherapy agents in colorectal cancer patients. Specifically, the present invention is based in part on the finding that PHY906 reduces various host toxicity induced by CPT-11, FU, FU/LV, CPT-11/FU/LV, L-OddC, VP-16, or CPT-11/loperamide treatment, as well as maintaining and even potentiating the antitumor activity of chemotherapeutic agents. More specifically, PHY906 enhances the therapeutic index of CPT-11, and a triple combination of CPT-11/FU/LV by both potentiating antitumor effects of the therapeutic agents and reducing various host toxicities. These findings are not limited to one specific anticancer agent or one specific tumor model.

The present invention is also based in part on the discovery of a regimen that can be used in conjunction with various anticancer agents to lower the dose limiting toxicity and increase efficacy of the agents. This discovery is an extremely important addition to the armamentarium of treatment approaches for human cancers.

I. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, "cancer chemotherapeutic" or "cancer chemotherapeutic agent" refers to chemotherapeutic agent for the treatment of neoplastic disease or cancer.

As used herein, "chemotherapy" refers to treatment of disease by means of chemical substances or drugs.

As used herein, the term "chemotherapeutic formulation" refers to a composition comprising a chemotherapeutic agent.

As used herein, the term "extract" refers to a concentrated preparation of a vegetable or animal drug obtained by removing the active constituents therefrom with a suitable menstruum (solvent), evaporating all or nearly all the solvent and adjusting the residual mass or powder to a prescribed standard. Extracts are prepared in three forms, semiliquid or of syrupy consistency, pilular or solid, and as dry powder (see http://www.graylab.ac.uk/cgi-bin/omd?query=extract).

In one embodiment, extracts are concentrated forms of crude drugs used in a variety of solid and semisolid dosage forms (in Remington's Pharmaceutical Sciences 17th ed. (Gennaro, ed), Chapter 84, pp. 1516–1517, Mack Publishing Co, Easton, Pa. (1985)). For example, pilular (i.e., plastic masses) extracts are of a consistency where they are suitable for pill masses and are made into pills (e.g., pure *Glycyrrhiza* extract USP). Further, pilular masses are well suited for use in ointments and suppositories. Powdered extracts are better suited for powdered formulations such as capsules, powders and tablets. Further, semiliquid or extracts of syrupy consistency can be used in the manufacture of pharmaceutical preparations (Remington's Pharmaceutical Sciences, 1985).

In a related aspect, extracts can be considered solutions of active ingredients obtained by soaking or steeping preparations of vegetable or animal crude drugs in liquids (maceration) or by passing such crude drugs through porous substances (percolation) for use as a medicinal agent. Further, medicinal agents of this type may be in the form of tinctures or fluidextracts [sic] (Remington's Pharmaceutical Sciences, 1985).

In one embodiment, the extract is in tincture form. For example, tinctures may include, but are not limited to, alcoholic or hydroalcoholic solutions prepared from vegetable matter or from chemical substances. Tinctures may be made by either percolation or maceration and are traditionally assigned potency by the amount of activity of a specified weight of the drug (in grams) per 100 ml of tincture (Remington's Pharmaceutical Sciences, 1985). For example, Sweet Orange Peel Tincture contains 50 g of sweet orange peel per 100 ml of tincture.

In another embodiment, the extract is in fluidextract [sic] form. For example, fluid extracts include, but are not limited to, liquid preparations of vegetable drugs comprising alcohol as the solvent or as a preservative, or both, where traditionally each ml contains the therapeutic constituents of 1 gram of the drug that it represents. Fluidextracts can be made by percolation as a general method (Remington's Pharmaceutical Sciences, 1985).

As used herein, the term "hematological activity" refers to activity associated with blood and blood forming organs.

Technically speaking, the term "herb" refers to a small, non-woody (i.e., fleshy stemmed), annual or perennial seed-bearing plant in which all the aerial parts die back at the end of each growing season. Herbs are valued for their medicinal, savory or aromatic qualities. As the word is more generally used and as the word is used herein, an "herb" refers to any plant or plant part which has a food supplement, medicinal, drug, therapeutic, or life-enhancing use. Thus, as used herein, an herb is not limited to the botanical definition of an herb but rather to any botanical, plant or plant part used for such purposes, including any plant or plant part of any plant species or subspecies of the Metaphyta kingdom, including herbs, shrubs, subshrubs, and trees. Plant parts used in herbal compositions include, but are not limited to, seeds, leaves, stems, twigs, branches, buds, flowers, bulbs, corns, tubers, rhizomes, runners, roots, fruits, cones, berries, cambium and bark.

As used herein, an "herbal composition or formulation" refers to any composition or formulation which includes herbs, herbal plants, herbal plant parts and/or herbal extracts. Thus, as used herein, an herbal composition or formulation includes herbal preparation comprising herbal food supplements, herbal medicines, herbal drugs, and medical foods. Examples of herbal compositions include, but are not limited to, the following components: a whole plant or a plant part of a single plant species; whole plants or plant parts of multiple plant species; multiple components derived from a single plant species; multiple components derived from multiple plant species; herbal extracts; or any combination of these various components. Also contemplated are herbal compositions comprising one or more chemicals derived from a single or multiple plant species.

For a thorough review of various herbal compositions, see, for example, Kee Chang Huang, The Pharmacology of Chinese Herbs, CRC Press (1993), herein incorporated in its entirety.

As used herein, the term "immunological activity" refers to activity associated with the immune system, immunity, induced sensitivity, and allergy.

As used herein, the term "mortality rate" refers to the proportion of deaths in a population or to a specific number of the population, where mortality is defined as the death rate or ratio of the total number of deaths to the total population. For example, the 30 day mortality rate after ischemic stroke symptom onset can vary from about 13.3% (e.g., after treatment with tissue type plasminogen activator, see Albers et al., *JAMA* (2000) 283 (9):1145–1150) to greater than about 65% (e.g., hemorrhage stroke, see Mahaffey et al., *Am Heart J* (1999) 138(3 Pt 1):493–499).

As used herein, the term "Quality of life (QOL)" refers to the general well-being of an animal, especially a mammal, even more specifically a human. The QOL of an individual can be evaluated based on any one parameter, a group of two or more parameters or on a general overall evaluation or score. Examples of useful indices for evaluating QOL include, but are not limited to, those associated with sleeping patterns; eating patterns; drinking patterns; agility; mobility; skin tone; vision; hair retention/loss/growth; muscle tone; muscle mass; strength; weight; sinus health; presence, absence or degree of inflammation; feelings of discomfort; ability to accomplish specific tasks; anxiety levels; response times; ability to concentrate; memory retention; verbal ability; sound perception; presence, absence or degree of headaches; muscle spasms; nerve damage; taste; touch; smell; presence or absence of opportunistic diseases; and presence or absence of parasites.

As used herein, the term "regimen" refers to a program of treatment.

As used herein, the term "therapeutic index" refers to how selective a drug is in producing the desired effects. Therapeutic index is the ratio of $LD_{50}$ to $ED_{50}$. $ED_{50}$, the median effective dose, is the dose of a drug required to produce a specified effect in 50% of the population. $LD_{50}$ is the median lethal dose as determined in experimental animals.

II. Specific Embodiments

A. Chemotherapy.

In general, chemotherapy refers to the treatment of disease, especially neoplasms, parasitic infections and microbial diseases, with chemical agents that in some manner act on the infective organisms or tumors.

1. Cancer Chemotherapy

Introduction: Chemotherapy continues to be one of the most effective modalities for treating cancer in patients. Although quite effective, chemotherapeutic agents are also well known to adversely disrupt the quality-of-life of patients. Some commonly observed side effects include myelosuppression and immunosuppression, diarrhea, peripheral neuropathy, nausea and vomiting, fever, liver dysfunction and cardiac toxicity, etc. ("Physicians Desk Reference" (1999) Medical Economics Company). In many instances, these adverse side effects prevents patients from receiving escalating doses or additional courses of therapy, thereby comprising the efficacy of these agents. Alleviation of some or all of these side effects, without compromising the anticancer activity of chemotherapeutic agents, would not only improve the quality-of-life (QOL) of cancer patients, but also allow for a more aggressive treatment protocol, resulting in possibly improved clinical success. Currently, most supportive therapies use single agents, such as anti-emetics, anti-mucositis agents, and colony growth factors, that target individual side effects, but do not address the broad spectrum of side effects associated with cancer chemotherapy (Bleiberg H and Cvitkovic E., Eur J Cancer 32A (Suppl 3):S18–S23 (1996); Wierda D. and Matamoros M., Toxicol & Applied Pharmacol 75:25–34 (1984); Goldber R. M. and Erlichman C., Oncology 12: 59–63 (1988)).

Drugs for treating cancer include the more conventional natural products such as paclitaxel (TAXOL), the semisynthetics such as etoposide, and many newer, diverse agents such as interleukin-2 and all-trans-retinoic acid. For a comprehensive list of chemotherapeutic agents useful in treating neoplastic diseases, see, for example, Table X-1 at pages 1227–1229 of Calabresi and Chabner (1996).

The major adverse effects associated with commonly administered cancer chemotherapies are provided in Table 2.

TABLE 2

Major Adverse Effects of Cancer Chemotherapy.

| Major Adverse Health Effects | Antineoplastic Agent |
|---|---|
| Pancreatitis | VP-16, ara C |
| Alopecia | VP-16, Doxorubicin, Taxol, FU, araC |
| Cardiotoxicity | Taxol, Doxorubicin |
| Cutaneous | Doxorubicin |
| Diarrhea | CPT-11 |
| Dyspnea | ara C |
| Flush | Tamoxifen |
| Fever/Chills | VP-16, Doxorubicin |
| Hepatotoxicity | VP, Taxol, ara C, Methotrexate |
| Nephrotoxicity | Cisplatin |
| Ototoxicity | Cisplatin |
| Bone Marrow Hypoplasia | Almost all anticancer drugs |

5-Fluorouracil: The fluoropyrimidine analog, 5-fluorouracil (5-FU or FU), exhibits a broad spectrum of clinical activity. It remains one of the most active agents in the treatment of colorectal cancer both in the adjuvant and advanced disease setting, and in other GI malignancies as well (Pinedo and Peters, 1988). In addition, this agent is active against cancers of the breast, and head and neck.

Recent advances in the therapy of colorectal cancer have used biochemical modulation to selectively activate specific pyrimidine metabolic pathways. The reduced folate, leucovorin (LV), is an effective biochemical modulator and has been used in clinical treatments in combination with FU (Peters and Van Groeningen, 1991; Joulia, et al., 1999). It has been shown that the addition of exogenous folate in the form of LV enhances responses to FU in clinical trials (Calabresi and Chabner, Page 1250, 1996). The purported mechanism of interaction of LV is enhanced thymidylate synthase inhibition.

The response rate to FU in patients with advanced disease is improved from 10%–12% (FU treatment alone) to 20%–30% (FU/LV treatment).

For a detailed description of the therapeutic uses of the fluoropyrimidine analogs, including FU, see, for example, Chabner et al., 1996.

CPT-11: Irinotecan (CPT-11) is a semi-synthetic camptothecin analogue that inhibits topoisomerase I in the replicating cell. It exhibits anti-tumor activity in cancer patients who fail first-line treatment with FU/LV (Bleiberg, 1999; Stucky-Marshall, 1999).

While CPT-11 is FDA-approved as a second-line therapy for patients with advanced colorectal cancer, the observed response rates are on the order of only 10%–15%.

The main side effects associated with this agent include leukopenia, anemia, nausea/vomiting, anorexia, and diarrhea. It is, therefore, desirable to develop a modulator agent that can either enhance the efficacy of the anti-tumor activity of CPT-11 and/or alleviate some of the toxic side effects associated with CPT-11 treatment so that the overall quality of life and performance status of the cancer patient is improved.

CPT-11/FU and CPT-11/FU/LV Combination: Colorectal cancer has been reported to be the second-leading cause of death from cancer in North America. The two drugs that are currently approved by the FDA for the treatment of colorectal cancer are irinotecan (CPT-11, CAMPTOSAR®) and 5-fluorouracil (FU). FU is an antimetabolite drug, which inhibits thymidylate synthase, an enzyme required for the synthesis of DNA. FU is commonly administered with LV, a reduced folate that increases the affinity of FU for thymidylate synthase, This therapy is currently used as first-line treatment for metastatic colon cancer (Murakami K, Sakukawa, R, Sano, M, et at., Clin Cancer Res. 5:2304–2310 (1999); van der Wilt C. L, van Groeningen, C. J, Pinedo H. M, et al., J. Cancer Res. Clin. Oncol. 123:595–601 (1997)). CPT-11 is a potent inhibitor of topoisomerase I, a nuclear enzyme involved in the unwinding of DNA during replication. CPT-11 has demonstrated antitumor activity against metastatic colorectal cancer as second-line treatment after the failure of FU (Kase, Y, Hayakawa, T, Togashi, Y, et at., Jpn J Pharmacol, 75:399–405 (1997); Araki E, Ishikawa M, ligo M, et at., Jpn J Cancer Res 84:697–702 (1993); Bissery M C, Vrignaud P. Lavelle F, et at., Anti-Cancer Drugs 7:437–460 (1996); Saltz L. B, Cox J. V, Blanke C, et at., New. Eng. J. Med. 343:905–914 (2000)). Recently, FDA approved the triple combination use of CPT-11/FU/LV as the first line treatment for advanced colorectal cancer. Unfortunately, severe diarrhea has been identified as one of the dose-limiting toxicities among patients treated with this combination therapy (Saltz L. B, Cox J. V, Blanke C, et al., New. Eng. J. Med. 343:905–914 (2000); Murakami K, Sakukawa, R, Sano, M, et al., Clin Cancer Res. 5:2304–2310 (1999); van der Wilt C. L, van Groeningen, C. J, Pinedo H. M, et al., J. Cancer Res. Clin. Oncol., 123:595–601 (1997).

VP-16 (etoposide): VP-16, also known as etoposide, shows significant clinical activity against small-cell lung cancer, testicular cancer, lymphoma and leukemia (O'Dwyer, P., et al., Etoposide (VP-16-213), Current Status of an Active Anti-cancer Drug, *New Engl. J. Med.* 312:692–700 (1985)) and include neoplasms seen in Hodgkin's disease, Papillomavirus and diffuse histiocytic lymphoma.

It is believed that etoposide blocks the catalytic activity of DNA topoisomerase II by stabilizing an enzyme-DNA complex in which the DNA is cleaved and covalently linked to the enzyme. See Chen, G. L., Yang, L., Rowe T. C., Halligan, B. D., Tewey, K., and Liu, L., *J. Biol. Chem.*, 259:13560 (1984); Ross, W., Rowe, T., Glisson, B., Yalowich, J., and Liu, L., *Cancer Res.*, 44:5857 (1984); Rowe, T., Kuppfer, G., and Ross, W., *Biochem. Pharmacol.*, 34:2483 (1985), which are all herein specifically incorporated by reference.

By way of background, topoisomerases are enzymes which control the topological state of DNA. Type II topoisomerases catalyze DNA strand passage through transient double strand breaks in the DNA. The resulting change in the linking number of DNA allows these enzymes to mediate DNA interconversions, such as supercoiling and relaxation of supercoiling, catenation and decatenation, knotting, and unknotting. See Wang, J. C., *Annu. Rev. Biochem.*, 54:665 (1985) and Maxwell, A., and Gellert, M., Adv. Protein Chem., 38:69 (1986), which are herein specifically incorporated by reference.

Type II DNA topoisomerase enzymes have been shown to be involved in a number of vital cellular processes, including DNA replication and transcription, and chromosomal segregation. These enzymes, therefore, are a critical target for the action of a wide variety of anticancer drugs, including etoposide and teniposide. The key step leading to cell death may be the capability of these drugs to block the catalytic activity of DNA topoisomerase II, as noted above.

Beta-L-Dioxolane-Cytidine (OddC): Beta-L-dioxolane-cytidine [(−)-OddC] is the first nucleoside analogue with the unnatural L configuration shown to have anticancer activity (Grove et al., Cancer Res (1996) 56(18):4187–4191). This compound has been shown to have a potent antitumor activity in human prostate and hepatocellular xenograft tumor models (Grove et al., Cancer Res (1995) 55:3008–3011). Further, OddC has been shown to be effective against hyperproliferative activity in human keratinocytes in vitro (Schwartz et al., Skin Pharmacol Appl Skin Physiol (1998) 11(4–5):207–213).

This compound works by rapid translocation into cells by both equilibrative-sensitive and -insensitive nucleoside transport systems where it is incorporated into DNA of cells. DNA incorporation leads to degradation of DNA into large fragments without generation of internucleosomal laddering.

Quality of Life (QOL): Standard evaluation measures for the success of cancer treatments include, but are not limited to, changes in tumor mass and type as well as the rate and amount of tumor spreading (both locally to and distant to the tumor(s) being evaluated). One skilled in the art of chemotherapy evaluations can also determine whether a particular treatment appears to enhance a patients life expectancy and quality of life (even for those patients not responding to the usual treatments). For example, effective treatment of gastrointestinal diseases may be determined by several criteria, including, but not limited to, an enteritis score (based upon a composite score of clinical symptoms such as abdominal pain, cramping, stool guaiac and diarrhea), as well as related endpoints such as percent chemotherapy dose delivered, days of hospitalization, transfusions, intravenous fluid therapy, antimotility agents, and ability to eat.

With respect to a treatment effect, the subjective symptoms of the patient do not always coincide with the result of the test conducted by the doctor. For example, even in the case where an unfavorable test result is obtained, when the occurrence of urinary incontinence and voiding are reduced, the patient believes the treatment has worked, with the result that the quality of life (QOL) is improved. During chemotherapy the negative side-effects in the life of the patients, such as hair loss, reduction in weight, loss of appetite, fatigue, diarrhea, nausea, vomiting, etc. can be persistent and result in chronic torment, night and day, that can be unbearable to the patients, both physically and mentally. Thus, therapeutic effectiveness of methods of the present invention is meant to refer not only to partial or entire relief from the pain or reduction in tumor growth or cancer regression, but relief as a consequence of reduced or eliminated side-effects traditionally associated with treatment, with the overall result being an enhanced quality of life.

Baseline evaluations can be entered as part of the treatment protocol whereby various criteria are measured and correlated with QOL. Further, patients can report on a patient diary events such as feeling "fair" or experiencing "moderate" pain. These measures are then used during and after treatment to evaluate whether the patient feels that the quality of life has improved.

2. Chemotherapy of Parasitic Infections

Parasitic protozoa are responsible for a wide variety of infections in man and animals, and many diseases caused by parasitic protozoa are life threatening to the host. For example, malaria remains a significant health threat to humans despite massive international attempts to eradicate the disease; trypanosomiasis such as Chagas disease caused by *Trypanosoma cruzi* and African sleeping sickness caused by *T. brucei* are not uncommon in Africa and South America; and opportunistic infections in immunocompromised hosts caused by *Pneumocystis carinii, Toxoplasma gondii, Cryptosporidium* spp. are becoming increasingly significant in the developed countries.

In some protozoal diseases, such as Chagas disease, there is no satisfactory treatment; in others, drug-resistant strains of the protozoa may develop. Accordingly, there exists a continued need to identify new and effective anti-protozoal drugs. However, antiparasitic drug discovery has been, for the most part, a random and laborious process through biological screening of natural products and synthetic compounds against a panel of parasites.

Despite encouraging progress in vaccine development, chemotherapy remains the single most effective, efficient, and inexpensive means to control most parasitic infections (Tracy and Webster, Chemotherapy of Parasitic Infections, in Goodman & Gilman's The Pharmacological Basis of Therapeutics, Ninth Edition, pages 955–985, 1996). Drugs available now are especially effective in treating human infections caused by flukes and intestinal parasites. But new or better pharmaceuticals are urgently required, both to combat such systemic infections as cysticercosis, filariasis, leishmaniasis, trichinosis, and trypanosomiasis and to counteract development of drug resistance manifested especially by malaria and other protozoan parasites. Protozoan parasites develop resistance to drugs far more readily than do helminths, consistent with their more rapid proliferation in the host.

It is essential that antiparasitic drugs be safe and effective in patients. The therapeutic efficacy of antiparasitic drugs are complex and are dependent upon the host, the parasite, and the environmental factors. Thus, the best drugs and optimal dose regimens are often determined by trial and error rather than from careful pharmacokinetics and pharmacodynamic studies of patients with endemic infections. For proper evaluation, population-based chemotherapy should be instituted only after appropriate epidemiological studies divulge patterns of transmission and the relationship of age-specific prevalence and intensity of infection to disease. For optimal results, chemotherapy should be combined with other public health measures appropriate for the particular infection, environment and host population. The ideal agent for mass chemotherapy would have a broad spectrum of activity against all developmental stages of infecting parasites. It also would be safe at high therapeutic doses taken orally for one day only; be chemically stable under conditions of use; be effective as an inducer of drug resistance; and be inexpensive. At present, few available antiparasitic drugs meet these criteria.

Chemotherapeutic agents that are effective against asexual erythrocytic malarial parasites include chloroquine, quinine, quinidine, mefloquine, and halofantrine. Other drugs such as pyrimethamine, sulfonamides, sulfones, and- tetracyclines, are slower acting and less effective than the above agents, and therefore are usually used in combination with other chemotherapeutic agents. Agents such as atovaquone, chloroquine, diloxanide furoate, eflornithine, emetine and dehydroemetine, 8-hydroxyquinolines, melarsoprol, metronidazole, nifurtimox, pentamidine, quinacrine, sodium stibogluconate, and suramin are effective in treating parasitic infections including trypanosomiasis, leishmaniasis, amebiasis, giardiasis, and trichomoniasis. Lastly, infections with parasitic worms, helminthiasis, are usually treated with anthelmintic drugs such as benzimidazole, diethylcarbamazine, ivermectin, metrifonate, niclosamide, oxamniquine, piperazine, praziquantel, and pyrantel pamoate. For a review of drugs for chemotherapy of parasitic infections, see Tracy and Webster, Id.

3. Chemotherapy of Microbial Diseases

In 1936, favorable clinical results using sulfanilamide in puerperal sepsis and meningococcal infections reported by Colebrook and Kenny and Buttle and coworkers awakened the medical profession to the new field of antibacterial chemotherapy. In 1941, penicillin was mass produced and first made available for limited clinical trial. At present, at least 30% of all hospitalized patients receive one or more courses of therapy with antibiotics, and millions of potentially fatal infections have been cured.

Antibiotics are substances produced by various species of microorganisms (bacteria, fungi, actinomycetes) that suppress the growth of other microorganisms and eventually may destroy them. However, common usage extends the term to include synthetic bacterial agents, such as sulfonamides and quinolones, which are not products of microbes. Antibiotics differ in physical, chemical, and pharmacological properties; antibacterial spectra; and mechanisms of action.

The most common classification of antimicrobial agents which is based on chemical structure and proposed mechanism of action is the following: (1) agents that inhibit synthesis of bacterial cell walls; for example, the penicillins and cephalospoins, which are structurally similar, and dissimilar agents such as cycloserine, vancomycin, bacitracin, and the imidazole antifungal agents such as miconazole, ketoconazole, and clotrimazole; (2) agents that act directly on the cell membrane of the microorganism, affecting permeability and leading to leakage of intracellular compounds; these include the detergents, polymyxin and colistimethate, and the polyene antifungal agents, that bind to cell-wall sterols; (3) agents that affect the function of 30S or 50S ribosomal subunits to cause a reversible inhibition of protein synthesis; these bacteriostatic drugs include chloramphenicol, the tetracyclines, erythromycin, and clindamycin; (4) agents that bind to the 30 S ribosomal subunit and alter protein synthesis, which eventually leads to cell death; these include the aminoglycosides; (5) agents that affect nucleic acid metabolism, such as the rifamycins (e.g., rifampin), which inhibit DNA-dependent RNA polymerase, and the quinolones, which inhibit gyrase; (6) the antimetabolites, including trimethoprim and the sulfonamides, which block specific metabolic steps that are essential to microorganisms; (7) nucleic acid analogs, such as zidovudine, ganciclovir, vidarabine, and acyclovir, which inhibit viral enzymes that are essential for DNA synthesis, thus halting viral replication. (See, Chambers and Sande, Section IX Chemotherapy of Microbial Diseases: Antimicrobial Agents, in Goodman & Gilman's The Pharmacological Basis of Therapeutics, Ninth Edition, page 1029, 1996.)

Whether an antibiotic is effective in treating an infection depends on several factors. In order for an antibiotic to be effective, a sufficient concentration of the antibiotic must be achieved at the site of infection to inhibit bacterial growth. However, the concentration of the drug must remain below those that are toxic to human cells. If the concentration of antibiotic required to inhibit or kill the microorganism is greater than the concentration that can be safely achieved, the microorganism is considered to be resistant to the antibiotic. Bacteria can be resistant to an antimicrobial agent because the agent fails to reach its target, the agent is inactivated, or the target is altered. Some bacteria produce enzymes that reside at or within the cell surface and inactivate the drug. Others possess impermeable cell membranes that prevent the influx of the drug. Some bacteria are deficient in aqueous channels made up of porins that hydrophilic agents use to traverse the outer membrane of bacteria, while others lack the transport system that is required for entrance of the drug into the bacterial cell. The emergence of antibiotic resistant pathogens has led to an ever-increasing need for new drugs and new methods of treating antimicrobial diseases.

B. Antiviral Therapy

1. Viruses and Viral Diseases

A virus is a microorganism that cannot reproduce by itself. However, upon infection of a host cell, the virus utilizes the metabolic machinery of the host cell to produce more viral material. Viral infection and replication in host cells generally results in disease, whether the host is an animal or plant. Human diseases caused by viral infections include, for example, the acquired immunodeficiency syndrome (AIDS) and hepatitis. A general discussion of this field is presented in Fundamental Virology, Second Edition, (ed. B. N. Fields, D. M. Knipe, R. M. Chanock, M. S. Hirsh, J. L. Melnick, T. P. Monath, and B. Roizman, Raven Press, Ltd., New York, N.Y. 1991). Examples of a few viruses and the diseases that they cause are discussed below.

Retroviruses: Retroviruses comprise a large family of viruses that primarily infect vertebrates. Many diseases, including the induction of some tumors, are associated with retroviral infection (see Fundamental Virology, supra, pp. 645–708). Retroviruses contain an RNA genome that is replicated through a DNA intermediate. Early in the retroviral life cycle, the RNA genome is copied into DNA by the virally encoded reverse transcriptase (RT). This enzyme can use both RNA and DNA templates, thereby producing the first strand of DNA (the negative strand) from the infecting RNA genome and a complementary second strand (the positive strand) of DNA using the first DNA strand as a template. To synthesize these DNA strands, the RT utilizes cellular substrates called deoxynucleoside triphosphates (dNTP).

Human retroviruses can be grouped into the leukemia viruses (HTLV type viruses) and the immunodeficiency viruses (HIV type viruses). HTLV infection may lead to one form of leukemia. HIV infection causes acquired immuno-deficiency syndrome (AIDS). There are two related human immunodeficiency viruses, HIV-1 and HIV-2. HIV-1 is more virulent than HIV-2. Both HTLV and HIV infect peripheral blood lymphocytes (PBL).

Other animal retroviruses include feline leukemia virus (FeLV) and lentiviruses. Virulent FeLV infection generally results in fatal aplastic anemia in cats. Lentiviruses cause a variety of neurological and immunological diseases such as visna in sheep and infectious anemia in horses.

Several other viruses that infect humans, animals, and plants also depend on reverse transcriptase for replication. These include retroviruses such as the leukemia viruses known to exist in several species, including HTLV-1 in humans, as well as reverse transcriptase dependent DNA viruses, such as the cauliflower mosaic virus (a plant virus).

Viral Hepatitis: Hepatitis is a disease of the human liver. It is manifested with inflammation of the liver and is usually caused by viral infections and sometimes from toxic agents. Hepatitis may progress to liver cirrhosis, liver cancer, and eventually death. Several viruses such as hepatitis A, B, C, D, E and G are known to cause various types of viral hepatitis. Among them, HBV and HCV are the most serious.

Hepatitis B is caused by a DNA virus. It has a long incubation period of 50–160 days. It is usually transmitted by injection of infected blood or blood derivatives or by use of contaminated needles, lancets, or other instruments. Hepatitis B virus infection leads to a wide spectrum of liver injury. Moreover, chronic hepatitis B infection has been linked to the subsequent development of hepatocellular carcinoma, a major cause of death.

Hepatitis C is caused by an RNA virus. The incubation period of 6–8 weeks with about 75% of infections subclinical and giving rise to chronic persistent infection. A high percentage develop chronic liver disease leading to cirrhosis and possible heptocellular carcinoma. Hepatitis C is difficult to treat and it is estimated that there are 500 million people infected with it worldwide (about 15 time those infected with HIV).

Herpesviruses: Herpesviruses isolated from humans include, but are not limited to, herpes simplex virus 1 ("HSV-1"), herpes simplex virus 2 ("HSV-2"), human cytomegalovirus ("HCMV"), varicella-zoster virus ("VZV"), Epstein-Barr virus ("EBV"), human herpesvirus 6 ("HHV6"), herpes simplex virus 7 ("HSV-7"), herpes simplex virus 8 ("HSV-8"). Herpesviruses have also been isolated from horses, cattle, pigs (pseudorabies virus ("PSV") and porcine cytomegalovirus), chickens (infectious larygotracheitis), chimpanzees, birds (Marck's disease herpesvirus 1 and 2), turkeys and fish (see "Herpesviridae: A Brief Introduction", Virology, Second Edition, edited by B. N. Fields, Chapter 64, 1787 (1990)).

Herpes simplex viral ("HSV") infection is generally a recurrent viral infection characterized by the appearance on the skin or mucous membranes of single or multiple clusters of small vesicles, filled with clear fluid, on slightly raised inflammatory bases.

The herpes simplex virus is a relatively large-sized virus. HSV-2 commonly causes herpes labialis. HSV-2 is usually, though not always, recoverable from genital lesions. Ordinarily, HSV-2 is transmitted venereally.

Diseases caused by varicella-zoster virus (human herpesvirus 3) include varicella (chickenpox) and zoster (shingles). Cytomegalovirus (human herpesvirus 5) is responsible for cytomegalic inclusion disease in infants. Epstein-Barr virus (human herpesvirus 4) is the causative agent of infectious mononucleosis and has been associated with Burkitt's lymphoma and nasopharyngeal carcinoma. Animal herpes viruses which may pose a problem for humans include B virus (herpesvirus of Old World Monkeys) and Marmoset herpesvirus (herpesvirus of New World Monkeys).

2. Antiviral Agents

Antiviral agents include drugs such as acyclovir (ACV) which treats genital herpes to drugs that treat AIDS, for example, zidovudine (AZT) and dideoxyinosine (DDI). Examples of a few antiviral agents are discussed below.

Over the years, anti-retroviral drugs have been developed for the treatment of AIDS. Anti-retroviral drugs include, for example, Abacavir (ABC), Adefovir (ADV), Amprenavir (APV), Zidovudine (AZT), Didanosine (ddI), Zalcitabine (ddC), Stavudine (d4T), Efavirenz (EFV), Lamivudine (3TC), Saquinavir (SQV), Indinavir (IDV), Ritonavir (RTV), Delavirdine (DLV), Nelfinavir (NFV), Nevirapine (NVP). However, attempts to treat AIDS with anti-viral drugs have not been met with a desirable degree of success. Despite the high efficacy of some of the antiviral drugs, the initial in vitro/in vivo testing has been characterized by the rapid onset of variants of HIV-1 resistant to these drugs. Additionally, there is a potential for toxicity with the use of anti-viral drugs. There is a need for an effective and safe means to treat AIDS.

No local or systemic chemotherapeutic agent has been demonstrated to be effective for treating herpes simplex virus with the possible exception of topical idoxuridine (IDU) in superficial herpetic keratitis. Reports on this compound in cutaneous herpes are conflicting. Other drugs which have been employed to treat HSV include trifluorothymidine, vidarabine (adenine arabinoside, ara-A), acyclovir, and other inhibitors of viral DNA synthesis may be effective in herpetic keratitis. These drugs inhibit herpes simplex virus replication and may suppress clinical manifestations. However, the herpes simplex virus remains latent in the sensory ganglia, and the rate of relapse is similar in drug-treated and untreated individuals. Moreover, some drug-resistant herpes virus strains have emerged. Accordingly, there is also a need to develop more effective means to treat diseases associated with herpes simplex virus.

Current prevention of hepatitis B virus (HBV) infection is a hepatitis B vaccination which is safe and effective. However vaccination is not effective in treating those already infected (i.e. carriers and patients). Many drugs have been used in treating chronic hepatitis B and none have been proven to be effective, except interferon No effective immunization is currently available for hepatitis C, and hepatitis C can only be controlled by other preventive measures such as improvement in hygiene and sanitary conditions and interrupting the route of transmission. At present, the only acceptable treatment for chronic hepatitis C is interferon which requires at least six (6) months of treatment and or ribavarin which can inhibit viral replication in infected cells and also improve liver function in some people. Treatment with interferon with or without Ribavarin however has limited long term efficacy with a response rate about 25%.

C. PHY906

Introduction: PHY906 is a traditional Chinese botanical formulation composed of four herbs each of which is selected from one of four herb groups. The four herb groups are commonly known as *Scutellaria*, sometimes known as Scute, Licorice, Peony Alba and Ziziphi Fruit (Table 3). Thus, one plant species is chosen from each one of the four plant groups provided in Table 3 in order to produce the desired herbal compositions of the present invention. While particular combinations of the listed plant species are provided as examples of preferred PHY906 formulations, the compositions and methods of this invention encompass any combination of four plant species wherein a plant species is selected from each one of the four groups in Table 3. This invention encompasses any such combination of such herbs which have at least one of the biological activities or desired effects ascribed to PHY906 as described herein.

TABLE 3

Examples of Particular Species of Four Genera which can be Used to make PHY906. Common English Name of TCM Herbal Group

| Scutellaria | Licorice | Peony Alba | Ziziphi Fruit |
|---|---|---|---|
| Anemone rivularis Buch.-Ham. ex DC. | Abrus mollis Hance | Paeonia delavayi Franch. var. lutea (Delavay ex Franch.) Finet et Gagnep. | Ziziphus jujuba Mill. |
| Thalictrum omelense W. T. Wang et S. H. Wang | Glycyrrhiza aspera Pall. | Paeonia lactiflora Pall. | Ziziphus jujuba Mill. var. inermis |
| Mahonia bealei (Fort.) Carr. | Glycyrrhiza eurycarpa P.C.Li | Paeonia mairei Levi. | |
| Nandina domestica Thunb. | Glycyrrhiza glabra L. | Paeonia obovata Maxim. var. willmottiae (Stapi) Stern | |
| Scutellaria amoena C. H. Wright | Glycyrrhiza inflata Bat. | Daphne papyracea Wall. ex Steud. | |
| Scutellaria amnoena C. H. Wright var. cinerea Hand.-Mazz. | Glycyrrhiza squamulosa Franch. | Cynanchum otophyllum Schneid. | |
| Scutellaria baicalensis Georgi | Glycyrrhiza uralensis Fisch. | Codonopsis lanceolara Sieb. et Zucc. Trautv. | |
| Scutellaria baicalensis Georgi var. albiflora K. Onuma | Phlomis betonicoides Diels | | |
| Scutellaria chungtienensis C. Y. Wu | | | |
| Scutellaria hypericifolia Levl | | | |
| Scutellaria likiangensia Diels | | | |
| Scutellaria obtusifolia Hemsl. var. trinervata (Vant.) C. Y. Wu et H. W. Li | | | |
| Scutellaria regeliana Nakai | | | |
| Scutellaria regeliana Nakai var. ikonnikovii (Juz.) C. Y. Wu et H. W. Li | | | |
| Scutellaria rehderiana Diels | | | |
| Scutellaria tenax | | | |

TABLE 3-continued

Examples of Particular Species of Four Genera which can be Used to make PHY906. Common English Name of TCM Herbal Group

| Scutellaria | Licorice | Peony Alba | Ziziphi Fruit |
|---|---|---|---|
| W. W. Smith var. patentipilosa (Hand.-Marz.) C. Y. Wu | | | |
| Scutellaria viscidula Bunge | | | |

This herbal formula has been long used in Asia to treat a variety of ailments such as cardiac distention, abdominal spasms, fever, headache, vomiting, retching, thirst and mucous-like stool (Hani Oka and Taki No, 1998).

A preferred formulation of PHY906 is provided in Table 4.

TABLE 4

Herbal Ingredients of TCM Formula PHY906.

| Scientific Name | Percentage | Common Name | Traditional Use |
|---|---|---|---|
| Scutellaria baicalensis | 33.3 | Scute Baical Skullcap Root | Used to reduce capillary permeability; to reduce inflammation: to treat enteritis and dysentery; increase the secretion of bile to treat jaundice; to relieve muscle spasms to treat coughing; to expel parasites. |
| Glycyrrhiza uralensis | 22.2 | Licorice Root | Used to moisten the lungs and stop coughs; to relax spasm and stop pain; to moderate the action of herbs: to reduce fire and release toxins. |
| Ziziphus jujuba | 22.2 | Date | Has diuretic and strengthening effects |
| Paeonia lactiflora | 22.2 | White Peony Root | Used to suppress and soothe pain: to soothe ligaments and purify the blood |

An alternative formulation of PHY906 has the herbs *Scutellaria*, *Glycyrrhiza*, *Ziziphus*, and *Paeonia* in the following relative proportions: 4/14:3/14:4/14:3/14, respectively.

While specific ratios of the herbs of PHY906 are provided as examples, the compositions and methods of this invention encompass any ratios of the four herbal components which have the desired biological activity as described herein.

Currently, both gelatin capsules and granule pouches of PHY906 are produced by Sun Ten Laboratories, Inc., in Irvine, Calif. (a sister company of Sun Ten Pharmaceutical Co. Ltd. in Taiwan) using the formulation provided in Table 4. This formulation of PHY906 has been distributed and sold as a dietary supplement since 1983 by Brion Herbs Corporation (12020 B Centralia Road, Hawaiian Garden, Calif., 90716).

Production: A brief review of a process which can be used for producing PHY906 is provided. First, the proper ratios of the ingredients of the herbal raw materials are placed in a jacketed reactor and extracted with water at an elevated constant temperature with mixing. The ratios are set forth in the Manufacturing Instruction reproduced from Master Formula Record. The solid materials are then separated from the liquid with a 120-mesh screen. The filtrate is collected and then concentrated by evaporating the water under reduced pressure. The concentrated liquor is spray dried at an elevated temperature to yield dry powder which is then processed to yield granulated powder. This bulk substance is then formulated into the desired dosage form.

Process controls are utilized to ensure the uniformity and integrity of the product. Such-process controls include, but are not limited to, checking the volume of the process liquor, HPLC determinations to establish Chemical Fingerprintings to verify identity of the raw materials, and inspections and tests of intermediate and final products. Accepted Quality Level (AQL) Limits are established for each conducted analysis and for each step of the manufacturing and control of production.

All of the components used in the production process are assigned a specific lot number in the Production Instruction Record. Quality control records are reviewed before a batch is released.

Purified marker substances are used for identification and quality control of the raw materials as well as the herbal substances. Table 5 lists the marker substances of each raw material used in the preparation of PHY906 herbal substance.

TABLE 5

Marker Substances for Herbal Ingredients of PHY906

| Herb | Origin of Herb Producing Place | Marker Substance |
|---|---|---|
| Scutellaria baicalensis Georgi. | Shang Xi Province, China | Baicalin |
| Glycyrrhiza uralensis Fisch. | Inner Mongolia, China. | Glycyrrhizin |
| Ziziphus jujuba Mill. | Hebei/Shangtong Province, China | Chelidonic Acid |
| Paeonia lactiflora Pall. | An Hwei Province, China | Paeoniflorin |

D. Pharmaceutical Formulations

The compositions of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, the type of concurrent treatment, if any, the frequency of treatment, and the nature of the effect desired.

The pharmaceutical formulation for systemic administration according to the invention may be formulated for enteral, parenteral, or topical administration. Indeed, all three types of formulations may be used simultaneously to achieve systemic administration of the active ingredient.

The present invention further provides compositions containing one or more agents which treat various types of cancer and/or modulate hematopoietic activity, such as the immunodulation of tuberculosis (T.B.), natural killer cells (NK), monocytes, and dendritic cells.

While individual needs vary, determination of optimal ranges of effective amounts of each component is within the skill of the art.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action.

PHY906 can be used in the form of a medicinal preparation, for example, in solid, semi-solid or liquid form which contains PHY906, as an active ingredient, in admixture with an organic or inorganic carrier or excipient suitable for external, enteral, or parenteral applications. The active ingredient may be compounded, for example, with the usual non-toxic pharmaceutically acceptable carriers for tablets, pellets, capsules, suppositories, solutions, emulsions, suspensions, and any other form suitable for use. Formulations of the present invention encompass those which include talc, water, glucose, lactose, gum acacia, gelatin, mannitol, starch paste, magnesium trisilicate, corn starch, keratin, colloidal silica, potato starch, urea, and other carriers suitable for use in manufacturing preparations, in solid, semisolid or liquid form and in addition auxiliary, stabilizing, thickening and coloring agents, and perfumes may be used.

For preparing solid compositions such as tablets or capsules, PHY906 is mixed with a pharmaceutical carrier (e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid preformulation composition containing a substantially homogeneous mixture of PHY906, or a non-toxic pharmaceutically acceptable salt thereof. When referring to the preformulation compositions as substantially homogenous, it is meant that the active ingredients are dispersed evenly throughout the composition so that the composition may be readily subdivided into equally effective unit dosage forms such as tablets, pills and capsules. This solid preformulation composition is then subdivided into unit dosage forms of the type described above containing an effective amount of the composition of the present invention, preferably in capsules.

The tablets or pills containing PHY906 can be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol, and cellulose acetate.

The liquid forms, in which PHY906 may be incorporated for administration orally or by injection, include aqueous solution, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

For buccal administration, the compositions of the present invention may take the form of tablets or lozenges formulated in conventional manners.

PHY906 may also be formulated for parenteral administration by injection, which includes using conventional catheterization techniques or infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulating agents such as suspending, stabilizing, and/or dispersing agents. Alternatively, the active ingredients may be in powder form for reconstitution with a suitable vehicle, e.g., sterile pyrogen-free water, before use.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

In practicing the methods of this invention, PHY906 may be used alone or in combination, or in combination with other therapeutic or diagnostic agents. In certain preferred embodiments, the compounds of this invention may be coadministered along with other compounds typically prescribed for cancer chemotherapy according to generally accepted medical practice. The compounds of this invention can be utilized in vivo, ordinarily in mammals, such as humans, sheep, horses, cattle, pigs, dogs, cats, rats and mice, or in vitro.

Actual methods for preparing administrable compositions and adjustments necessary for administration to subjects will be known or apparent to those skilled in the art and are described in more detail in, for example, Remington's Pharmaceutical Science, 17th Ed., Mack Publishing Company, Easton, Pa. (1985), which is incorporated herein by reference.

"Therapeutic index" is used to designate a qualitative statement of the selectivity of a drug when a therapeutic and an untoward effect are being compared. For example, if the untoward effect is designated as T (for toxic) and the therapeutic effect as E, the therapeutic index may be defined as TD50/ED50 or a similar ratio at some other arbitrary levels of response.

E. Methods of Using PHY906

The present invention provides methods of using PHY906 in combination with therapeutics for the treatment of various diseases, conditions, or disorders.

Specifically, the present invention provides methods of using PHY906 in combination with chemotherapeutic agents for the treatment of diseases, conditions, or disorders. Preferably, the present invention provides a method of treating cancer comprising administering one or more cancer chemotherapeutic agents in combination with PHY906 to a patient. More preferably, the present invention provides a method of treating colorectal cancer comprising administering CPT-11/FU/LV in combination with PHY906.

The present invention contemplates methods of using PHY906 in combination with antiviral agents for the treatment of diseases, conditions, or disorders. Preferably, the present invention provides a method of treating a disease associated with a viral infection comprising administering one or more antiviral agents in combination with PHY906 to a patient. More preferably, the present invention provides a method of treating AIDS comprising administering one or more anti-retroviral drugs in combination with PHY906. Even more preferably, the anti-retroviral drug is selected from the group consisting of AZT, D4T, DDC, 3TC, and DDI. Most preferably, a combination comprising three antiviral drugs and PHY906 is administered to the patient. The preferred combination of three antiviral drugs include, but are not limited to, 1) D4T, 3TC, and protease inhibitor; 2) AZT, 3TC, and protease inhibitor; and 3) AZT, DDI, and protease inhibitor. The preferred protease inhibitor for treating HIV include, but not limited to, nelfinavir, indinavir, saquinavir, and ritonavir.

In one aspect of the invention, PHY906 is administered to cell lines, for example cancer or carcinoma cell lines and HIV cell lines, to evaluate the toxicity of PHY906 on different cell lines. Preferably, the cancer or carcinoma cell lines include, but are not limited to, KB, HepG2, T-cell lymphoma (CEM), Colon 38, and HCT116, and the HIV cell lines include, but are not limited to, H9 cells and MT-2 cells.

In another aspect of the invention, PHY906 in combination with one or more chemotherapeutic or antiviral agent is administered to an animal to determine whether PHY906 is effective in increasing the therapeutic index of the agent and the quality of life of the animal undergoing chemotherapeutic or antiviral therapy. Preferably, the animal is a mammal. More preferably, the mammal is a human.

The animal could be an animal model for a specific cancer or viral disease. Also, the animal could have a deficient immune system. Such animal models are well-known in the art. Naturally-occurring immunodeficient mice have been used to study the immune system, cancer, and infectious diseases, including acquired immune deficiency syndrome or AIDS. For example, the nude (NU) mouse is athymic, so T cell differentiation and maturation cannot occur. Nude mice have served for many years as host for xenografts, especially human tumors and the testing of anti-cancer drugs. The severe combined immunodeficiency syndrome (SCID) mouse appears to defectively rearrange both TCR (T cell receptor) and immunoglobulin genes and displays a severe immunodeficiency. The beige (BG) mouse carries a defect in functional natural killer cells, whereas the X-linked immunodeficient (XID) mouse has a defect in the production of B cells. In addition, crosses have been made among various strains to generate lines with more comprehensive immunodeficient pheno-types (e.g., BG/NU and BG/NU/XID).

Other laboratory animals which possess little or no immune system of their own, or which have been treated with drugs or radiation, or produced through traditional genetic development or genetic engineering to have either a suppressed immune system, a weakened immune system or a modified immune system, or no immune system at all, such as, e.g. SCID horses and other SCID animals and potentially even AIDS infected animals in which AIDS has been arrested after destruction or inactivation of the animals' immune system may be considered as laboratory animal candidates for use in the present invention (Perryman L. E., McGuire, T. C., Torbeck, R. L., and Magnuson, N. S., Clin. Immunol. Immunopath., 23(1):1–9, 1982).

Murine models to study transplacental or perinatal anti-retroviral therapy are known (Sharpe et al. (1987) Science 236: 1671–1674; Sharpe et al. (1988) Proc. Natl. Acad. Sci.

(USA) 85: 9792–9796; Sharpe et al. (1989) J. Virol. 63: 1049–1053). In addition, mammalian models utilizing rhesus monkeys have been established to study the course of non-retroviral fetal infection by simian cytomegalovirus, Venezuelan and Western equine encephalitis virus, and mumps virus (London et al. (1986) Teratology 33: 323–331; London et al. (1977) Teratology 16: 285–296; London et al. (1982) Teratology 25: 71–79; London et al. (1979) J. Inf. Diseases 139: 324–328). Infection of rhesus monkeys (*Macaca mulatta*) with simian immunodeficiency virus (SIV) closely mimics HIV-1 infection in humans. Both HIV-1 and SIV are lentiviruses with similar molecular architecture (Chakrabarti et al. (1987) Nature 328: 543–547), and both cause immunodeficiency resulting in opportunistic infections as well as central nervous system damage (Letvin et al. (1985) Science 230: 71–73).

An animal model generated to study AIDS and bone marrow cell differentiation has been reported in which human lymphocytes are transiently proliferated upon coen-grafting human fetal liver, thymus, and lymph nodes into SCID mice to form a SCID/nu mouse (McCune et al. (1988) Science 241: 1632–1686). Human immune tissues in these mice are susceptible to human immunodeficiency virus (HIV) infection (Namikawa et al. (1988) Science 242: 1684–1686) and the model has recently been used to test the effectiveness of AZT in delaying the replication of the AIDS virus.

U.S. Pat. No. 6,184,436 discloses a transgenic mouse to serve as a small animal model of AIDS. The mouse comprises a transgene comprising a DNA sequence encoding HIV-1 in operable linkage with the human CD4 promoter flanked by the enhancer of the mouse CD4 gene. The mouse develops a severe AIDS disease and leads to an early death.

In a preferred embodiment, the animals treated with one or more chemotherapeutic or antiviral agents in combination with PHY906 are evaluated for weight loss and survival rate and compared to control animals which are only administered the one or more chemotherapeutic or antiviral agents. The effect of PHY906 on the antitumor or antiviral activity could also be evaluated to determine the efficacy of PHY906.

Specifically, PHY906 can be evaluated as a modulator of antiviral therapy, such as AIDS. Any of the animal models for AIDS described above can be used. The first step involves determining the maximum tolerable dose of antiviral agent or combination of antiviral agents to administer to healthy animals by evaluating the weight loss of the animals. The second step involves administering the antiviral agent or agents in combination with PHY906 to the animals diagnosed with AIDS. The weights of the animals are evaluated and compared to control animals that did not receive PHY906 over the course of the treatment. Also, the hematological toxicity of the combination of PHY906 and antiviral agent or agents are evaluated by determining the red blood cell count or platelet count. The white blood cell counts of the animals are evaluated to determine the effectiveness of the combination of PHY906 and antiviral agent or agents in treating the animal of AIDS. The results of each assay are compared to those of control animals that are not given PHY906.

In light of the foregoing general discussion, the specific examples presented below are illustrative only and are not intended to limit the scope of the invention. Other generic and specific configurations will be apparent to those persons skilled in the art.

EXAMPLES

Materials and Methods

CPT-11 (irinotecan, CAMPTOSAR®) was purchased from Pharmacia & Upjohn Co (Kalamazoo, Mich. 5-Fluorouracil (FU or FU), folinic acid (leucovorin, LV), loperamide, *E. coli* beta-glucuronidase, methylene blue, and phenolphthalein glucuronidate were purchased from Sigma, Co. (St. Louis, Mo.). MEME medium was prepared at the Yale University Cancer Center, according to the standard procedures. RPMI 1640 medium was purchased from JRH Co. Kanamycin, pancreatin, and trypan blue were purchased from Gibco Co. (Grand Island, N.Y.). PHY906, PHY-915, PHY-14ST, and PHY-15ST botanical preparations were provided by Sun Ten Pharmaceutical Inc. (Taipei, Taiwan). PHY-14ST, previously called TJ-14ST, consists of seven herbs: *Pinelliae ternata* Breit., *Scuellaria baicalensis* Georgi, *Coptis chinensis* Franch, *Glycyrrhiza uralensis* Fisch, *Fructus ziziphi*, *Panax ginseng* C. A. Mey ., and *Zingiber officinale* Rosc. PHY-15ST, previously called TJ-15ST, consists of *Pueraria lobata* Ohwi, *Coptis chinensis* Franch, *Scuellaria baicalensis* Georgi, and *Glycyrrhiza uralensis* Fisch. PHY-915 consists of five herbs: *Panax ginseng* C. A. Mey., *Zingiber officinale* Rosc., *Atractylodes macrocephala* Koidz, *Saposhnikovia divaricata* Schischk, and *Citrus reticulala* Blanco Preparation of herbal extract from dry powder: One gram of (A) PHY906 dry powder, containing either 50% (research batch) or 10% (clinical batch) starch excipient; or (B) PHY-915, PHY-14ST, or PHY-15ST herbal formulations, containing unknown amounts of excipient, was added to 10 ml of 80° C. $H_2O$ and incubated at 80° C. for 30 minutes. The supernatant was separated from the debris by centrifugation (2060 g, 15 min) and used immediately. The concentration of PHY906 supernatant is calculated as either 50 mg/ml (from research batch) or 90 mg/ml (from clinical batch), based on the dry weight of aqueous extract of raw herbs. The concentrations of other herbal formulations were considered as 100 mg/ml, based on dry weight of the powder. The supernatant was sterilized using a 0.45 μm sterile Acrodisc filter (Gelman Sciences) for growth inhibition studies in tissue culture.

Mice: Female BDF-1 mice (4–6 weeks old) were purchased from Charles River Laboratories (Wilmington, Mass.). Male athymic NCr nude mice (4 weeks old) were purchased from Taconic Farms (Garmantown, N.Y.). Both kinds of mice weighing between 16 g and 20 g were used for this study.

Anti-Tumor Studies: Murine Colon 38 ($1-2 \times 10^6$ cells in 0.1 ml PBS) or human HepG2 cells ($1-2 \times 10^6$ cells in 0.1 ml PBS) were transplanted subcutaneously into BDF1 or NCr athymic nude mice, respectively. The length and width of the tumors were measured daily with sliding calipers. The tumor weight was estimated according to the following formula (Pizzorno G, Wiegand R, Lentz S, et al., Cancer Res. 52: 1660–1665 (1992)):

Tumor weight (mg)=length (mm)×width $(mm)^2/2$.

After 10 to 14 days, mice (five animals/group) with tumor weights ranging from 150–200 mg were selected for drug studies (Guo X, Lerner-Tung M, Chen H X, et al., Biochem Pharmacol 49:1111–1116 (1995)). Mice were sacrificed when the tumor size reached 10% of body weight. PHY906 was administered orally either alone or with anti-cancer chemotherapeutic agents. The effect of PHY906 on antitumor efficacy and the reduction of toxicity by the agents were evaluated. CPT-11 was given intraperitoneally (i.p.) 30 min after PHY906 administration with the selected dose. The regimen of FU/LV combination therapy was given as follows:

(A) treatment with FU/LV alone: first dose of LV (50 mg/kg, i.p.), one hour later the second dose of LV (50 mg/kg; i.p.), then immediately given FU (100 mg/kg, i.p.)

(B) treatment with FU/LV plus PHY906: first dose of LV (50 mg/kg, i.p.), followed 30 minutes later by PHY906 (500 mg/kg, orally), followed 30 min later by a second dose of LV (50 mg/kg, i.p.), then immediately by the FU dose (100 mg/kg, i.p.)

The CPT-11/FU/LV triple drug combination was giving as follows:

Group (A) CPT-11/FU/LV only: mice were given the first dose of LV (50 mg/kg, i.p.) one hour before administration of CPT-11, then immediately followed by LV (50 mg/kg, i.p.) and FU (100 mg/kg, i.p.)

Group (B) CPT-11/FU/LV plus PHY906: mice were given the first dose of LV (50 mg/kg, i.p.) 30 min before PHY906 (500 mg/kg, orally). Then 30 minutes after PHY906 administration, mice were treated with CPT-11, immediately followed by LV (50 mg/kg, i.p.) and FU (100 mg/kg, i.p.) on day 0.

The first day of treatment was defined as day 0. PHY906 was given orally twice a day (10 am and 3 pm) for either 4 or 8 days beginning on day 0. For the control group, mice were administrated a vehicle, either PBS for i.p. or $H_2O$ for p.o. (oral administration). Animals were monitored for mortality, weight loss, and tumor size daily.

Blood Cell Counts: Blood (20 μl) was taken from mice on days 0, 3, 6, 9 and 12 with micro-capillary tubes. Blood was then be diluted to 200 μl with normal saline (0.85% Sodium Chloride). WBC, RBC and platelets were counted by a BAKER SYSTEM 9100™ HEMATOLOGY ANALYZER (Biochem Immuno Systems Inc., Allentown, Pa. 18103-9562).

Cell Lines and Culture Conditions: The human HepG2 (hepatocellular carcinoma), HCT 116 (colon cancer), CEM (leukemia), and KB (oral epidermoid carcinoma) cell lines, and murine Colon 38 cell line were purchased from the American Type Culture Collection (Rockville, Md.). The HepG2 cell line was routinely grown in MEME media, supplemented with 10% fetal bovine serum (FBS) and 100 μg/ml kanamycin. Colon 38, HCT116, KB, and CEM cell lines were grown in RPMI 1640 media with 10% FBS and 100 μg/ml kanamycin. Cells were incubated at 37° C. in a humidified atmosphere of 5% $CO_2$: 95% air.

Cytotoxicity in human or mouse carcinoma cell lines: Cell growth inhibition was measured using the methylene blue uptake assay. Cancer cells ($1\times10^4$) were seeded into a 24-well plate in either 1 ml of MEME medium or RPMI1640 with 10% FBS and 100 μg/ml kanamycin on day 0. The freshly prepared and sterilized PHY906 extract was added to cells on day 1, at various concentrations, and incubated at 37° C. for 3 days. The medium was then removed, and the cell layer was stained for 30 min with 0.3 ml of 0.5% (w/v) methylene blue solution (in 50% ethanol). The plates were washed 3 times with tap water, dried, and the cell layer was lysed with 1 ml of 1% Sarkosyl solution (in PBS). The lysate solution was read on an Elx800 kinetic microplate reader (Bio-Tek Instruments, Inc.) at 595 nm.

Example 1

Evaluation of Toxicity of PHY906 on Different Cell Lines

Briefly, one gram of each batch of PHY906 was added with 10 ml of water (1 mg/ml). See Table 6 for the batch properties.

TABLE 6

| Batch Properties PHY906 | | |
|---|---|---|
| Property | Batch A | Batch B |
| Origin | Taiwan, Sun-Ten | Taiwan, Sun-Ten |
| Preparation method | Standard | Standard |

The supernatant was collected after centrifugation and filtered through a 0.22 m filter. Four cell types were used to test for biological effects of each batch of PHY906: a) KB cells (ATCC cat. # CCL-17); b) HepG2 cells (ATCC cat # HB-8065); c) T-cell lymphoma cell line (CEM cells); d) Colon 38 and e) HCT116 (ATCC cat # CCL-247).

The carcinoma cells ($1\times10^4$) were seeded into a 24-well plate in either 1 ml of MEME medium or RPMI-1640 with 10% FBS and 100 μg Kanamycin on day 0. After 24 hours, the PHY906 extract was added to the cells at varying concentrations and incubated at 37° C. for 3 days. The medium was then removed and the cells stained with 0.3 ml of 0.5% (w/v) methylene blue solution (in 50% EtOH) for 30 min. The plates were washed 3 times with tap water, dried, and the cell layer was lysed with 1 ml of 1% Sarkosyl solution (in PBS). The lysate solution was read on a Elx800 kinetic microplate reader (Bio-Tec Instruments, Inc.) at 595 nm.

Cytotoxicity studies were performed with human T-cell lymphoma cell line (CEM). CEM cells ($5\times10^4$) were grown in 1 ml RPMI 1640 medium with 20% displayed fetal bovine serum. The PHY906 extract was added at day 0. The growth of cells was assessed 3 days post addition of PHY906. The number of cells were estimated using a hemacytometer.

The results of the assays using the two (2) batches are displayed in Table 7. Based on these data, PHY906 sources A and B have relatively little toxicity for KB, CEM and HCT116 cells, while having significantly greater cytotoxic effects against Colon 38 and HepG2 cells (see Table 7). Similar results are shown in Example 11, Table 10.

TABLE 7

Cytotoxicity of Traditional Herbal Formulations in Different Cell Lines.

| Herbal Formulation[b] | $IC_{50}$ (mg/ml)[a] | | | | |
|---|---|---|---|---|---|
| | KB | HepG2 | CEM | Colon 38 | HCT116 |
| PHY906A | 1.35 ± 0.52 | 0.28 ± 0.17 | 1.45 ± 0.45 | 0.08 | 1.3 |
| PHY906B | 1.80 ± 0.99 | 0.17 ± 0.12 | 1.28 ± 0.02 | 0.08 | 1.2 |

[a]Based on the dry weight of herbal formulation.
[b]Different research batch of PHY906 containing 50% excipient.

Example 2

Determination of CPT-11 Dose on BDF-1 and Nude Mice

Animal weight loss was monitored as an indication of toxicity caused by anticancer chemotherapy agents. The effect of CPT-11 on weight loss in non-tumor bearing BDF-1 mice was studied using six different dosages: 100, 200, 300, 400, 600, or 800 mg/kg body weight to determine the maximum tolerable dose in mice. A single bolus dose of CPT-11 was administered intraperitoneally (i.p.) at the beginning of the study, and weight loss was monitored daily for 12 days.

One dose of CPT-11 was administered i.p. to each mouse at the beginning of the study, and the weight loss of the animal was then monitored daily for 12 days.

Dosages lower than 200 mg/kg had little effect on body weight (comparison made with control mice receiving no CPT-11 treatments). In contrast, drug doses greater than or equal to 600 mg/kg resulted in animal death on the second day after CPT-11 administration. In general, mice were able to tolerate doses up to 400 mg/kg.

Figure 1:
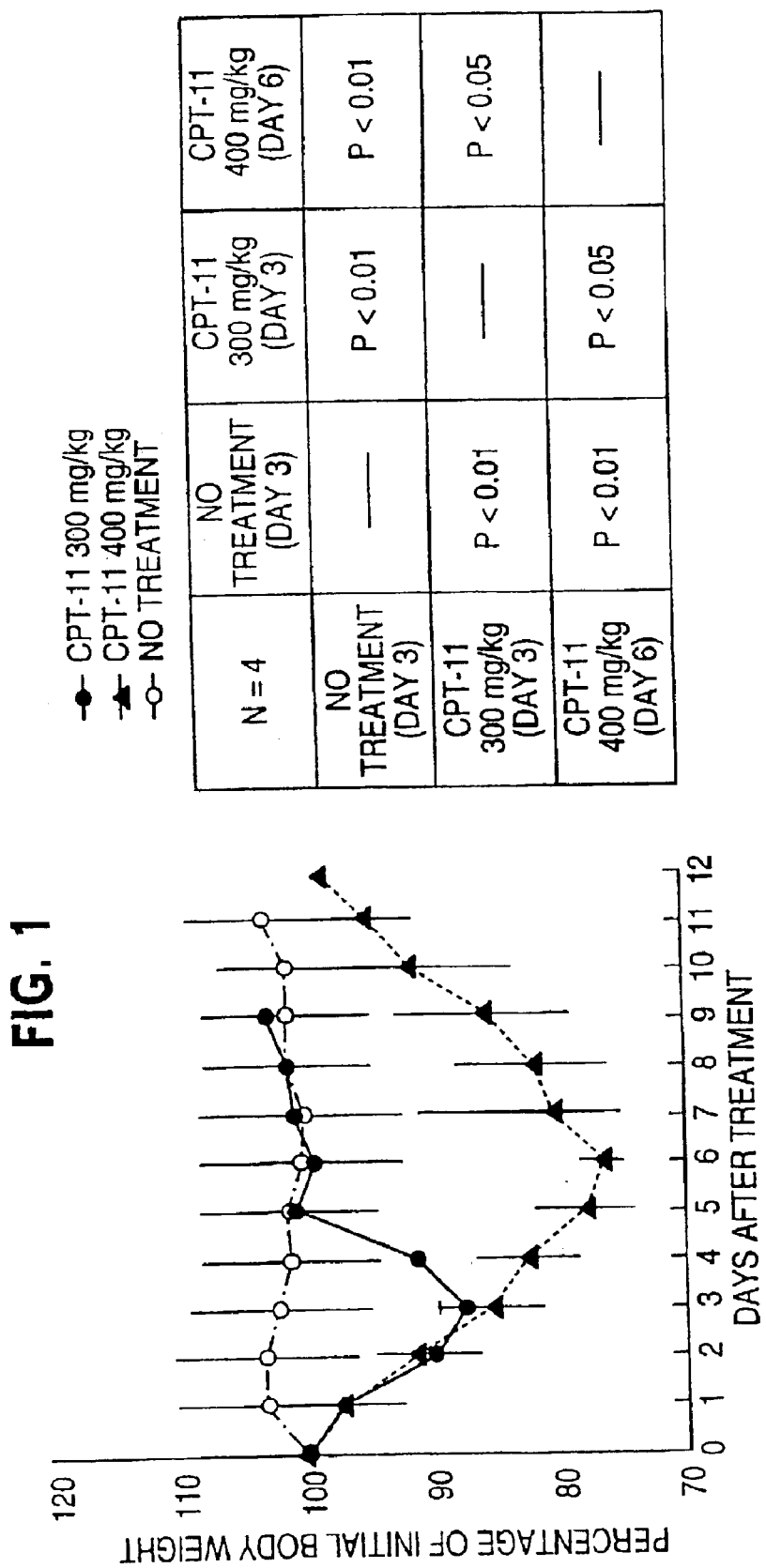
FIG. 1. Effect on Different Dosage of CPT-11 in Non-tumor Bearing BDF-1 Mice. CPT-11 was given intraperitoneally (i.p.) on day 0 only (N=5 in each group).

The profiles of the weight loss of the surviving mice are shown in FIG. 1. The average body weights of the mice treated with 300 mg/kg CPT-11 were significantly less than those of the mice that received no treatment with CPT-11 until 5 days after treatment (FIG. 1). The average body weights of these two groups of mice were not significantly different from 5 days after treatment until the end of the trial. Both the duration and extent of the weight loss were sensitive to the dose of CPT-11 administered to the animal. Weight loss was observed immediately after CPT-11 treatment and continued for six days in mice injected with 400 mg/kg of CPT-11. These animals gradually recovered their original body weight on day 12. Based on these results, either 400 mg/kg or 300 mg/kg CPT-11 was used in the BDF-1 mice model. However, nude mice inoculated with human tumor cells were significantly more sensitive to CPT-11 treatment than normal BDF-1 mice. The maximum tolerable dose of CPT-11 in nude mice bearing the human HepG2 xenografts was 200 mg/kg (data not shown).

Example 3

Effect of PHY906 on CPT-11 Induced Body Weight Loss in Tumor Bearing BDF-1 Mice

PHY906 was evaluated as a modulator of CPT-11 therapy for toxic side effects in mice inoculated with Colon 38 tumor cells. Based on the previous findings (Example 2), a single bolus dose of 400 mg/kg CPT-11 was selected to study the effect of PHY906 on weight-loss associated with toxicity of CPT-11. To evaluate whether PHY906 impairs the antitumor efficacy of CPT-11, mice were implanted subcutaneously with Colon 38 tumor cells. Ten to 14 days after inoculation, mice were treated with CPT-11 (400 mg/kg, i.p.) in the absence or presence of PHY906, which was given orally twice a day at varying doses (125 mg/kg, 250 mg/kg, and 500 mg/kg). PHY906 treatment was continued at the dose indicated for 8 consecutive days.

Figure 2:
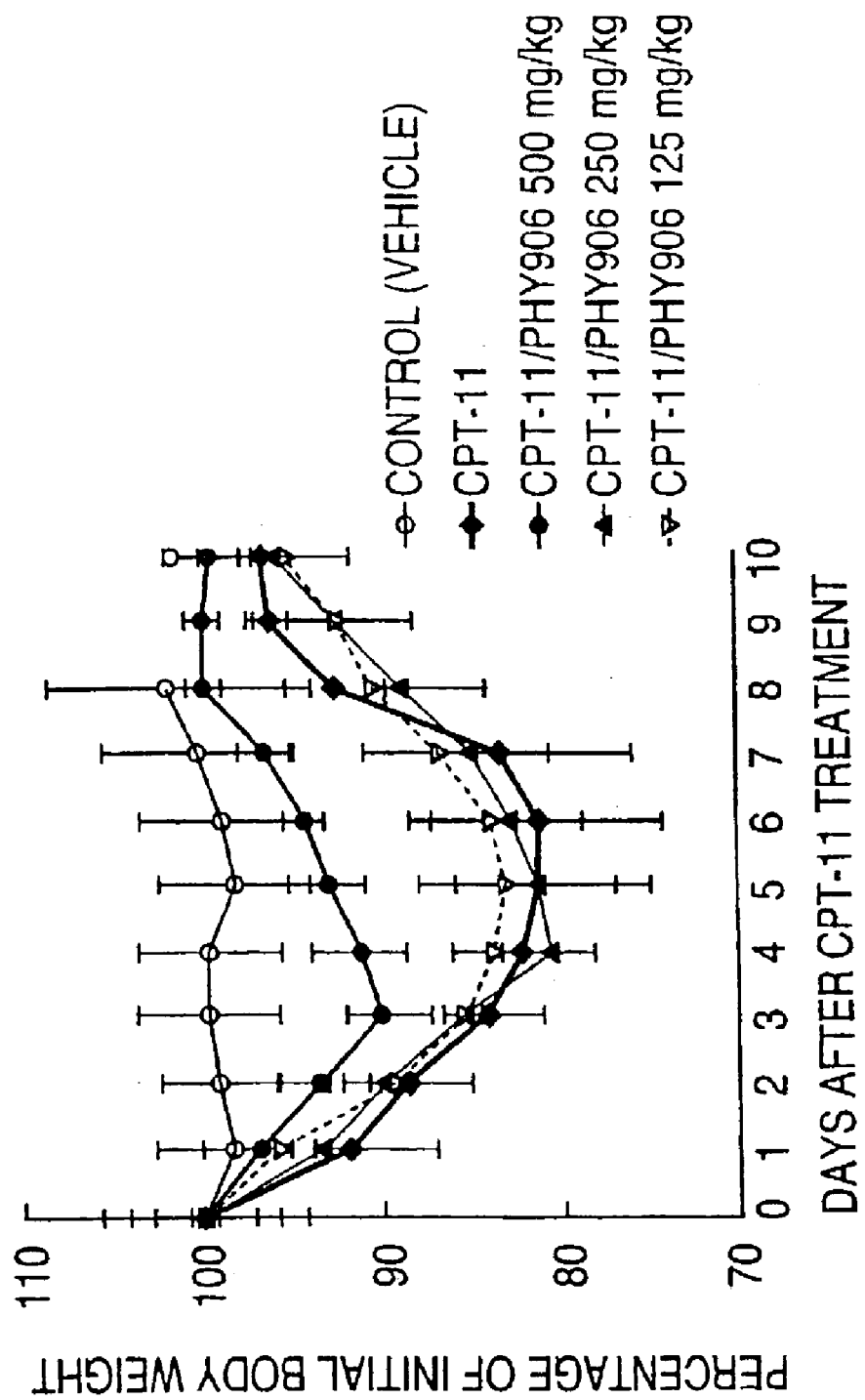
FIG. 2. Effect of PHY906 on Body Weight in CPT-11 Treated BDF-1 Mice Bearing Colon 38 Tumor. CPT-11 (400 mg/kg) was given intraperitoneally on day 0 only. PHY906 was given orally twice a day for 8 days beginning on day 0 at the dose indicated (N=5 in each group).

FIG. 2 shows that the effect of PHY906 on weight loss in CPT-11 treated mice is dose dependent. CPT-11 treated animals receiving supplemental treatment with 500 mg/kg/b.i.d. of PHY906 exhibited significant improvement in maintaining body weight and recovered their original body weight more rapidly ($p<0.01$). Table 8 summarizes the statistical results. However, mice receiving 250 mg/kg/b.i.d. of PHY906 showed no difference in body weight loss compared to controls.

TABLE 8

Statistical Analysis of PHY-906 on Weight Loss in Tumor Bearing Mice Treated With CPT-11.

| N = 5 | No Treatment | CPT-11 | CPT-11/PHY906 500 mg/kg | CPT-11/PHY906 250 mg/kg | CPT-11/PHY906 125 mg/kg |
|---|---|---|---|---|---|
| No Treatment | — | $P < 0.01$ | $P < 0.05$ | $P < 0.01$ | $P < 0.01$ |
| CPT-11 | $P < 0.01$ | — | $P < 0.01$ | $P > 0.1$ | $P > 0.1$ |
| CPT-11/PHY906 500 mg/kg | $P < 0.05$ | $P < 0.01$ | — | $P < 0.01$ | $P < 0.01$ |
| CPT-11/PHY906 250 mg/kg | $P < 0.01$ | $P > 0.1$ | $P < 0.01$ | — | $P > 0.1$ |
| CPT-11/PHY906 125 mg/kg | $P < 0.01$ | $P > 0.1$ | $P < 0.01$ | $P > 0.1$ | — |

Example 4

Tumor Weight of Colon 38 Inoculated Mice Treated with CPT-11 and PHY906

Mice were treated as set forth in Example 3 and evaluated for tumor weights over a nine day period.

Figure 3:
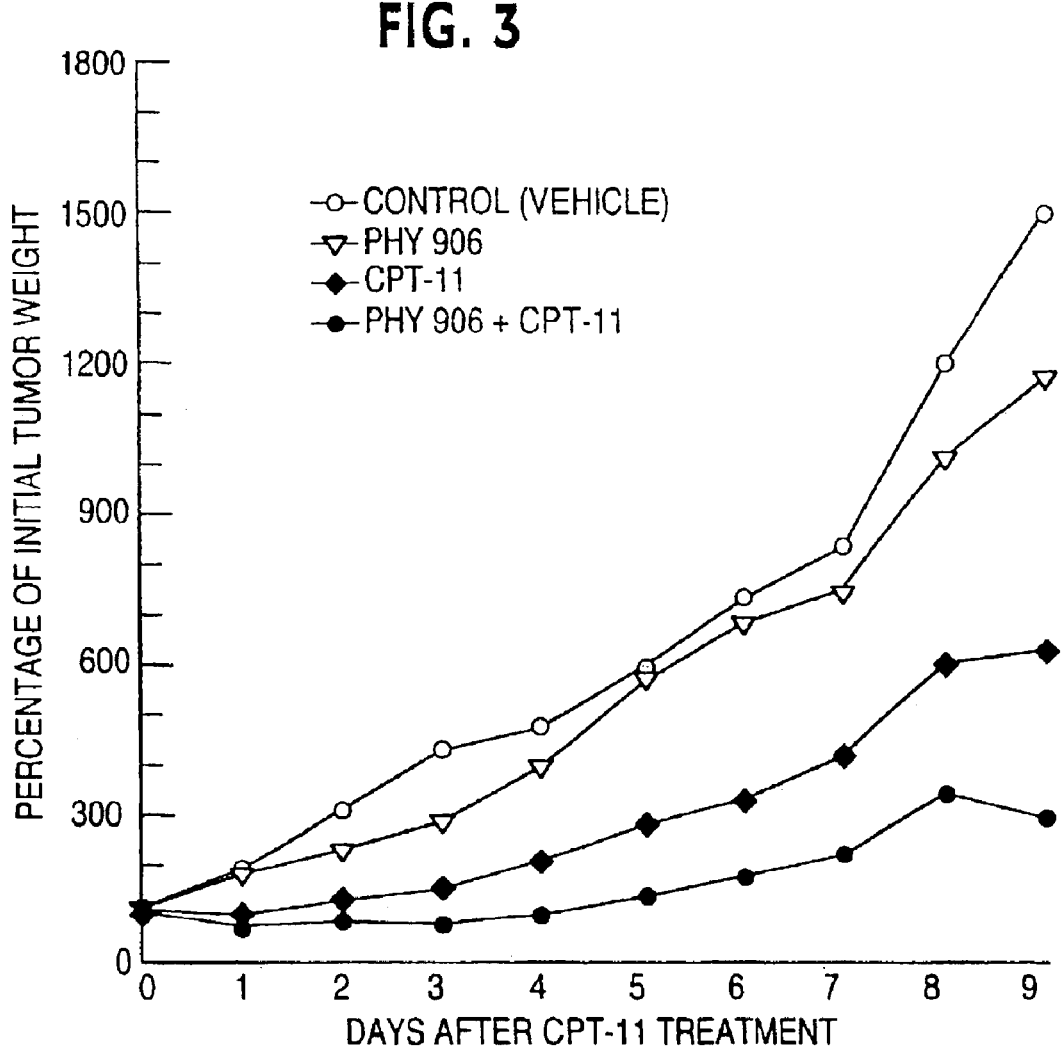
FIG. 3. Effect of PHY906 on Tumor Growth in CPT-11 Treated BDF-1 Mice Bearing Colon 38 Tumor. CPT-11 (400 mg/kg) was given intraperitoneally on day 0 only. PHY906 (500 mg/kg) was given orally twice a day for 8 days beginning on day 0. The p values were calculated using the Student's paired t-test.

The results demonstrate that treatment with PHY906 neither impedes nor impairs the antitumor efficacy of the CPT-11 (FIG. 3). In fact, the data suggest that this herbal medicine may actually enhance CPT-11 anti-tumor activity.

These preliminary results suggest that the herbal composition PHY906 can be used as a modulator for CPT-11 chemotherapy to significantly improve and alleviate the toxic side effects of CPT-11 without compromising the anti-tumor efficacy of the CPT-11.

Example 5

Effect of PHY906 on Antitumor Activity and Hematological Toxicity of CPT-11 in BDF-1 Mice Bearing Colon 38 Tumors Based on the results obtained in the above studies, 500 mg/kg/b.i.d. PHY906 offers the best protection for host toxicity induced by the maximum tolerable dose of 400 mg/kg CPT-11. This set of dosages was used for the next studies. Colon 38-bearing BDF-1 mice treated with one dose of CPT-11 (400 mg/kg, i.p.) were given 500 mg/kg/b.i.d. PHY906 orally for either 4 or 8 days. Five mice were used treatment in combination with CPT-11 (Group D). This suggests that PHY906 treatment can protect mice against mortality induced by a single dose of 400 mg/kg CPT-11.

TABLE 9

Effect of PHY906 on Survival of CPT-11 Treated BDF-1 Mice Bearing Colon 38 Tumor.

| Medication Regimen | Treatment | | | | Total No. of Mice | | |
|---|---|---|---|---|---|---|---|
| | CPT-11 | | PHY906 | | Treated | Survived | |
| | Dose (mg/kg) | Days | Dose (mg/kg) | Days | N | N | Survival[a] % |
| A | 0 | 0 | 0 | 0 | 35 | 35 | 100 |
| B[b] | 400 | 1 | 0 | 0 | 40 | 33 | 82.5 |
| C | 0 | 0 | 500 | 4 | 35 | 35 | 100 |
| | 0 | 0 | 500 | 8 | 15 | 15 | 100 |
| D[c] | 400 | 1 | 500 | 4 | 20 | 19 | 95 |
| | 400 | 1 | 500 | 8 | 24 | 24 | 100 |

[a]All the animals were observed for 14 days.
[b]7 of 40 mice with CPT-11 treatment died on day 5 (N = 1), 6 (N = 3), 7 (N = 1) and 8 (N = 2).
[c]With the combination treatment of CPT-11 and PHY906 (4 days) treatment, one mouse died on day 6.

in each group, and the experiment was repeated eight times. FIG. 3 represents a typical result of all of experiments. The antitumor activity of CPT-11, as measured by tumor size, was not compromised by the concomitant PHY906 therapy in the animal model. In fact, a slight reduction in tumor size occurred, suggesting that PHY906 may potentiate the antitumor activity of CPT-11.

Figure 4:
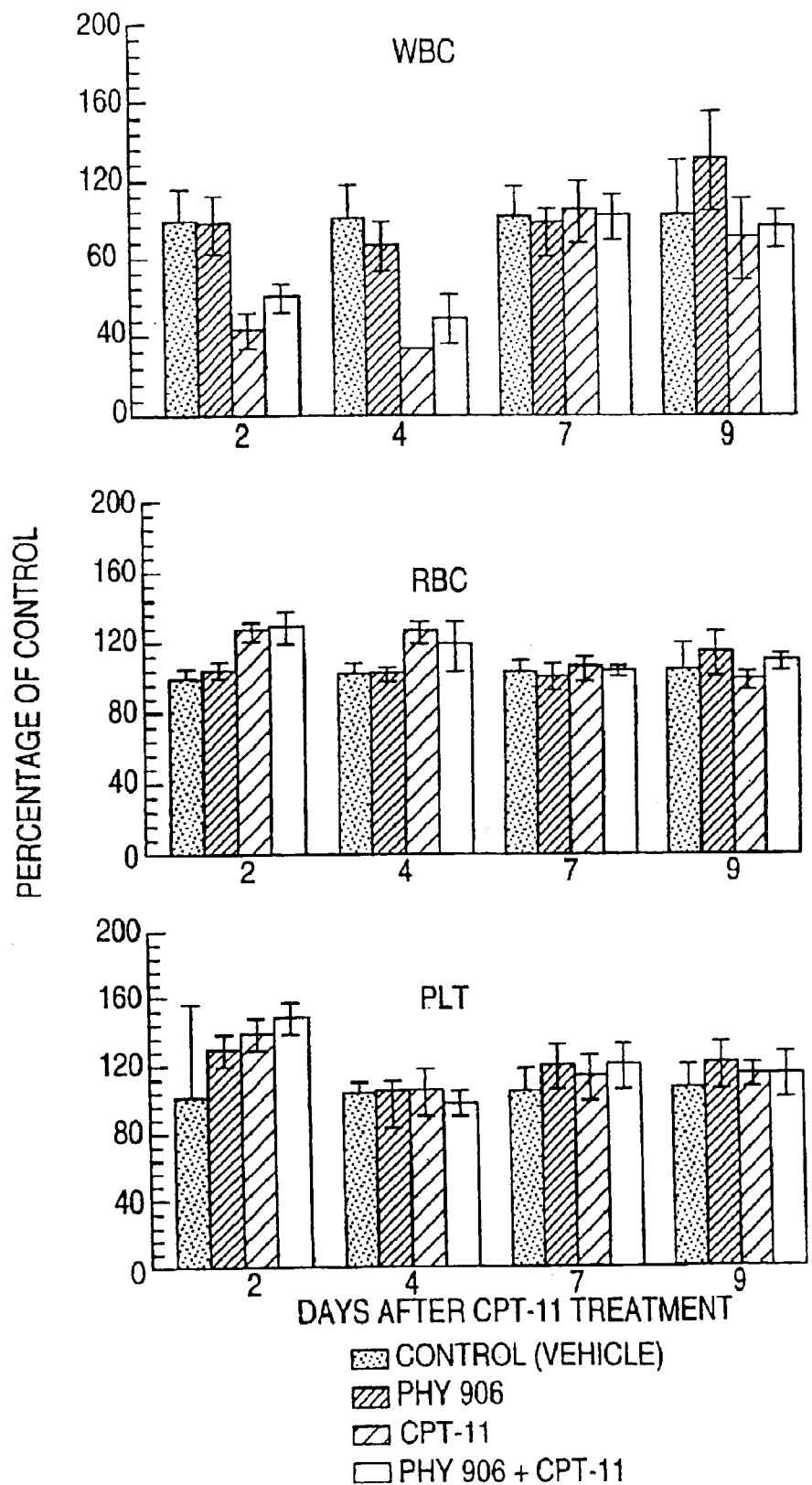
FIG. 4. Effect of PHY906 on Hematological Change in CPT-11 Treated BDF-1 Mice Bearing Colon 38 Tumor (N=5 in each group). CPT-11 (400 mg/kg) was given intraperitoneally on day 0 only. PHY906 (500 mg/kg) was given orally twice a day for 4 days beginning on day 0 (N=5 in each group).

Myelo-suppression is a common side effect among patients treated with CPT-11 (Bleiberg H and Cvitkovic E., Eur J Cancer 32A (Suppl 3):S18–S23 (1996)). To evaluate whether PHY906 beneficially reverses myelo-toxicity induced by CPT-11, hematological activity was examined in BDF-1 mice bearing Colon 38 tumors. As shown in FIG. 4, PHY906 was found to have no impact on red blood cell count or platelet count among all regimens, and demonstrated no protection on myelo-suppression induced by CPT-11. With respect to the antitumor activity and hematological activity, there was no significant difference between a 4-day or 8-day co-treatment of PHY906 with CPT-11 (data not shown).

Example 6

Effect of PHY906 on Mortality of CPT-11 on BDF-1 Mice Bearing Colon 38 Tumors

Mice were divided into four groups with different treatment regimens: Group (A) treatment with vehicle; Group (B) treatment with a single dose of 400 mg/kg CPT-11 by i.p. injection; Group (C) treatment with PHY906 (500 mg/kg/ b.i.d.) alone; or Group (D) treatment with a single dose of 400 mg/kg CPT-11 plus 500 mg/kg/b.i.d. PHY906 for 4 or 8 days. The sequence of each treatment regimen appears in Materials and Methods. As depicted in Table 9, 35 of 35 tumor-bearing mice (100%) from Group A and 15 of 15 mice (100%) from Group C survived treatment with either vehicle or PHY906 alone for 4 or 8 days, indicating no or very low toxicity for PHY906. In contrast, treatment with CPT-11 alone (Group B) resulted in only 33 of 40 tumor-bearing mice (82.5%) surviving after 8 days. However, this survival rate dramatically improved to either 95% (19 of 20 mice) or 100% (24 of 24 mice) after receiving 4 or 8 days of PHY906

Example 7

Effect of PHY906 on the Antitumor Activity of FU/LV in BDF-1 Mice Bearing Colon 38 Tumors FU/LV in combination shows potent antitumor activity and is used as the first line treatment of colorectal cancer in patients (Goldber R. M. and Erlichman C., Oncology 12: 59–63 (1988); Saltz L. B, Cox J. V, Blanke C, et al., New. Eng. J. Med. 343:905–914 (2000)). Therefore, experiments similar to that described above for CPT-11 treatment were carried out with FU/LV in animals. Colon 38 tumor bearing mice were divided into four groups: Group (A) treatment with vehicle; Group (B): treatment with PHY906 alone; Group (C) treatment with FU/LV alone; and Group (D) treatment with FU/LV plus PHY906. The sequence of each regimen appears in Materials and Methods. In this set of experiments, FU/LV was given to mice only once on day 0, whereas PHY906 was administered twice daily for 4 consecutive days.

Figure 5:
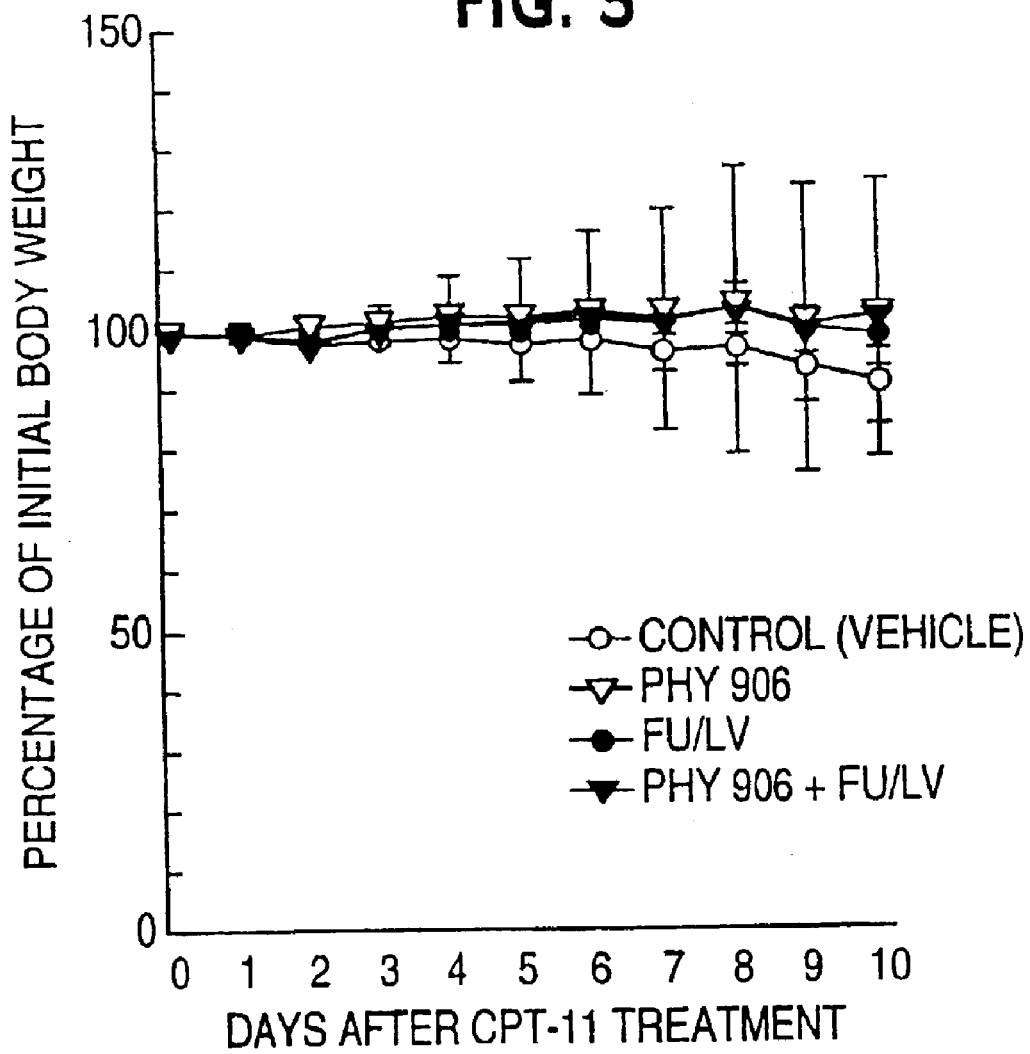
FIG. 5. Effect of PHY906 on Body Weight in FU/LV Treated BDF-1 Mice Bearing Colon 38 Tumor. Sequential administration of LV (100 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).
Figure 6:
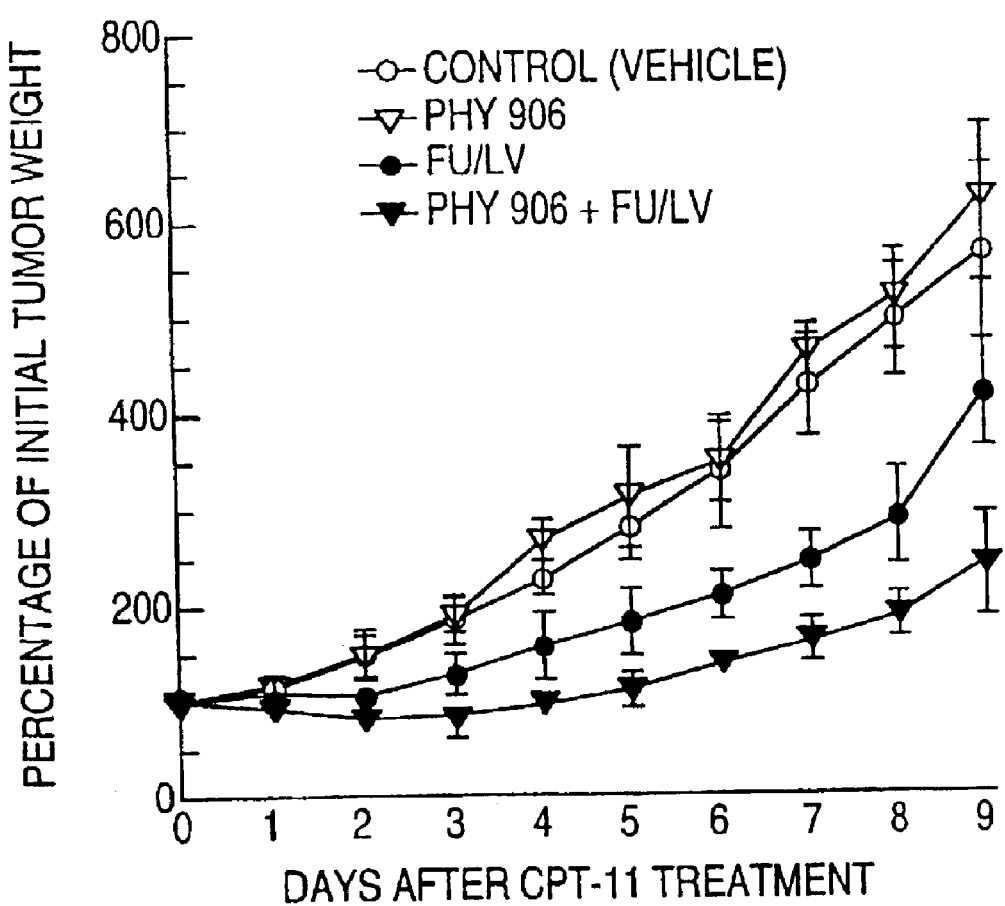
FIG. 6. Effect of PHY906 on Tumor Growth in FU/LV Treated BDF-1 Mice Bearing Colon 38 Tumor. Sequential administration of LV (100 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).
Figure 7:
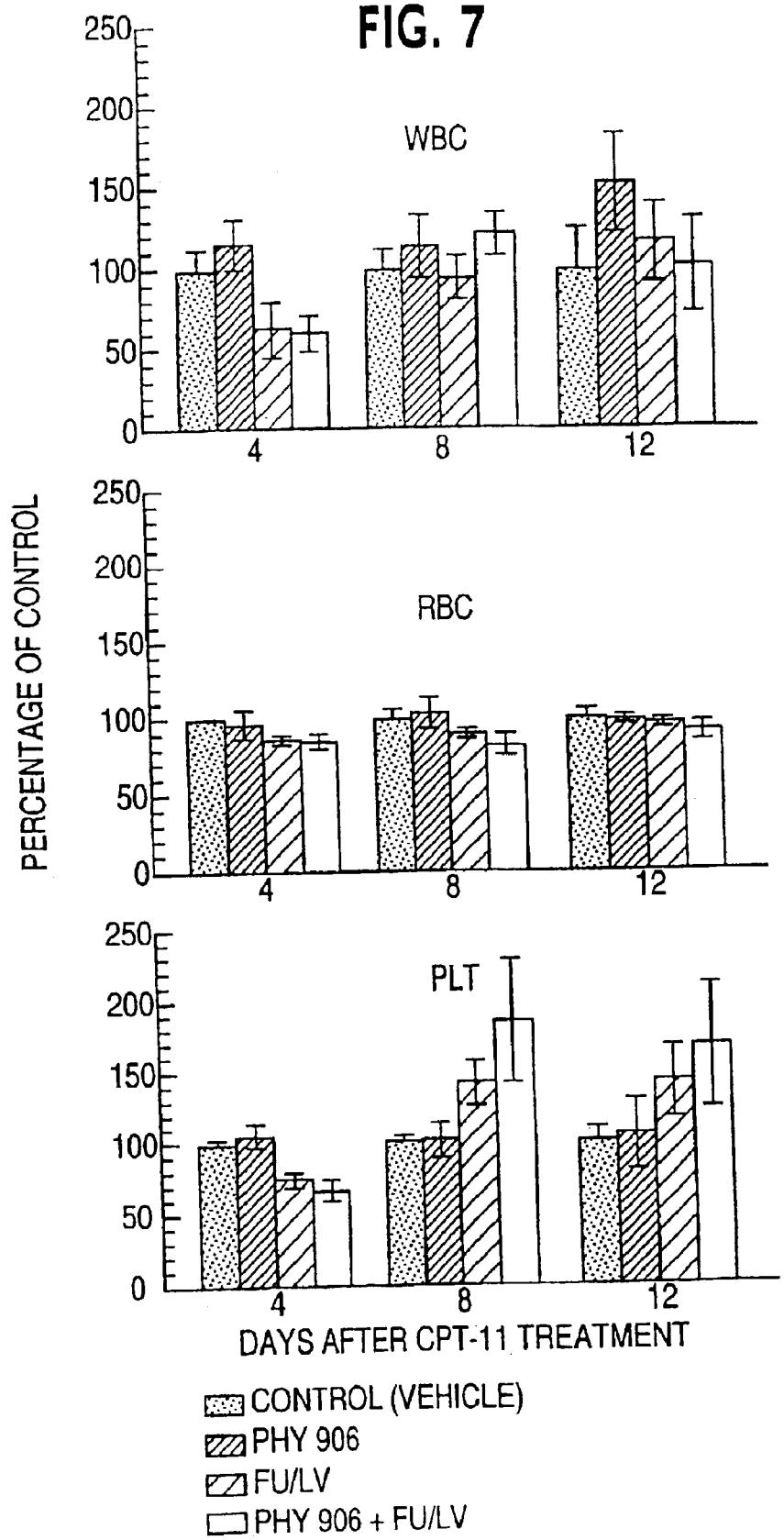
FIG. 7. Effect of PHY906 on Hematological Change in FU/LV Treated BDF-1 Mice Bearing Colon 38 Tumor. Sequential administration of LV (100 mg/kg) and FU (100 mg/kg) was given intraperitoneally during 1 hr period on day 0 only, as described in Materials and Methods. PHY906 was given orally 30 min after initial dose of LV on day 0 and continued twice a day for 4 days at 500 mg/kg (N=5 in each group).

Changes in body weight and tumor size were monitored daily, as shown in FIGS. 5 and 6, respectively. As depicted in FIG. 5, little change in body weight occurred in the four groups. This observation is in contrast to that obtained with CPT-11 treatment. Since dose-response studies of FU/LV on body weight loss were not performed, it is possible that the FU/LV dose administered in this experiment was not high enough to induce toxicity and associated body weight loss. Although body weight loss was insufficient to demonstrate a protective effect PHY906 on FU/LV, FIG. 6 indicates that concomitant treatment of PHY906 did not impair the antitumor activity of FU/LV in BDF-1 mice bearing Colon 38 tumors. The tumor growth profile of animals in Group D is slower than that in Group C, suggesting that PHY906 may enhance the antitumor activity of FU/LV in this animal model. In addition, the hematological toxicity of FU/LV in treated mice concomitantly administered PHY906 was monitored on days 4, 8, and 12. Leucopenia or thrombocytopenia, well known side effects induced by FU/LV (van der Wilt C. L, van Groeningen, C. J, Pinedo H. M, et al., J. Cancer Res. Clin. Oncol. 123:595–601 (1997)), was not reversed by PHY906 (FIG. 7).

Example 8

Effect of PHY906 on Antitumor Activity of CPT-11/FU/LV in BDF-1 Mice Bearine Colon 38 Tumors The FDA recently approved the new triple combination therapy of CPT-11 plus FU/LV as a first line treatment for advanced colorectal cancer (Goldber R. M. and Erlichman C., Oncology 12: 59–63 (1988); Saltz L. B, Cox J. V, Blanke C, et al., New. Eng. J. Med. 343:905–914 (2000)). This regimen has been proven to slow the progress of tumor growth as well as the mortality rate. However, severe, late-onset diarrhea is often observed in patients receiving this triple treatment regimen. Previous experiments demonstrated that PHY906 could increase the therapeutic index of CPT-11 in BDF-1 mice bearing Colon 38 tumors. Therefore, PHY906 was evaluated using a similar protocol as in Example 7 for its efficacy on alleviating the dose-limiting toxicity of triple chemotherapy. BDF-1 mice bearing Colon 38 tumors were divided into two groups: Group (A) treated with CPT-11/FU/LV only; Group (B) treated with CPT-11/FU/LV plus PHY906. The doses of FU and LV used in both groups were 100 mg/kg each, because very low toxicity was observed in previous studies at these doses. A dose-dependent study of CPT-11 was not performed in this triple chemotherapy regimen, but either 200 mg/kg or 300 mg/kg CPT-11 was used. The sequence of each regimen appears in Materials and Methods. PHY906 was administered twice daily for 4 days post chemotherapy.

Figure 8:
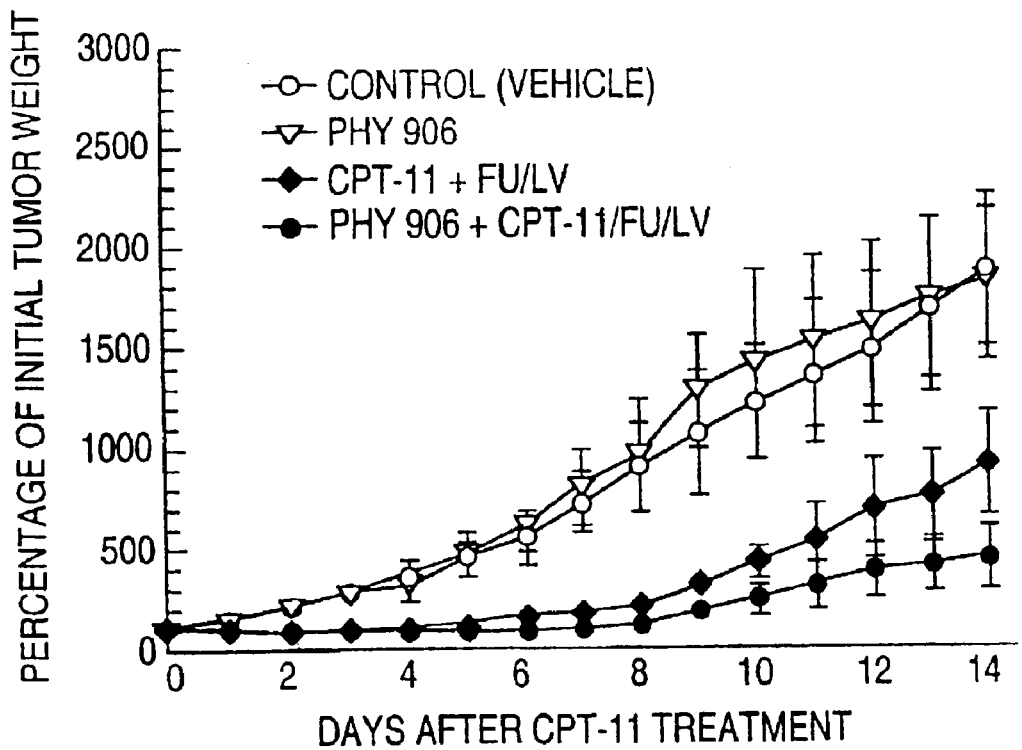
FIG. 8. Effect of PHY906 on Tumor Growth in CPT-11/FU/LV Treated BDF-1 Mice Bearing Colon 38 Tumor.

The results indicate that PHY906 does not impair the antitumor efficacy of triple therapy at both 200 mg/kg and 300 mg/kg CPT-11, as shown in FIGS. 8 and 9, respectively. As depicted in FIG. 8, using 200 mg/kg CPT-11 in triple combination therapy, PHY906 slightly enhances tumor suppression at day 14 (p=0.045). At 300 mg/kg CPT-11, the enhancement of PHY906 in tumor suppression was not significant at day 14 (p=0.05), but was significant at day 21 (p=0.014), compared to groups receiving no PHY906 treatment. This result suggests that a longer time period may be needed to observe the enhancement of PHY906 on CPT-11/FU/LV tumor suppression. At the dose studied, PHY906 showed a similar beneficial effect on antitumor activity in triple combination therapy and CPT-11 treatment.

At the doses used in the triple combination treatment, animals showed body weight loss. However, PHY906 did not slow weight loss during therapy, as shown in FIG. 10. In addition, PHY906 did not affect the recovery of body weight loss.

Example 9

Pharmacokinetics of CPT-11/FU/LV in BDF-1 Mice Bearing Colon 38 Tumor in the Presence and Absence of PHY906

The pharmacokinetic data of CPT-11/FU/LV in BDF-1 mice bearing Colon 38 tumor in the presence and absence of PHY906 are shown in FIGS. 18–20. PHY906-6 is a clinical batch of PHY906, containing 10% excipient (starch).

The area under the curve (AUC) of CPT-11 in plasma increases after co-administration of PHY906 with the triple combination of CPT-11/FU/LV. There is no significant change of CPT-11 in either tumor or liver tissues after PHY906 co-administration.

SN-38, an active metabolite of CPT-11, remains unchanged in plasma, liver, or tumor.

The AUCs of FU and its nucleoside/nucleotide metabolites (FU+FUR+FUMP) in plasma or liver change after PHY906 co-administration with the triple combination of CPT-11/FU/LV.

Example 10

Effect of PHY906 on Antitumor Activity and Toxicity of CPT-11 in Human HepG2 Tumor-Bearing Nude Mice Results from the above Examples, specifically Examples 5, 7, and 8, indicate that PHY906 in combination with chemotherapeutic agents may potentiate the antitumor effects of chemotherapeutic agents and further retard tumor growth. Based upon the known pharmacological profiles of herbs contained in PHY906 (Table 1), it is speculated that the enhancing effects may act through immunological and/or hematological systems in normal mice. Therefore, experiments were designed to test the hypothesis in nude mice, which are deficient in immunological and hematological systems.

Human HepG2 tumor cells were implanted into NCr-nude mice to test the effect of PHY906 on the antitumor activity of CPT-11. Previous experiments showed that the maximum tolerable dose of CPT-11 in nude mice was 200 mg/kg, which was used in this study. CPT-11 (200 mg/kg, i.p.) was given on day 0. PHY906 was given twice daily at 500 mg/kg starting on day 0. As shown in FIG. 11, PHY906 did not compromise the antitumor effect of CPT-11 on human HepG2 xenografts in nude mice. However, unlike the observation in BDF-1 mice, PHY906 showed no beneficial effect on preventing body weight loss (FIG. 12) or animal death (data not shown) caused by CPT-11. The fact that PHY906 does not protect nude mice from weight loss as it does normal mice suggests that PHY906 exerts its effects through hematological and immunological systems, which nude mice lack.

Example 11

Effects of Different Chinese Herbal Formulations on Antitumor Effect of CPT-11, Body Weight Loss and Survival in Mice Diarrhea is one of the dose-limiting toxicities among patients treated with cancer chemotherapeutic agents. In addition to PHY906, other anti-diarrhea medicines were examined. These included Chinese medicines, such as PHY-14ST, PHY-15ST, and PHY-915, as well as loperamide, currently recommended as the anti-diarrhea drug for CPT-11-induced late-onset diarrhea.

In addition to tumor growth inhibition and loss of body weight, we examined survival rates in mice receiving different herbal formulations in combination with a single bolus administration of CPT-11. Of the several formulations examined, PHY906 was the only one observed to enhance CPT-11 antitumor activity (Table 9), even though certain herbs contained in PHY906 are also present in the other herbal formulations. In the mortality study, PHY906 showed no statistical effect on animal death rates (P=0.044). Other anti-diarrhea medicines tested, such as PHY-14ST, PHY-15ST and loperamide, were observed to be completely ineffective in protecting against body weight loss or enhancing the antitumor effects of CPT-11. Surprisingly, PHY-915, was observed to decrease CPT-1 antitumor activity (Table 10).

TABLE 10

Effect of Different Herbal Formulations on CPT-11 Treated BDF-1 Mice Bearing Colon 38 Tumor.

| Herbal Formulation (1 g[c]/kg, bid, 8 days) | Protection from Body Weight Loss | P value[b,d] | Antitumor Effect | P value[b,e] | Animal Death[a] (Death/Total) |
|---|---|---|---|---|---|
| None | | | | | 7/40 |
| PHY906 | Significant | 0.0004 | Enhancement | 0.0027 | 0/24 |
| PHY14ST | No Change | 0.1072 | No Change | 0.2742 | 1[f]/10 |
| PHY15ST | No Change | 0.3259 | No Change | 0.6535 | 0/3 |
| PHY915 | Significant | 0.0306 | Decrease | 0.0885 | 0/5 |
| Loperamide | No Change | 0.9706 | No Change | 0.1595 | 3[g]/10 |

[a]All of the animals were observed for 14 days.
[b]The p values were calculated using the Student's paired t-test.
[c]based on the dry weight of formulations which contain excipient.
[d]Calculated on the day that CPT-11-treated mice reached maximum body weight loss.
[e]Calculated on the tumor size at day 6 after initial drug treatment.
[f]One mouse died on day 6.
[g]Mice died on day 3 (N = 1), 4 (N = 1) and 5 (N = 1).

Example 12

Cytotoxicity of PHY906 in Different Cell Lines

To evaluate in vitro cell models as measures of quality assurance, the effects of two different preparations of PHY906 (PHY906A and PHY906B) on the growth inhibition of different human tumor cell lines and mouse Colon 38 tumor cell lines were studied. As shown in Table 11, PHY906A and PHY906B showed no significant difference in growth inhibitory activities among the cell lines. Of note, HepG2 cell lines were found to be more sensitive to PHY906 than other human cell lines.

TABLE 11

Cytotoxicity of PHY906 in Different Cell Lines.

| Herbal Formulation[b] | IC$_{50}$ (mg/ml)[a] | | | | |
|---|---|---|---|---|---|
| | KB | HepG2 | CEM | HCT116 | Colon 38 |
| PHY906A | 0.67 ± 0.26 | 0.14 ± 0.08 | 0.73 ± 0.17 | 0.65 | 0.08 ± 0.02 |
| PHY906B | 0.90 ± 0.5 | 0.09 ± 0.06 | 0.64 ± 0.01 | 0.6 | 0.07 ± 0.02 |

[a]Based on the dry weight of aqueous extract of raw herbs.
[b]Different research batch of PHY906.

The results of the above experiments suggest that PHY906 reduces some host toxicities induced by treatments of CPT-11, FU/LV, or the triple combination therapy with CPT-11/FU/LV. The botanical drug PHY906 not only maintains, but also potentiates, the antitumor activity of the chemotherapeutic agents tested. Indeed, PHY906 enhances the therapeutic index of CPT-11, FU/LV and CPT-11/FU/LV by increasing the overall antitumor activity in both Colon 38 tumor-bearing mice and human Hep G2 xenografts in nude mice. These observations were tested with several anticancer agents in two different tumor models (FIGS. 3, 6, 8, 9, and 11).

Example 13

Effect of PHY906 on Tumor Growth in Colon 38 Inoculated Mice Treated with L-OddC PHY906 was evaluated as a modulator of L-OddC (beta-L-Dioxolane-cytidine) therapy for tumor growth in mice inoculated with Colon 38 tumor cells. Mice were subjected to a subcutaneous injection of murine Colon 38 tumor cells. Seven days after inoculation of the cancer cells, mice were treated with L-OddC (25 mg/kg) intraperitoneally and oral administration of PHY906 (500 mg/kg, b.i.d.). The animals were then administered only with the same dose of PHY906 continuously for the rest of the experiment.

As shown in FIG. 13, treatment with L-OddC demonstrates that PHY906 neither impedes nor impairs the antitumor efficacy of the L-OddC. In fact, the data suggest that this herbal medicine may actually enhance L-OddC antitumor activity.

Thus, these results suggest that the herbal PHY906 can be used as a modulator for L-OddC chemotherapy to significantly improve and alleviate the toxic side effects without compromising the anti-tumor efficacy of the L-OddC.

Example 14

Effect of PHY906 on Tumor Growth in Colon 38 Inoculated Mice Treated with VP-16

PHY906 was evaluated as a modulator of VP-16 (etoposide, a topoisomerase II inhibitor) therapy for tumor growth in mice inoculated with Colon 38 tumor cells. Mice were subjected to a subcutaneous injection of murine Colon 38 tumor cells. Seven days after inoculation with the cancer cells, mice were treated with VP-16 (25 mg/kg) intraperitoneally and oral administration of PHY906 (500 mg/kg, b.i.d.). The animals were then administered only with the same dose of PHY906 continuously for the rest of the experiment.

As shown in FIG. 14, treatment with VP-16 demonstrates that PHY906 neither impedes nor impairs the antitumor efficacy of the VP-16. In fact, the data suggest that this herbal medicine may actually enhance VP-16 anti-tumor activity.

Thus, these results suggest that the herbal PHY906 can be used as a modulator for VP-16 chemotherapy to significantly improve and alleviate the toxic side effects without compromising the anti-tumor efficacy of the VP-16.

Example 15

Effect of PHY906 on Tumor Growth in Colon 38 Inoculated Mice Treated with 5-Fluorouracil PHY906 was evaluated as a modulator of 5-fluorouracil (FU) therapy for tumor growth in mice inoculated with Colon 38 tumor cells. Mice were subjected to a subcutaneous injection of murine Colon 38 tumor cells. Seven days after inoculation of the cancer cells, mice were treated with 5-fluorouracil at two doses (250 mg/kg, one dose on day 0, or 30 mg/kg daily dose given from day 0 to day 4) intraperitoneally, and with PHY906 (500 mg/kg, b.i.d.) by oral administration. The animals were then administered only with the same dose of PHY906 continuously for the rest of the experiment.

As shown in FIGS. 15 and 16, treatment with 5-fluorouracil demonstrates that PHY906 neither impedes nor impairs the antitumor efficacy of the 5-fluorouracil. In fact, the data suggest that this herbal medicine may actually enhance 5-fluorouracil anti-tumor activity.

Thus, these results suggest that the herbal PHY906 can be used as a modulator for 5-fluorouracil chemotherapy to significantly improve and alleviate the toxic side effects without compromising the anti-tumor efficacy of the 5-fluorouracil.

Example 16

Effect of PHY906 on Tumor Growth in Colon 38 Inoculated Mice Treated with CPT-11 and Loperamide PHY906 was evaluated as a modulator of CPT-11 therapy for tumor growth in mice inoculated with Colon 38 tumor cells in the presence of anti-diarrhea medication Loperamide. Mice were subjected to a subcutaneous injection of murine Colon 38 tumor cells. Seven days after inoculation of the cancer cells, mice were treated with CPT-11 (400 mg/kg, i.p.), alone, in the presence of orally administered of PHY906 (500 mg/kg, b.i.d.), or in the presence of Loperamide (2 mg/kg, p.o., b.i.d.).

FIG. 17 compares the antitumor effect of PHY906 and Loperamide. As shown in FIG. 17, CPT-11 in the presence of PHY906 is more effective at reducing tumor growth (as determined as a percentage of initial tumor weight) than Loperamide.

These preliminary results suggest that the herbal PHY906 is more effective than standard administration of Loperamide for delayed CPT-11 induced diarrhea.

Example 17

To Determine the Minimal Effective Dose (MED) and the Optimal Duration of PHY906 Administration when Given in Combination with Irinotecan.

Introduction: Several studies indicate that Kampo medicine, which consists of seven herbs, is effective in preventing the occurrence of CPT-11-induced diarrhea in animals and in reducing the severity of CPT-11-induced diarrhea in vivo (Mori, 1998).

PHY906 has also been evaluated in an in vivo animal model and has been shown to reduce the severity of irinotecan-induced toxicity. Accordingly, based on a long historical experience (1500 years) demonstrating safety in humans, the promising pre-clinical activity of this compound in an animal model, and the potential activity noted for a related herbal compound in this setting, a study can be conducted to evaluate the effect of PHY906 on the severity of chemotherapy-induced toxicities, such as weight loss, diarrhea, overall performance status, and quality of life, and on the anti-tumor activity of irinotecan or other drugs in patients with refractory advanced colorectal cancer.

This study includes patients with histologically confirmed, FU-refractory, advanced colorectal cancer. Measurable or evaluable disease is not required. Patients with central nervous system (CNS) metastases are eligible provided the CNS disease has remained stable for at least 4 weeks following completion of surgery, chemotherapy, and/or radiation therapy.

Participants in the study will be $\geq 18$ years of age and will have no significant underlying medical diseases. All patients will have a performance status of ECOG 0–2, a life expectancy of at least 3 months, and have given informed consent. (ECOG is an abbreviation for "Eastern Cooperative Oncology Group. ECOG 0=patient performing normal activity; ECOG 1=patient having minimal symptoms; ECOG 2=to patient spents <50% of time in bed; ECOG 3=patient spents >50% time spent in bed; ECOG 4=patient is bed bound.) Patients must have fully recovered from the effects of any prior surgery and have not received wide-field radiation or any chemotherapy within 4 weeks (6 weeks for nitrosoureas or mitomycin C) of entry onto this study. An ANC (absolute neutrophil count) $\geq 1500/\mu l$, platelet count $\geq 40$ ml/min, and a total bilirubin $\leq 2.0$ mg/dl is required for entry onto study.

Pretreatment Evaluation: Prior to the start of treatment, all patients will have a complete history, physical examination, and a determination of their performance status. The laboratory studies will include a complete blood count (CBC) with differential, a serum albumin, electrolytes, glucose, blood urea nitrogen (BUN), creatinine, serum calcium and magnesium, liver function tests, prothrombin and partial thromboplastin time, and a urinalysis.

Treatment: Irinotecan will be reconstituted from a lyophilized powder into 2 ml of sterile water, diluted in 100 ml of D5W (5% Dextrose in water), and administered over 90 min at a dose of 125 mg/m². Irinotecan chemotherapy will be administered on a weekly schedule for 4 weeks with a 2 week rest period in the outpatient clinic at each of the participating hospitals.

PHY906 will be taken on an empty stomach 30 min prior to meals. On chemotherapy treatment days, the first dose will be taken before the administration of irinotecan.

PHY906 will be administered orally three times a day before each meal starting at an initial dose of 0.60 g. (total daily dose, 1.80 gm/day). The dose of PHY906 that is presently being used by patients in the Orient is 7.2 gm/day, and to date, no adverse events have been observed. Thus, the dose that is proposed to start out this trial is ¼th the usual dose of the herbal medicine. PHY906 will be given for an entire 4-week course of chemotherapy along with irinotecan with a 2-week rest. A minimum of three patients will be treated at this initial dose level of PHY906. Once the 3 patients have completed a full 6-week cycle, if 0 of 3 patients experience dose-limiting toxicity (DLT), then the next higher dose will be used for the subsequent group of 3 patients. In all patients, pharmacokinetic studies will be performed 24 hr after the start of the first cycle of chemotherapy.

If 1 of 3 patients experience DLT, then 3 more patients will be treated at the same dose level. If ≦1 of the next 3 experience DLT (1 or 2 of 6 total patients), the dose will be escalated to the next dose level except when those events occur during the doubling scheme, when the next escalation will be to level n+1 on the modified Fibonacci scheme (Table 12).

TABLE 12

Dose Escalation Schedule of PHY906.

| Dose Level | Escalation | Total Dose (gm/day) |
|---|---|---|
| 1 | Starting | 1.8 |
| 2 | 2 × level 1 | 3.6 |
| 3 | 2 × level 2 | 7.2 |

Once the 7.2 gm/day dose level is reached and no ≧ grade 2 toxicity is observed at this level "n" a modified Fibonacci escalation as shown below will be performed.

| N + 1 | 1.5 × level n |
| N + 2 | 1.33 × level n + 1 |
| N + 3 | 1.25 × level n + 2 |

All subsequent levels: 25% increments until the maximum tolerated dose is reached.

Dose Escalation Schedule of PHY906: If clinically indicated and considered necessary by the Principal Investigators, a lower dose level, rather than the level specified above, may be utilized.

The rate of subject entry and escalation to the next dose regimen will depend upon assessment of the safety profile of patients entered at each dose level. Toxicity will be evaluated and graded according to the NCI Clinical Trial Guidelines (CTG) Expanded Common Toxicity Criteria.

The antiemetic schedule for this protocol will consist of 1–2 mg of granisetron admixed in 50 ml normal saline and administered via ½ hr prior to chemotherapy on each treatment day. The antiemetics (administered intravenously or orally) will be repeated every 8 hr as needed to control nausea and/or vomiting. Treatment will be repeated every week for 4 consecutive weeks followed by a 2-week rest. This will constitute one cycle of therapy.

Diarrhea that occurs during or shortly after irinotecan infusion will be treated with atropine (0.5–1 mg) intravenously. For diarrhea occurring ≧12 hr after irinotecan administration, patients will be treated with loperamide 4 mg orally at the first sign of diarrhea followed by 2 mg orally every 2 hr (4 mg orally every 4 hr at night) until there is complete resolution of the diarrhea for at least 12 hr. If the diarrhea is bloody, associated with fevers ≧101.6° F., and continues unabated for ≧12 hr, the patient will be admitted to the hospital for further evaluation and treatment.

Dose Modification of Irinotecan: There will be no dose escalation of irinotecan in this study. Dose modification for toxicity will be made as recommended in the package insert provided by the manufacture (Table 13).

TABLE 13

Recommended Dose Modifications for the Weekly and Once-Every 3-Week Schedule.
A new course of therapy should not begin until the granulocyte count has recovered to ≧1500/mm$^3$, and the platelet count has recovered to ≧100,000/mm$^3$, and treatment-related diarrhea is fully resolved. Treatment should be delayed 1 to 2 weeks to allow for recovery from treatment-related toxicities. If the patient has not recovered after a 2 week delay, consideration should be given to discontinuing CAMPTOSAR ® (irinotecan, CPT-11).

| Weekly Toxicity NCI Grade[b] Value | During a Course of Therapy Weekly | At the Start of the Next Courses of Therapy (After Adequate Recovery), Compared with the Starting Dose in the Previous Course[a] Weekly | Once every 3 weeks |
|---|---|---|---|
| No toxicity | Maintain dose level | ↑ 25 mg/m$^2$ up to a maximum dose of 150 mg/m$^2$ | Maintain dose level |
| Neutropenia | | | |
| 1 (1500 to 1999/mm$^3$) | Maintain dose level | Maintain dose level | Maintain dose level |
| 2 (1000 to 1499/mm$^2$) | ↓ 25 mg/m$^2$ | Maintain dose level | Maintain dose level |
| 3 (550 to 999/mm$^3$) | Omit dose, then ↓ 25 mg/m$^2$ when resolved to ≦ grade 2 | ↓ 25 mg/m$^2$ | ↓ 25 mg/m$^2$ |
| 4 (<500/mm$^3$) | Omit dose, then ↓ 50 mg/m$^2$ when resolved to ≦ grade 2 | ↓ 50 mg/m$^2$ | ↓ 50 mg/m$^2$ |
| Neutropenic fever (grade 4 neutropenia & ≧ grade 2 fever) | Omit dose, then ↓ 50 mg/m$^2$ when resolved | ↓ 50 mg/m$^2$ | ↓ 50 mg/m$^2$ |
| Other hematologic Toxicities | Dose modifications for leukopenia, thrombocytopenia, and also based on NCI toxicity criteria and are the same at the start of subsequent courses of therapy are recommended for neuropenia above. | | |
| Diarrhea | | | |
| 1 (2–3 stools/day > pretx[c]) | Maintain dose level | Maintain dose level | Maintain dose level |
| 2 (4–6 stools/day > pretx[c]) | ↓ 25 mg/m$^2$ | Maintain dose level | Maintain dose level |
| 3 (7–9 stools/day > pretx[c]) | Omit dose, then ↓ 25 mg/m$^2$ when resolved to ≦ grade 2 | ↓ 25 mg/m$^2$ | ↓ 50 mg/m$^2$ |
| 4 ( = 10 stools/day > pretx[c]) | Omit dose, then ↓ 50 mg/m$^2$ when resolved to ≦ grade 2 | ↓ 50 mg/m$^2$ | ↓ 50 mg/m$^2$ |
| Other nonhemalogic Toxicities | | | |
| 1 | | Maintain dose level | Maintain dose level |
| 2 | | Maintain dose level | Maintain dose level |
| 3 | | ↓ 25 mg/m$^2$ | ↓ 25 mg/m$^2$ |
| 4 | | ↓ 50 mg/m$^2$ | |

[a]All dose modifications should be based on the worst preceding toxicity
[b]National Cancer Institute Common Toxicity Criteria
[c]Pretreatment Response and Toxicity Assessment: Toxicity will be assessed by weekly physical examination and blood counts and graded according to National Cancer Institute Common Toxicity Criteria. These evaluations and a complete chemistry profile will be repeated before each treatment.

Patients will also keep a daily record of their bowel habit and their use of anti-motility agents. This diary will include the time of ingestion of PHY906, a recording of the frequency and consistency of their bowel movements (formed, loose, or watery), and the anti-motility treatment which was used by the patient to manage this symptom.

A research nurse will contact each patient at least once a week between visits during the first cycle to reinforce instructions on the management of diarrhea and the completion of the diary. Overall quality of life including asthenia, nausea, vomiting, and loss of appetite will also be evaluated using established FAST methodology.

A pill count will be made by a pharmacist to each clinical visit for treatment to assess compliance with PHY906. An evaluation of disease response will be made after every two treatment cycles. Response will be defined according to ECOG criteria and will be assessed in all patients with measurable or evaluable disease but will not constitute an endpoint in this study.

Pharmacokinetics of Irinotecan: In selected patients, pharmacokinetic studies will be performed to assess whether PHY906 affects the metabolism and elimination of irinotecan. In these patients, the first dose of irinotecan will be given alone (cycle 1/day 1) and the PHY906 will begin on day 2.

Blood samples will be collected in heparinized tubes immediately before irinotecan administration, 30, 60, 90 min during the infusion of irinotecan and 0.5, 1.5, 3.5 and 6 h after the end of the infusion on cycle 1, day 1, and on cycle 1 day 8. Samples will be immediately processed with 2.50 µl of plasma added to 500 µl of internal standard solution in polystyrene tubes. The internal standard solution will consist of camptothecin 50 µg/ml in acetonitrile acidified with glacial acetic acid, 4.0 ml in 100 ml. The samples will be vortexed for 30 sec, placed into a 40° C. water bath for 15 min, cooled at room temperature and then mixed with 900 µl of a 25 mM triethylamine buffer (pH 4.2). The supernatant will be transferred to 1.5 ml Eppendorf tubes, centrifuged for 4 min at 13,000×g in a microcentrifuge, and an aliquot of the clear supernatant is analyzed by high performance liquid chromatography (HPLC).

Chromatographic analysis will be conducted on a Microsorh C18 (4.5×250 mm, 5 µm particle size) reverse phase HPLC column eluted with 72:28 (v/v) 25 mM TEA/acetonitrile buffer at 1 ml/min utilizing a fluorescence detector with $\lambda EX$ 372 nm and $\lambda Em$ 535 nm (Pharmacia & Upjohn SOP #UPJ-120-5). Maximum plasma concentration, terminal half-life, and AUC (area under the curve) will be determined by non-compartmental analysis of the data utilizing PC-NONLIN software (Scientific Consulting Lexington, Ky.) and standard pharmacokinetic equations. The Pharmacokinetic studies will be performed on, cycle 1/day 1 and cycle 1/day 8, to determine whether prolonged exposure to PHY906 produces a cumulative effect on the plasma clearance of irinotecan.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents, and patent applications that are identified in this patent application are incorporated by reference in their entirety.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Rererences for which a Complete Citation is not Provided in the Text of the Specification All references cited here are incorporated in their entirety.

Bienvenu J A, Monneret G, Gutowski M C. et al. Cytokine assays in human sera and tissues Toxicology 129: 55–61 (1998).

Bleiberg, H.: CPT-11 in Gastrointestinal Cancer. European Journal of Cancer, Vol. 35, No. 3, 371–379, 1999.

Bleiberg, H., Cvitkovic, E.: Characterization and clinical management of CPT-11 (irinotecan)-induced adverse events: The European perspective. Eur. J. Cancer 32A (Suppl 3):S18–S23, 1996.

Calabresi P. and Chabner B A: Chemotherapy of Neoplastic Diseases, Goodman & Gilman's The Pharmocological Basis of Therapeutics, Ninth Edition, Section X: 1225–1232, 1996.

Chabner B A, Allegra C J, Curt G A, Calabresi P.: Antineoplastic Agents, Goodman & Gilman's The Pharmocological Basis of Therapeutics, Ninth Edition, Chapter 51:1233–1287.

Chen J. J. W, Wu R, Yang P C, et al. Profiling expression patterns and isolating differentially expressed genes by cDNA microarray system with colorimetry detection. Genomics 51:313–324 (1998).

Chu, X-Y, Kato, Y, Ueda, K. et al. Biliary Excretion Mechanism of CPT-11 and Its Metabolites in Humans: Involvement of Primary Active Transporters. Cancer Res. 58:5137–5143, 1998.

Douillard J., Cunningham D., Roth A., Germa J., James R., Karasek P., Jandik P., Iveson T., Carmichael J., Gruia G., Dembak M., Slbaud D., Rougier P.: A randomized phase III trial comparing Irinotecan+5FU/Follnic Acid (FA) to the same schedule of 5FU/FA in patients (pts) with metastatic colorectal cancer (MCRC) as front line chemotherapy (CT), Proc. ASCO, Vol. 18, 233a, 1999.

Gilman, M. 1993. Ribonuclease protection assay. In Current Protocols in Molecular Biology, Vol. 1. (Ausubel, F. M., R. Brent, R. E. Kingston, D. D. Moore, J. G. Seidman, J. A. Smith and K. Stuhl, eds.), pp 4.7.1–4.7.8, John Wiley and Sons, Inc., New York.

Guo X, Lerner-Tung M, Chen H X, Chang C N, Zhu J L, Chang C P, Pizzomo G, Lin, T S, Cheng Y C. 5-Fluoro-2 pyrimidinone, A liver aldehyde oxidase-activated prodrug of 5-fluorouracil. Biochem Pharm, 49, 1111–1116 (1995)

Gupta E, Mick R, Ramirez J, Wang X, Lestingi T M, Vokes E E, Ratain M J: Pharmacokinetic and pharmacodynamic evaluation of the topoisomerase inhibitor irinotecan in cancer patients. J Clin Oncol 15:1502–1510, 1997.

Haaz M. C., Rivory, L., Riche, C., et al. Metabolism of irinotecan (CPT-11) by human hepatic microsomes: participation of cytochrome P-450 3A and drug interactions. Cancer Res 58:468–472 (1998).

Hani Oka Hiroshi, Taki No Ko Suke: Application of 212 formula of Kampo Medicine. Kabusiki Kaishya, Tokyo, Japan, 1998.

Hsu H. and Hsu C., Commonly used Chinese herbal formulas; Companion Handbook, Ohai Press.

Joulia, J., Pinguet, F., Ychou, M., Duffour, J., Astre, C. and Bressolle, F.: Plasma and Salivary Pharmacokinetics of 5-Fluorouracil (FU) in Patients with Metastatic Colorectal Cancer Receiving FU Bolus Plus Continuous Infusion with High-dose Folinic Acid. European Journal of Cancer, Vol. 35, No. 2, 26–301, 1999.

Kaneda N., Nagata H., Furuta T., Yokokura T.: Metabolism and pharmacokinetics of the camptothecin analogue CPT-11 in the mouse. Cancer Res 50:1715–1720, 1990.

Kivisto K. T., Kroemer H. K. and Eichelbaum M. The role of human cytochrome P450 enzymes in the metabolism of anticancer agents: implications for drug interactions. Br J. Clin Pharmacol 40:523–530 (1995).

Koima K., et. al. Long-term administration of Asho-saiko-to@increase cytochrome P-450 mRNA level in mouse liver. Biol. Pharm. Bull. 21:426–428, 1998.

Lombardi V. R. M, Garcia M and Cacabelos L. R. R. Characterization of cytokine production, screening of lymphocyte subset patterns and in vitro apoptosis in healthy and Alzheimer's Disease (AD) individuals. Journal of Neuroimmunol 97:163–171 (1999).

Miller C L and Eaves C J. Expansion in vitro of adult murine hematopoietic stem cells with transplantable lympho-myeloid reconstituting ability. Proc. Natl. Acad. Sci. 94:13648–13653 (1997).

Mori K., Hirose T., Machida S., Tominaga K.: Kampo medicines for the prevention of irinotecan-induced diarrhea in advanced non-small cell lung cancer. Gan To Kagaku Ryoho 25:1159–63, 1998.

Marita M., Nagai E., Hagiwara H., Aburada M., Yokoi T., Kamataki T.: Inhibition of beta-glucuronidase by natural glucuronides of kampo medicines using glucuronide of SN-38 (7-ethyl-10-hydroxycamptothecin) as a substrate. Xenobiotica 23:5–10, 1993.

Peters, G. and van Groeninger, C.: Clinical relevance of biochemical modulation of 5-fluorouracil. Annals of Oncology 2: 469–480, 1991.

Pinedo, H. and Peters, G. Fluorouracil: Biochemistry and Pharmacology. Journal of Clinical Oncology, Vol. 6, No. 10 (October), 1633–1664, 1988.

Pizzorno G., Wiegand R., Lentz S. and Handschumacher R., Brequinar Potentiates 5-Fluorouracil antitumor activity in a Murine model colon 38 tumor by tissue-specific modulation of uridine nucleotide pools. Cancer Res., 52: 1660–1665, 1992

Roby C.A., Anderson G D and Dryer D A et al. St John's Wort: Effect on CYP3A4 activity. Clin. Pharmacol. Ther. 67, 451–457 (2000).

Saliba F, Hagipantelli R, Misset J-L, Bastian G, vassal G, Bonnay M, Herait P, Cote C, Mahjoubi M, Mignard D, Cvitkovic E: Pathophysiology and therapy in irinotecan-induced delayed-onset diarrhea in patients with advanced colorectal cancer: A prospective assessment. J Clin Oncol 16:2745–2751, 1998.

Saltz L B, Locker P K, Plrotta N, Elfring G L, Miller L L: Weekly Irinotecan (CPT-11), Leucovorin (LV), and Fluorouracil (FU) is superior to daily×5 LV/FU in patients (PTS) with previously untreated metastatic colorectal cancer (CRC), Proc. ASCO, Vol.18, 233a, 1999.

Stucky-Marshall, L.: New Agents in Gastrointestinal Malignancies: Part 1: Irinotecan in Clinical Practice, Cancer Nursing, 22(3): 212–219, 1999.

Takasuna K, Takehiro H, Hirohashi M, Kato M, et al. Involvement of b-glucuronidase in intestinal microflora in the intestinal toxicity of the antitumor camptothecin derivative irinotecan hydrochloride (CPT-11) in rats. Cancer Res. 56:3752–3757 (1996).

Takasuna K, Takehiro H, Hirohashi M, et al. Inhibition of intestinal microflora-glucuronidase modifies the distribution of the active metabolite of the antitumor agent, irinotecan hydrochloride (CPT-11) in rats. Cancer Chemother Pharmacol. 42:280–286 (1998).

Wasserman E., Myara A., Lokiec F., Goldwasser F., Trivin F., Mahjoubi M., Misset J., Cvitkovic E.: Severe CPT-11 toxicity in patients with Gilbert's syndrome: Two case reports. Ann Oncol 8:1049–1051, 1997.

Wierda D. and Matamoros M. Partial characterization of bone marrow hemopoiesis in mice after cisplatin administration. Toxicol & Applied Pharmacol 75:25–34 (1984).

Xu Guo-Jun, Introduction to the Chinese Materia Medica, China Pharmaceutical Science Publication Inc., Beijin, China, 1996, p. 398.

What is claimed is:

1. A composition comprising:
   i) a pharmaceutically acceptable carrier;
   ii) an herbal preparation consisting essentially of *Scutellaria*, *Glycyrrhiza*, *Ziziphus* and *Paeonia;* and
   iii) a chemotherapeutic formulation comprising a chemotherapeutic compound selected from the group consisting of irinotecan (CPT-11). 5-fluorouracil (5-FU), etoposide (VP-16), leucovorin (LV), and beta-1-dioxolane-cytidine (OddC).

2. The composition of claim 1 wherein the herbal preparation consists of *Scutellaria baicalensis*, *Glycyrrhiza uralensis*, *Ziziphus jujuba*, and *Paeonia lactiflora*.

3. The composition of claim 1, wherein the chemotherapeutic formulation comprises CPT-11, 5-FU, and LV.

4. A method of treating tumors in a mammal comprising administering a therapeutically effective amount of a composition comprising:
   i) a pharmaceutically acceptable carrier;
   ii) an herbal preparation cosisting essentially of *Scutellaria*, *Glycyrrhiza*, *Ziziphus* and *Paeonia;* and
   iii) a chemotherapeutic formulation comprising a chemotherapeutic compound selected from the group consisting of CPT-11, 5-FU, VP-16, LV, and OddC.

5. A method of relieving side effects of a chemotherapeutic compound in a mammal comprising administering a composition comprising:
   i) a pharmaceutically acceptable carrier;
   ii) an herbal preparation consisting essentially of *Scutellaria*, *Glycyrrhiza*, *Ziziphus* and *Paeonia;* and
   iii) the chemotherapeutic formulation comprising the chemotherapeutic compound, wherein the chemotherapeutic compound is selected from the group consisting of CPT-11, 5-FU, VP-16, LV, and OddC.

6. A method of enhancing therapeutic effectiveness of a chemotherapeutic formulation in a mammal comprising administering a composition comprising:
   i) a pharmaceutically acceptable carrier;
   ii) an herbal preparation consisting essentially of *Scutellaria*, *Glycyrrhiza*, *Ziziphus* and *Paeonia;* and
   iii) the chemotherapeutic formulation comprising a chemotherapeutic compound, wherein the chemotherapeutic compound is selected from the group consisting of CPT-11, 5-FU, VP-16, LV, and OddC.

7. A method of enhancing antitumor activity of a chemotherapeutic compound in a mammal comprising administering a composition comprising:
   i) a pharmaceutically acceptable carrier;
   ii) an herbal preparation consisting essentially of *Scutellaria*, *Glycyrrhiza*, *Ziziphus* and *Paeonia;* and iii) the chemotherapeutic formulation comprising the chemotherapeutic compound, wherein the chemotherapeutic compound is selected from the group consisting of CPT-11, 5-FU, VP-16, LV, and OddC.

8. A method of inhibiting the growth of tumors in a mammal, comprising administering a composition comprising:
   i) a pharmaceutically acceptable carrier;
   ii) an herbal preparation consisting essentially of *Scutellaria, Glycyrrhiza, Ziziphus* and *Paeonia;* and
   iii) a chemotherapeutic formulation comprising a chemotherapeutic compound selected from the group consisting of CPT-11, 5-FU, VP-16, LV, and OddC.

9. The method of any one of claims, 4, 5, 6, 7 and 8 wherein the mammal is a human.

10. A method of inhibiting the growth of tumors, comprising administering a composition comprising:
   i) a pharmaceutically acceptable carrier;
   ii) an herbal preparation consisting essentially of *Scutellaria, Glycyrrhiza, Ziziphus* and *Paeonia;* and
   iii) a chemotherapeutic formulation comprising a chemotherapeutic compound selected from the group consisting of CPT-11, 5-FU, VP-16, LV, and OddC.

11. The method of claim 10, wherein the tumors are present in in vitro cells.

12. The method of any one of claims 5, 6, 7, 8, or 10, wherein the chemotherapeutic formulation comprises CPT-11, 5-FU, and LV.

13. The method of any one of claims 4, 5, 6, 7, 8, and 10, wherein the herbal preparation consists of *Scutellaria baicalensis, Glycyrrhiza uralensis, Ziziphus jujuba,* and *Paeonia lactiflora.*

* * * * *